US008992595B2

(12) United States Patent
Parsons et al.

(10) Patent No.: US 8,992,595 B2
(45) Date of Patent: Mar. 31, 2015

(54) DURABLE STENT GRAFT WITH TAPERED STRUTS AND STABLE DELIVERY METHODS AND DEVICES

(71) Applicant: TriVascular, Inc., Santa Rosa, CA (US)

(72) Inventors: Dennis Parsons, Santa Rosa, CA (US); Christopher Staudenmayer, Santa Rosa, CA (US); James Watson, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 0 days.

(21) Appl. No.: 13/799,207

(22) Filed: Mar. 13, 2013

(65) Prior Publication Data
US 2013/0268044 A1    Oct. 10, 2013

Related U.S. Application Data

(60) Provisional application No. 61/620,362, filed on Apr. 4, 2012.

(51) Int. Cl.
*A61F 2/06*   (2013.01)
*A61F 2/07*   (2013.01)
(Continued)

(52) U.S. Cl.
CPC ... *A61F 2/07* (2013.01); *A61F 2/82* (2013.01); *A61F 2/848* (2013.01); *A61F 2/962* (2013.01); *A61F 2/88* (2013.01); *A61F 2/89* (2013.01); *A61F 2/91* (2013.01); *A61F 2002/065* (2013.01); *A61F 2002/067* (2013.01); *A61F 2002/072* (2013.01); *A61F 2002/075* (2013.01); *A61F 2002/825* (2013.01); *A61F 2002/9665* (2013.01);

(Continued)

(58) Field of Classification Search
CPC ................ A61F 2002/072; A61F 2002/075; A61F 2/07
USPC ........... 623/1.13, 1.14, 1.15, 1.16, 1.17, 1.18, 623/1.19, 1.2, 1.21, 1.31, 5; 606/159
See application file for complete search history.

(56) References Cited

U.S. PATENT DOCUMENTS

| 3,076,737 A | 2/1963 | Roberts |
| 3,540,431 A | 11/1970 | Uddin |

(Continued)

FOREIGN PATENT DOCUMENTS

| CA | 2438087 | 3/2001 |
| DE | 19624642 | 1/1998 |

(Continued)

OTHER PUBLICATIONS

US 6,413,270, 7/2002, Thornton et al. (withdrawn).

(Continued)

*Primary Examiner* — Todd Manahan
*Assistant Examiner* — Charles A Lutzow, III
(74) *Attorney, Agent, or Firm* — Anderson IP, Inc.

(57) ABSTRACT

Some embodiments relate in part to endovascular prostheses and methods of deploying same. Embodiments may be directed more specifically to stent grafts and methods of making and deploying same within the body of a patient. Stent embodiments may include tapered struts for an even distribution of strain. Stent embodiments may also include portions which are enlarged in a circumferential direction which may be configured to stabilize the stent in a constrained state.

2 Claims, 16 Drawing Sheets

(51) Int. Cl.
    *A61F 2/82*               (2013.01)
    *A61F 2/848*           (2013.01)
    *A61F 2/962*           (2013.01)
    A61F 2/88              (2006.01)
    A61F 2/89              (2013.01)
    A61F 2/91              (2013.01)
    A61F 2/966            (2013.01)

(52) U.S. Cl.
    CPC . *A61F 2230/0006* (2013.01); *A61F 2230/0008* (2013.01); *A61F 2230/0019* (2013.01); *A61F 2230/0026* (2013.01); *A61F 2230/0078* (2013.01); *A61F 2250/0003* (2013.01); *A61F 2250/0036* (2013.01); *A61F 2220/0016* (2013.01); *A61F 2220/005* (2013.01); *A61F 2220/0058* (2013.01); *A61F 2220/0075* (2013.01); *A61F 2230/0013* (2013.01)
    USPC ....... 623/1.13; 623/1.14; 623/1.15; 623/1.16; 623/1.17

(56) References Cited

U.S. PATENT DOCUMENTS

| | | | |
|---|---|---|---|
| 3,631,854 A | 1/1972 | Fryer et al. | |
| 3,657,744 A | 4/1972 | Ersek | |
| 3,669,586 A | 6/1972 | Kramer | |
| 3,814,137 A | 6/1974 | Martinez | |
| 3,818,511 A | 6/1974 | Goldberg et al. | |
| 3,902,198 A | 9/1975 | Rathjen | |
| 3,991,767 A | 11/1976 | Miller et al. | |
| 4,096,227 A | 6/1978 | Gore | |
| 4,110,392 A | 8/1978 | Yamasaki | |
| 4,140,126 A | 2/1979 | Choudhury | |
| 4,183,102 A | 1/1980 | Guiset | |
| 4,187,390 A | 2/1980 | Gore | |
| 4,208,745 A | 6/1980 | Okita | |
| 4,214,587 A | 7/1980 | Sakura, Jr. | |
| 4,229,838 A | 10/1980 | Mano | |
| 4,248,924 A | 2/1981 | Okita | |
| 4,330,126 A * | 5/1982 | Rumble | 473/323 |
| 4,385,093 A | 5/1983 | Hubis | |
| 4,416,028 A | 11/1983 | Eriksson et al. | |
| 4,434,797 A | 3/1984 | Silander | |
| 4,459,252 A | 7/1984 | MacGregor | |
| 4,474,630 A | 10/1984 | Planck et al. | |
| 4,478,665 A | 10/1984 | Hubis | |
| 4,482,516 A | 11/1984 | Bowman et al. | |
| 4,497,074 A | 2/1985 | Rey et al. | |
| 4,503,569 A | 3/1985 | Dotter | |
| 4,512,338 A | 4/1985 | Balko et al. | |
| 4,550,447 A | 11/1985 | Seiler, Jr. et al. | |
| 4,552,707 A | 11/1985 | How | |
| 4,562,596 A | 1/1986 | Kornberg | |
| 4,577,631 A | 3/1986 | Kreamer | |
| 4,580,568 A | 4/1986 | Gianturco | |
| 4,592,754 A | 6/1986 | Gupte et al. | |
| 4,617,932 A | 10/1986 | Kornberg | |
| 4,647,416 A | 3/1987 | Seiler, Jr. et al. | |
| 4,655,769 A | 4/1987 | Zachariades | |
| 4,655,771 A | 4/1987 | Wallsten | |
| 4,665,906 A | 5/1987 | Jervis | |
| 4,705,517 A | 11/1987 | DiPisa, Jr. | |
| 4,731,073 A | 3/1988 | Robinson | |
| 4,733,665 A | 3/1988 | Palmaz | |
| 4,739,762 A | 4/1988 | Palmaz | |
| 4,740,207 A | 4/1988 | Kreamer | |
| 4,743,480 A | 5/1988 | Campbell et al. | |
| 4,760,102 A | 7/1988 | Moriyama et al. | |
| 4,776,337 A | 10/1988 | Palmaz | |
| 4,787,899 A | 11/1988 | Lazarus | |
| 4,816,028 A | 3/1989 | Kapadia et al. | |
| 4,830,003 A | 5/1989 | Wolff et al. | |
| 4,856,516 A | 8/1989 | Hillstead | |
| 4,871,365 A | 10/1989 | Dumican | |
| 4,877,661 A | 10/1989 | House et al. | |
| 4,902,423 A | 2/1990 | Bacino | |
| 4,932,938 A | 6/1990 | Goldberg et al. | |
| 4,941,870 A | 7/1990 | Okada et al. | |
| 4,955,899 A | 9/1990 | Della et al. | |
| 4,957,669 A | 9/1990 | Primm | |
| 4,985,296 A | 1/1991 | Mortimer, Jr. | |
| 4,994,071 A | 2/1991 | MacGregor | |
| 4,994,077 A | 2/1991 | Dobben | |
| 5,019,090 A | 5/1991 | Pinchuk | |
| 5,041,126 A | 8/1991 | Gianturco | |
| 5,052,998 A | 10/1991 | Zimmon | |
| 5,059,211 A | 10/1991 | Stack et al. | |
| 5,064,435 A | 11/1991 | Porter | |
| 5,098,625 A | 3/1992 | Huang et al. | |
| 5,100,422 A | 3/1992 | Berguer et al. | |
| 5,104,399 A | 4/1992 | Lazarus | |
| 5,104,400 A | 4/1992 | Berguer et al. | |
| 5,104,404 A | 4/1992 | Wolff | |
| 5,108,424 A | 4/1992 | Hoffman, Jr. et al. | |
| 5,110,527 A | 5/1992 | Harada et al. | |
| 5,116,365 A | 5/1992 | Hillstead | |
| 5,122,154 A | 6/1992 | Rhodes | |
| 5,123,917 A | 6/1992 | Lee | |
| 5,133,732 A | 7/1992 | Wiktor | |
| 5,135,536 A | 8/1992 | Hillstead | |
| 5,139,480 A | 8/1992 | Hickle et al. | |
| 5,150,304 A | 9/1992 | Berchem et al. | |
| 5,151,105 A | 9/1992 | Kwan-Gett | |
| 5,152,782 A | 10/1992 | Kowligi et al. | |
| 5,156,620 A | 10/1992 | Pigott | |
| 5,158,548 A | 10/1992 | Lau et al. | |
| 5,163,955 A | 11/1992 | Love | |
| 5,167,614 A | 12/1992 | Tessmann | |
| 5,171,262 A | 12/1992 | MacGregor | |
| 5,192,310 A | 3/1993 | Herweck et al. | |
| 5,195,984 A | 3/1993 | Schatz | |
| 5,197,976 A | 3/1993 | Herweck et al. | |
| 5,197,978 A | 3/1993 | Hess | |
| 5,201,757 A | 4/1993 | Heyn et al. | |
| 5,202,352 A | 4/1993 | Okada et al. | |
| 5,207,695 A | 5/1993 | Trout, III | |
| 5,217,483 A | 6/1993 | Tower | |
| 5,219,355 A | 6/1993 | Parodi et al. | |
| 5,226,913 A | 7/1993 | Pinchuk | |
| 5,234,456 A | 8/1993 | Silvestini | |
| 5,250,059 A | 10/1993 | Andreas et al. | |
| 5,275,622 A | 1/1994 | Lazarus et al. | |
| 5,282,823 A | 2/1994 | Schwartz et al. | |
| 5,282,824 A | 2/1994 | Gianturco | |
| 5,282,847 A | 2/1994 | Trescony et al. | |
| 5,290,305 A | 3/1994 | Inoue | |
| 5,292,331 A | 3/1994 | Boneau | |
| 5,304,200 A | 4/1994 | Spaulding | |
| 5,314,472 A | 5/1994 | Fontaine | |
| 5,316,023 A | 5/1994 | Palmaz et al. | |
| 5,320,100 A | 6/1994 | Herweck et al. | |
| 5,321,109 A | 6/1994 | Bosse et al. | |
| 5,330,528 A | 7/1994 | Lazim | |
| 5,334,164 A | 8/1994 | Guy et al. | |
| 5,334,201 A | 8/1994 | Cowan | |
| 5,344,426 A | 9/1994 | Lau et al. | |
| 5,344,444 A | 9/1994 | Glastra | |
| 5,344,451 A | 9/1994 | Dayton | |
| 5,350,398 A | 9/1994 | Pavcnik | |
| 5,354,310 A | 10/1994 | Garnic et al. | |
| 5,354,329 A | 10/1994 | Whalen | |
| 5,360,443 A | 11/1994 | Barone et al. | |
| 5,365,996 A | 11/1994 | Crook | |
| 5,366,504 A | 11/1994 | Andersen et al. | |
| 5,370,682 A | 12/1994 | Schmitt | |
| 5,370,691 A | 12/1994 | Samson | |
| 5,374,473 A | 12/1994 | Knox et al. | |
| 5,382,261 A | 1/1995 | Palmaz | |
| 5,383,892 A | 1/1995 | Cardon et al. | |
| 5,383,928 A | 1/1995 | Scott et al. | |
| 5,387,235 A | 2/1995 | Chuter et al. | |
| 5,389,106 A | 2/1995 | Tower et al. | |
| 5,391,147 A | 2/1995 | Imran et al. | |

(56) References Cited

U.S. PATENT DOCUMENTS

| | | |
|---|---|---|
| 5,397,345 A | 3/1995 | Lazarus |
| 5,405,377 A | 4/1995 | Cragg |
| 5,405,378 A | 4/1995 | Strecker |
| 5,405,379 A | 4/1995 | Lane |
| 5,411,550 A | 5/1995 | Herweck et al. |
| 5,415,634 A | 5/1995 | Glynn et al. |
| 5,423,851 A | 6/1995 | Samuels |
| 5,433,909 A | 7/1995 | Martakos et al. |
| 5,437,900 A | 8/1995 | Kuzowski |
| 5,441,515 A | 8/1995 | Khosravi et al. |
| 5,443,458 A | 8/1995 | Eury |
| 5,443,498 A | 8/1995 | Fountaine |
| 5,445,646 A | 8/1995 | Euteneuer et al. |
| 5,447,152 A | 9/1995 | Kohsai et al. |
| 5,449,373 A | 9/1995 | Pinchasik et al. |
| 5,456,713 A | 10/1995 | Chuter |
| 5,464,419 A | 11/1995 | Glastra |
| 5,464,449 A | 11/1995 | Ryan et al. |
| 5,466,509 A | 11/1995 | Kowllgl et al. |
| 5,474,824 A | 12/1995 | Martakos et al. |
| 5,476,506 A | 12/1995 | Lunn |
| 5,476,589 A | 12/1995 | Bacino |
| 5,478,330 A | 12/1995 | Imran et al. |
| 5,480,423 A | 1/1996 | Ravenscroft et al. |
| 5,489,295 A | 2/1996 | Piplani et al. |
| 5,505,887 A | 4/1996 | Zdrahala et al. |
| 5,507,769 A | 4/1996 | Marin et al. |
| 5,507,770 A | 4/1996 | Turk |
| 5,512,360 A | 4/1996 | King |
| 5,514,154 A | 5/1996 | Lau et al. |
| 5,522,880 A | 6/1996 | Barone et al. |
| 5,522,881 A | 6/1996 | Lentz |
| 5,522,883 A | 6/1996 | Slater et al. |
| 5,524,633 A | 6/1996 | Heaven et al. |
| 5,527,353 A | 6/1996 | Schmitt |
| 5,527,355 A | 6/1996 | Ahn |
| 5,529,653 A | 6/1996 | Glastra |
| 5,529,820 A | 6/1996 | Nomi et al. |
| 5,534,024 A | 7/1996 | Rogers et al. |
| 5,536,274 A | 7/1996 | Neuss |
| 5,545,135 A | 8/1996 | Iacob et al. |
| 5,549,662 A | 8/1996 | Fordenbacher |
| 5,549,663 A | 8/1996 | Cottone, Jr. |
| 5,552,100 A | 9/1996 | Shannon et al. |
| 5,554,180 A | 9/1996 | Turk |
| 5,554,181 A | 9/1996 | Das |
| 5,554,183 A | 9/1996 | Nazari |
| 5,554,185 A | 9/1996 | Block et al. |
| 5,556,414 A | 9/1996 | Turi |
| 5,556,426 A | 9/1996 | Popadiuk et al. |
| 5,560,986 A | 10/1996 | Mortimer, Jr. |
| 5,562,697 A | 10/1996 | Christiansen |
| 5,562,724 A | 10/1996 | Vorwerk et al. |
| 5,562,726 A | 10/1996 | Chuter |
| 5,562,727 A | 10/1996 | Turk et al. |
| 5,562,728 A | 10/1996 | Lazarus et al. |
| 5,569,295 A | 10/1996 | Lam |
| 5,571,171 A | 11/1996 | Barone et al. |
| 5,571,172 A | 11/1996 | Chin |
| 5,571,173 A | 11/1996 | Parodi |
| 5,575,817 A | 11/1996 | Martin |
| 5,575,818 A | 11/1996 | Pinchuk |
| 5,578,071 A | 11/1996 | Parodi |
| 5,578,072 A | 11/1996 | Barone et al. |
| 5,588,964 A | 12/1996 | Imran et al. |
| 5,591,195 A | 1/1997 | Taheri et al. |
| 5,591,197 A | 1/1997 | Orth et al. |
| 5,591,229 A | 1/1997 | Parodi |
| 5,597,378 A | 1/1997 | Jervis |
| 5,603,721 A | 2/1997 | Lau et al. |
| 5,607,478 A | 3/1997 | Lentz et al. |
| 5,609,624 A | 3/1997 | Kalis |
| 5,609,625 A | 3/1997 | Piplani et al. |
| 5,609,627 A | 3/1997 | Goicoechea et al. |
| 5,609,628 A | 3/1997 | Keranen |
| 5,609,629 A | 3/1997 | Fearnot |
| 5,612,885 A | 3/1997 | Love |
| 5,618,301 A | 4/1997 | Hauenstein et al. |
| 5,620,763 A | 4/1997 | House et al. |
| 5,626,599 A | 5/1997 | Bourne et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,632,772 A | 5/1997 | Alcime et al. |
| 5,632,840 A | 5/1997 | Campbell |
| 5,639,278 A | 6/1997 | Dereume et al. |
| 5,641,373 A | 6/1997 | Shannon et al. |
| 5,645,915 A | 7/1997 | Kranzler et al. |
| 5,649,978 A | 7/1997 | Samson |
| 5,653,745 A | 8/1997 | Trescony et al. |
| 5,653,746 A | 8/1997 | Schmitt |
| 5,656,029 A | 8/1997 | Imran et al. |
| 5,662,675 A | 9/1997 | Stockert et al. |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Bynon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,451 A | 11/1997 | Lenker et al. |
| 5,683,453 A | 11/1997 | Palmaz |
| 5,690,644 A | 11/1997 | Yurek et al. |
| 5,693,083 A | 12/1997 | Baker et al. |
| 5,693,084 A | 12/1997 | Chuter |
| 5,693,087 A | 12/1997 | Parodi |
| 5,693,088 A | 12/1997 | Lazarus |
| 5,697,968 A | 12/1997 | Rogers et al. |
| 5,697,971 A | 12/1997 | Fischell et al. |
| 5,700,285 A | 12/1997 | Myers et al. |
| 5,707,378 A | 1/1998 | Ahn et al. |
| 5,707,388 A | 1/1998 | Lauterjung |
| 5,708,044 A | 1/1998 | Branca |
| 5,709,701 A | 1/1998 | Parodi |
| 5,709,703 A | 1/1998 | Lukie et al. |
| 5,712,315 A | 1/1998 | Dolan |
| 5,713,917 A | 2/1998 | Leonhardt et al. |
| 5,716,393 A | 2/1998 | Lindenberg et al. |
| 5,716,395 A | 2/1998 | Myers et al. |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,725,549 A | 3/1998 | Lam |
| 5,728,131 A | 3/1998 | Frantzen et al. |
| 5,733,303 A | 3/1998 | Israel et al. |
| 5,733,325 A | 3/1998 | Robinson et al. |
| 5,735,892 A | 4/1998 | Myers et al. |
| 5,735,893 A | 4/1998 | Lau et al. |
| 5,735,897 A | 4/1998 | Buirge |
| 5,741,324 A | 4/1998 | Glastra |
| 5,741,325 A | 4/1998 | Chaikof et al. |
| 5,747,128 A | 5/1998 | Campbell et al. |
| 5,749,880 A | 5/1998 | Banas et al. |
| 5,749,894 A | 5/1998 | Engleson |
| 5,749,920 A | 5/1998 | Quiachon et al. |
| 5,749,921 A | 5/1998 | Lenker et al. |
| 5,755,772 A | 5/1998 | Evans et al. |
| 5,755,776 A | 5/1998 | Al-Saadon |
| 5,766,203 A | 6/1998 | Imran et al. |
| 5,769,882 A | 6/1998 | Fogarty et al. |
| 5,769,885 A | 6/1998 | Quiachon et al. |
| 5,769,887 A | 6/1998 | Brown et al. |
| 5,772,884 A | 6/1998 | Tanaka et al. |
| 5,776,142 A | 7/1998 | Gunderson |
| 5,776,161 A | 7/1998 | Globerman |
| 5,776,183 A | 7/1998 | Kanesaka et al. |
| 5,780,807 A | 7/1998 | Saunders |
| 5,782,789 A | 7/1998 | Herweck et al. |

(56) References Cited

U.S. PATENT DOCUMENTS

| | | |
|---|---|---|
| 5,782,838 A | 7/1998 | Beyar et al. |
| 5,782,904 A | 7/1998 | White et al. |
| 5,782,909 A | 7/1998 | Quiachon et al. |
| 5,785,679 A | 7/1998 | Abolfathi et al. |
| 5,788,626 A | 8/1998 | Thompson |
| 5,789,047 A | 8/1998 | Sasaki et al. |
| 5,797,951 A | 8/1998 | Mueller |
| 5,798,924 A | 8/1998 | Eufinger et al. |
| 5,799,384 A | 9/1998 | Schwartz et al. |
| 5,800,508 A | 9/1998 | Goicoechea et al. |
| 5,800,512 A | 9/1998 | Lentz et al. |
| 5,800,515 A | 9/1998 | Nadal et al. |
| 5,800,518 A | 9/1998 | Piplani et al. |
| 5,800,522 A | 9/1998 | Campbell et al. |
| 5,800,524 A | 9/1998 | Borghi |
| 5,800,526 A | 9/1998 | Anderson et al. |
| 5,810,870 A | 9/1998 | Myers et al. |
| 5,810,872 A | 9/1998 | Kanesaka et al. |
| 5,814,405 A | 9/1998 | Branca et al. |
| 5,817,102 A | 10/1998 | Johnson et al. |
| 5,824,037 A | 10/1998 | Fogarty et al. |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,046 A | 10/1998 | Smith et al. |
| 5,824,058 A | 10/1998 | Ravenscroft et al. |
| 5,827,289 A | 10/1998 | Reiley et al. |
| 5,827,310 A | 10/1998 | Marin et al. |
| 5,827,320 A | 10/1998 | Richter et al. |
| 5,827,321 A | 10/1998 | Roubin et al. |
| 5,833,651 A | 11/1998 | Donovan et al. |
| 5,833,707 A | 11/1998 | Mcintyre et al. |
| 5,836,964 A | 11/1998 | Richter et al. |
| 5,836,966 A | 11/1998 | St. Germain |
| 5,840,775 A | 11/1998 | Howard, Jr. et al. |
| 5,843,158 A | 12/1998 | Lenker et al. |
| 5,843,160 A | 12/1998 | Rhodes |
| 5,843,162 A | 12/1998 | Inoue |
| 5,843,164 A | 12/1998 | Frantzen et al. |
| 5,843,166 A | 12/1998 | Lentz et al. |
| 5,843,167 A | 12/1998 | Dwyer et al. |
| 5,843,170 A | 12/1998 | Ahn |
| 5,843,173 A | 12/1998 | Shannon et al. |
| 5,843,175 A | 12/1998 | Frantzen |
| 5,853,419 A | 12/1998 | Imran |
| 5,855,598 A | 1/1999 | Pinchuk |
| 5,858,556 A | 1/1999 | Eckert et al. |
| 5,861,027 A | 1/1999 | Trapp |
| 5,871,536 A | 2/1999 | Lazarus |
| 5,871,537 A | 2/1999 | Holman et al. |
| 5,871,538 A | 2/1999 | Dereume |
| 5,873,906 A | 2/1999 | Lau et al. |
| 5,876,432 A | 3/1999 | Lau et al. |
| 5,891,193 A | 4/1999 | Robinson et al. |
| 5,904,713 A | 5/1999 | Leschinsky |
| 5,906,619 A | 5/1999 | Olson et al. |
| 5,906,641 A | 5/1999 | Thompson et al. |
| 5,910,168 A | 6/1999 | Meyers et al. |
| 5,910,277 A | 6/1999 | Ishino et al. |
| 5,911,754 A | 6/1999 | Kanesaka et al. |
| 5,916,264 A | 6/1999 | Von Oepen et al. |
| 5,919,204 A | 7/1999 | Lukic et al. |
| 5,922,020 A | 7/1999 | Klein et al. |
| 5,925,061 A | 7/1999 | Ogi et al. |
| 5,925,075 A | 7/1999 | Myers et al. |
| 5,931,865 A | 8/1999 | Silverman et al. |
| 5,935,667 A | 8/1999 | Calcote et al. |
| 5,939,198 A | 8/1999 | Howard, Jr. et al. |
| 5,944,750 A | 8/1999 | Tanner et al. |
| 5,948,016 A | 9/1999 | Jang |
| 5,954,729 A | 9/1999 | Bachmann et al. |
| 5,955,016 A | 9/1999 | Goldfarb |
| 5,957,973 A | 9/1999 | Quiachon et al. |
| 5,961,545 A | 10/1999 | Lentz et al. |
| 5,961,546 A | 10/1999 | Robinson et al. |
| 5,968,068 A | 10/1999 | Dehdashtian et al. |
| 5,968,090 A | 10/1999 | Ratcliff et al. |
| 5,972,023 A | 10/1999 | Tanner et al. |
| 5,972,027 A | 10/1999 | Johnson |
| 5,972,441 A | 10/1999 | Campbell et al. |
| 5,976,155 A | 11/1999 | Foreman et al. |
| 5,976,179 A | 11/1999 | Inoue |
| 5,976,192 A | 11/1999 | McIntyre et al. |
| 5,976,650 A | 11/1999 | Campbell et al. |
| 5,980,530 A | 11/1999 | Willard et al. |
| 5,980,570 A | 11/1999 | Simpson |
| 5,984,955 A | 11/1999 | Wisselink |
| 5,984,956 A | 11/1999 | Tweden et al. |
| 5,984,964 A | 11/1999 | Roberts et al. |
| 5,989,287 A | 11/1999 | Yang et al. |
| 5,993,481 A | 11/1999 | Marcade et al. |
| 5,993,489 A | 11/1999 | Lewis et al. |
| 5,997,573 A | 12/1999 | Quijano et al. |
| 6,001,123 A | 12/1999 | Lau |
| 6,004,346 A | 12/1999 | Wolff et al. |
| 6,004,347 A | 12/1999 | McNamara et al. |
| 6,004,348 A | 12/1999 | Banas et al. |
| 6,007,575 A | 12/1999 | Samuels |
| 6,015,429 A | 1/2000 | Lau et al. |
| 6,015,431 A | 1/2000 | Thornton et al. |
| 6,015,432 A | 1/2000 | Rakos et al. |
| 6,017,362 A | 1/2000 | Lau |
| 6,017,364 A | 1/2000 | Lazarus |
| 6,019,778 A | 2/2000 | Wilson et al. |
| 6,019,779 A | 2/2000 | Thorud et al. |
| 6,019,787 A | 2/2000 | Richard et al. |
| 6,022,359 A | 2/2000 | Frantzen |
| 6,024,763 A | 2/2000 | Lenker et al. |
| 6,025,044 A | 2/2000 | Campbell et al. |
| 6,027,779 A | 2/2000 | Campbell et al. |
| 6,027,811 A | 2/2000 | Campbell et al. |
| 6,030,413 A | 2/2000 | Lazarus |
| 6,030,414 A | 2/2000 | Taheri |
| 6,030,415 A | 2/2000 | Chuter |
| 6,036,640 A | 3/2000 | Corace et al. |
| 6,036,702 A | 3/2000 | Bachinski et al. |
| 6,036,723 A | 3/2000 | Anidjar et al. |
| 6,036,724 A | 3/2000 | Lentz et al. |
| 6,036,725 A | 3/2000 | Avellanet |
| 6,039,754 A | 3/2000 | Caro |
| 6,039,758 A | 3/2000 | Quiachon et al. |
| 6,042,589 A | 3/2000 | Marianne |
| 6,042,605 A | 3/2000 | Martin et al. |
| 6,042,606 A | 3/2000 | Frantzen |
| 6,045,557 A | 4/2000 | White et al. |
| 6,048,484 A | 4/2000 | House et al. |
| 6,051,020 A | 4/2000 | Goicoechea et al. |
| 6,053,943 A | 4/2000 | Edwin et al. |
| 6,059,821 A | 5/2000 | Anidjar et al. |
| 6,059,823 A | 5/2000 | Holman et al. |
| 6,060,534 A | 5/2000 | Ronan et al. |
| 6,063,114 A | 5/2000 | Nash et al. |
| 6,068,626 A | 5/2000 | Harrington et al. |
| 6,070,589 A | 6/2000 | Keith et al. |
| 6,074,341 A | 6/2000 | Anderson et al. |
| 6,075,180 A | 6/2000 | Sharber et al. |
| 6,077,296 A | 6/2000 | Shokoohi et al. |
| 6,077,297 A | 6/2000 | Robinson et al. |
| 6,077,298 A | 6/2000 | Tu et al. |
| 6,090,128 A | 7/2000 | Douglas |
| 6,093,203 A | 7/2000 | Uflacker |
| 6,096,052 A | 8/2000 | Callister et al. |
| 6,096,070 A | 8/2000 | Ragheb et al. |
| 6,098,630 A | 8/2000 | Papazoglou |
| 6,102,918 A | 8/2000 | Kerr |
| 6,102,938 A | 8/2000 | Evans et al. |
| 6,102,940 A | 8/2000 | Robichon et al. |
| 6,103,172 A | 8/2000 | Newman et al. |
| 6,106,548 A | 8/2000 | Roubin et al. |
| 6,110,198 A | 8/2000 | Fogarty et al. |
| 6,113,628 A | 9/2000 | Borghi |
| 6,117,168 A | 9/2000 | Yang et al. |
| 6,123,722 A | 9/2000 | Fogarty et al. |

(56) References Cited

U.S. PATENT DOCUMENTS

| | | |
|---|---|---|
| 6,124,523 A | 9/2000 | Banas et al. |
| 6,126,685 A | 10/2000 | Lenker et al. |
| 6,129,756 A | 10/2000 | Kugler et al. |
| 6,132,457 A | 10/2000 | Chobotov |
| 6,132,459 A | 10/2000 | Piplani et al. |
| 6,139,572 A | 10/2000 | Campbell et al. |
| 6,142,973 A | 11/2000 | Carleton et al. |
| 6,143,014 A | 11/2000 | Dehdashtian et al. |
| 6,143,015 A | 11/2000 | Nobles |
| 6,143,016 A | 11/2000 | Bleam et al. |
| 6,143,021 A | 11/2000 | Staehle |
| 6,143,022 A | 11/2000 | Shull et al. |
| 6,146,389 A | 11/2000 | Geitz |
| 6,146,416 A | 11/2000 | Andersen et al. |
| 6,146,417 A | 11/2000 | Ischinger |
| 6,149,665 A | 11/2000 | Gabbay |
| 6,149,681 A | 11/2000 | Houser et al. |
| 6,149,682 A | 11/2000 | Frid |
| 6,152,944 A | 11/2000 | Holman et al. |
| 6,152,956 A | 11/2000 | Pierce |
| 6,156,063 A | 12/2000 | Douglas |
| 6,156,064 A | 12/2000 | Chouinard |
| 6,159,229 A | 12/2000 | Jendersee et al. |
| 6,159,237 A | 12/2000 | Alt et al. |
| 6,159,238 A | 12/2000 | Killion et al. |
| 6,159,239 A | 12/2000 | Greenhalgh |
| 6,159,565 A | 12/2000 | Campbell et al. |
| 6,162,243 A | 12/2000 | Gray et al. |
| 6,162,245 A | 12/2000 | Jayaraman |
| 6,162,246 A | 12/2000 | Barone |
| 6,165,210 A | 12/2000 | Lau et al. |
| 6,165,211 A | 12/2000 | Thompson |
| 6,165,212 A | 12/2000 | Dereume et al. |
| 6,165,213 A | 12/2000 | Goicoechea et al. |
| 6,165,214 A | 12/2000 | Lazarus |
| 6,168,610 B1 | 1/2001 | Marin et al. |
| 6,168,614 B1 | 1/2001 | Andersen et al. |
| 6,168,616 B1 | 1/2001 | Brown, III |
| 6,168,617 B1 | 1/2001 | Blaeser et al. |
| 6,168,618 B1 | 1/2001 | Frantzen |
| 6,168,619 B1 | 1/2001 | Dinh et al. |
| 6,168,620 B1 | 1/2001 | Kerr |
| 6,174,326 B1 | 1/2001 | Kitaoka et al. |
| 6,183,481 B1 | 2/2001 | Lee et al. |
| 6,183,504 B1 | 2/2001 | Inoue |
| 6,187,034 B1 | 2/2001 | Frantzen |
| 6,187,036 B1 | 2/2001 | Shaolian et al. |
| 6,187,054 B1 | 2/2001 | Colone et al. |
| 6,193,745 B1 | 2/2001 | Fogarty et al. |
| 6,196,230 B1 | 3/2001 | Hall et al. |
| 6,197,046 B1 | 3/2001 | Piplani et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,203,569 B1 | 3/2001 | Wijay |
| 6,203,735 B1 | 3/2001 | Edwin et al. |
| 6,203,779 B1 | 3/2001 | Ricci et al. |
| 6,210,422 B1 | 4/2001 | Douglas |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,039 B1 | 4/2001 | Banas et al. |
| 6,217,608 B1 | 4/2001 | Penn et al. |
| 6,221,102 B1 | 4/2001 | Baker et al. |
| 6,224,609 B1 | 5/2001 | Ressemann et al. |
| 6,231,562 B1 | 5/2001 | Khosravi et al. |
| 6,235,050 B1 | 5/2001 | Quiachon et al. |
| 6,235,051 B1 | 5/2001 | Murphy |
| 6,238,432 B1 | 5/2001 | Parodi |
| 6,240,616 B1 | 6/2001 | Yan |
| 6,241,759 B1 | 6/2001 | Piplani et al. |
| 6,245,097 B1 | 6/2001 | Inoue |
| 6,245,099 B1 | 6/2001 | Edwin et al. |
| 6,245,100 B1 | 6/2001 | Davila et al. |
| 6,245,101 B1 | 6/2001 | Drasler et al. |
| 6,245,102 B1 | 6/2001 | Jayaraman |
| 6,248,116 B1 | 6/2001 | Chevillon et al. |
| 6,251,132 B1 | 6/2001 | Ravenscroft et al. |
| 6,251,136 B1 | 6/2001 | Guruwaiya et al. |
| 6,254,593 B1 | 7/2001 | Wilson |
| 6,254,632 B1 | 7/2001 | Wu et al. |
| 6,258,073 B1 | 7/2001 | Mauch |
| 6,258,114 B1 | 7/2001 | Konya et al. |
| 6,258,116 B1 | 7/2001 | Hojeibane |
| 6,261,316 B1 | 7/2001 | Shaolian et al. |
| 6,261,317 B1 | 7/2001 | Inoue |
| 6,264,662 B1 | 7/2001 | Lauterjung |
| 6,264,684 B1 | 7/2001 | Banas et al. |
| 6,267,783 B1 | 7/2001 | Letendre et al. |
| 6,267,834 B1 | 7/2001 | Shannon et al. |
| 6,270,524 B1 | 8/2001 | Kim |
| 6,270,525 B1 | 8/2001 | Letendre et al. |
| 6,270,707 B1 | 8/2001 | Hon et al. |
| 6,273,909 B1 | 8/2001 | Kugler et al. |
| 6,273,910 B1 | 8/2001 | Limon |
| 6,273,911 B1 | 8/2001 | Cox et al. |
| 6,280,457 B1 | 8/2001 | Wallace et al. |
| 6,280,466 B1 | 8/2001 | Kugler et al. |
| 6,280,467 B1 | 8/2001 | Leonhardt et al. |
| 6,283,991 B1 | 9/2001 | Cox et al. |
| 6,287,315 B1 | 9/2001 | Wijeratne et al. |
| 6,287,329 B1 | 9/2001 | Duerig et al. |
| 6,287,330 B1 | 9/2001 | Johansson et al. |
| 6,287,335 B1 | 9/2001 | Drasler et al. |
| 6,287,336 B1 | 9/2001 | Globerman et al. |
| 6,290,728 B1 | 9/2001 | Phelps et al. |
| 6,293,966 B1 | 9/2001 | Frantzen |
| 6,293,968 B1 | 9/2001 | Taheri |
| 6,293,969 B1 | 9/2001 | Chuter |
| 6,296,661 B1 | 10/2001 | Davila et al. |
| 6,302,891 B1 | 10/2001 | Nadal |
| 6,302,905 B1 | 10/2001 | Goldsteen et al. |
| 6,302,906 B1 | 10/2001 | Goicoechea et al. |
| 6,302,908 B1 | 10/2001 | Parodi |
| 6,303,100 B1 | 10/2001 | Ricci et al. |
| 6,306,141 B1 | 10/2001 | Jervis |
| 6,306,145 B1 | 10/2001 | Leschinsky |
| 6,306,164 B1 | 10/2001 | Kujawski |
| 6,306,165 B1 | 10/2001 | Patnaik et al. |
| 6,312,458 B1 | 11/2001 | Golds |
| 6,312,460 B2 | 11/2001 | Drasler et al. |
| 6,312,462 B1 | 11/2001 | McDermott et al. |
| 6,315,791 B1 | 11/2001 | Gingras et al. |
| 6,319,276 B1 | 11/2001 | Holman et al. |
| 6,319,278 B1 | 11/2001 | Quinn |
| 6,319,279 B1 | 11/2001 | Shannon et al. |
| 6,322,587 B1 | 11/2001 | Quiachon et al. |
| 6,325,819 B1 | 12/2001 | Pavcnik et al. |
| 6,325,823 B1 | 12/2001 | Horzewski et al. |
| 6,325,824 B2 | 12/2001 | Limon |
| 6,325,825 B1 | 12/2001 | Kula et al. |
| 6,328,762 B1 | 12/2001 | Anderson et al. |
| 6,331,186 B1 | 12/2001 | Wang et al. |
| 6,331,188 B1 | 12/2001 | Lau et al. |
| 6,331,190 B1 | 12/2001 | Shokoohi et al. |
| 6,331,191 B1 | 12/2001 | Chobotov |
| 6,334,869 B1 | 1/2002 | Leonhardt et al. |
| 6,336,937 B1 | 1/2002 | Vonesh et al. |
| 6,344,044 B1 | 2/2002 | Fulkerson et al. |
| 6,344,054 B1 | 2/2002 | Parodi |
| 6,344,055 B1 | 2/2002 | Shukov |
| 6,346,118 B1 | 2/2002 | Baker et al. |
| 6,346,119 B1 | 2/2002 | Kuwahara et al. |
| 6,348,065 B1 | 2/2002 | Brown et al. |
| 6,350,277 B1 | 2/2002 | Kocur |
| 6,352,553 B1 | 3/2002 | Van der Burg et al. |
| 6,352,561 B1 | 3/2002 | Leopold et al. |
| 6,355,055 B1 | 3/2002 | Waksman et al. |
| 6,355,056 B1 | 3/2002 | Pnheiro |
| 6,355,060 B1 | 3/2002 | Lenker et al. |
| 6,355,063 B1 | 3/2002 | Calcote |
| 6,357,104 B1 | 3/2002 | Myers |
| 6,358,276 B1 | 3/2002 | Edwin et al. |

(56) References Cited

U.S. PATENT DOCUMENTS

| | | |
|---|---|---|
| 6,358,284 B1 | 3/2002 | Fearnot et al. |
| 6,361,637 B2 | 3/2002 | Martin et al. |
| 6,363,938 B2 | 4/2002 | Saadat |
| 6,364,856 B1 | 4/2002 | Ding et al. |
| 6,364,904 B1 | 4/2002 | Smith |
| 6,368,346 B1 | 4/2002 | Jadhav |
| 6,368,347 B1 | 4/2002 | Maini et al. |
| 6,368,355 B1 | 4/2002 | Uflacker |
| 6,371,979 B1 | 4/2002 | Beyar et al. |
| 6,372,136 B1 | 4/2002 | Nakatsuka |
| 6,375,787 B1 | 4/2002 | Lukic |
| 6,379,381 B1 | 4/2002 | Hossainy et al. |
| 6,379,382 B1 | 4/2002 | Yang |
| 6,379,392 B1 | 4/2002 | Walak |
| 6,383,213 B2 | 5/2002 | Wilson et al. |
| 6,383,214 B1 | 5/2002 | Banas et al. |
| 6,387,119 B2 | 5/2002 | Wolf et al. |
| 6,387,124 B1 | 5/2002 | Buscemi et al. |
| 6,391,050 B1 | 5/2002 | Broome |
| 6,391,052 B2 | 5/2002 | Buirge et al. |
| 6,395,019 B2 | 5/2002 | Chobotov |
| 6,395,022 B1 | 5/2002 | Piplani et al. |
| 6,395,208 B1 | 5/2002 | Herweck et al. |
| 6,398,803 B1 | 6/2002 | Layne et al. |
| 6,402,779 B1 | 6/2002 | Colone et al. |
| 6,406,489 B1 | 6/2002 | Richter et al. |
| 6,409,749 B1 | 6/2002 | Maynard |
| 6,409,750 B1 | 6/2002 | Hyodoh |
| 6,409,754 B1 | 6/2002 | Smith et al. |
| 6,409,756 B1 | 6/2002 | Murphy |
| 6,409,757 B1 | 6/2002 | Trout et al. |
| 6,409,761 B1 | 6/2002 | Jang |
| 6,413,269 B1 | 7/2002 | Bui et al. |
| 6,416,535 B1 | 7/2002 | Lazarus |
| 6,416,536 B1 | 7/2002 | Yee |
| 6,416,537 B1 | 7/2002 | Martakos et al. |
| 6,416,538 B1 | 7/2002 | Ley et al. |
| 6,416,539 B1 | 7/2002 | Hassdenteufel |
| 6,416,542 B1 | 7/2002 | Marcade et al. |
| 6,419,701 B1 | 7/2002 | Cook et al. |
| 6,423,084 B1 | 7/2002 | St. Germain |
| 6,423,089 B1 | 7/2002 | Gingras et al. |
| 6,423,090 B1 | 7/2002 | Hancock |
| 6,425,855 B2 | 7/2002 | Tomonto |
| 6,425,898 B1 | 7/2002 | Wilson et al. |
| 6,428,506 B1 | 8/2002 | Simhambhatla et al. |
| 6,428,565 B1 | 8/2002 | Wisselink |
| 6,428,566 B1 | 8/2002 | Holt |
| 6,428,567 B2 | 8/2002 | Wilson et al. |
| 6,428,569 B1 | 8/2002 | Brown |
| 6,428,570 B1 | 8/2002 | Globerman |
| 6,428,571 B1 | 8/2002 | Lentz et al. |
| 6,432,129 B2 | 8/2002 | DiCaprio |
| 6,432,131 B1 | 8/2002 | Ravenscroft |
| 6,432,132 B1 | 8/2002 | Cottone et al. |
| 6,436,104 B2 | 8/2002 | Hoieibane |
| 6,436,133 B1 | 8/2002 | Furst et al. |
| 6,436,134 B2 | 8/2002 | Richter et al. |
| 6,436,135 B1 | 8/2002 | Goldfarb |
| 6,440,165 B1 | 8/2002 | Richter et al. |
| 6,443,941 B1 | 9/2002 | Slepian et al. |
| 6,443,979 B1 | 9/2002 | Stalker et al. |
| 6,443,981 B1 | 9/2002 | Colone et al. |
| 6,447,501 B1 | 9/2002 | Solar et al. |
| 6,447,522 B2 | 9/2002 | Gambale et al. |
| 6,451,047 B2 | 9/2002 | McCrea et al. |
| 6,451,050 B1 | 9/2002 | Rudakov et al. |
| 6,451,051 B2 | 9/2002 | Drasler et al. |
| 6,451,053 B1 | 9/2002 | Dehdashtian et al. |
| 6,454,796 B1 | 9/2002 | Barkman et al. |
| 6,461,381 B2 | 10/2002 | Israel et al. |
| 6,464,720 B2 | 10/2002 | Boatman et al. |
| 6,464,721 B1 | 10/2002 | Marcade et al. |
| 6,464,722 B2 | 10/2002 | Israel et al. |
| 6,471,718 B1 | 10/2002 | Staehle et al. |
| 6,471,720 B1 | 10/2002 | Ehr et al. |
| 6,471,721 B1 | 10/2002 | Dang |
| 6,471,722 B1 | 10/2002 | Inoue |
| 6,475,166 B1 | 11/2002 | Escano |
| 6,475,208 B2 | 11/2002 | Mauch |
| 6,475,236 B1 | 11/2002 | Roubin et al. |
| 6,475,237 B1 | 11/2002 | Drasler |
| 6,475,238 B1 | 11/2002 | Fedida |
| 6,475,466 B1 | 11/2002 | Ricci et al. |
| 6,478,807 B1 | 11/2002 | Foreman et al. |
| 6,478,815 B1 | 11/2002 | Alt |
| 6,478,816 B1 | 11/2002 | Kveen et al. |
| 6,482,227 B1 | 11/2002 | Solovay |
| 6,485,507 B1 | 11/2002 | Walak et al. |
| 6,485,508 B1 | 11/2002 | McGuinness |
| 6,485,509 B2 | 11/2002 | Killion et al. |
| 6,485,511 B2 | 11/2002 | Lau et al. |
| 6,485,513 B1 | 11/2002 | Fan |
| 6,485,515 B2 | 11/2002 | Strecker |
| 6,485,524 B2 | 11/2002 | Strecker |
| 6,488,694 B1 | 12/2002 | Lau et al. |
| 6,488,700 B2 | 12/2002 | Klumb et al. |
| 6,488,701 B1 | 12/2002 | Nolting et al. |
| 6,488,705 B2 | 12/2002 | Schmitt et al. |
| 6,491,718 B1 | 12/2002 | Ahmad |
| 6,491,719 B1 | 12/2002 | Fogary et al. |
| 6,494,875 B1 | 12/2002 | Mauch |
| 6,494,904 B1 | 12/2002 | Love |
| 6,494,907 B1 | 12/2002 | Bulver |
| 6,494,909 B2 | 12/2002 | Greenhalgh |
| 6,497,722 B1 | 12/2002 | Von Oepen et al. |
| 6,497,723 B1 | 12/2002 | Starck et al. |
| 6,500,202 B1 | 12/2002 | Shaolian et al. |
| 6,500,203 B1 | 12/2002 | Thompson et al. |
| 6,500,204 B1 | 12/2002 | Igaki |
| 6,500,532 B1 | 12/2002 | Ruefer et al. |
| 6,503,271 B2 | 1/2003 | Duerig et al. |
| 6,506,211 B1 | 1/2003 | Doran et al. |
| 6,508,833 B2 | 1/2003 | Pavcnik et al. |
| 6,508,834 B1 | 1/2003 | Pinchasik et al. |
| 6,514,281 B1 | 2/2003 | Blaeser et al. |
| 6,517,558 B2 | 2/2003 | Gittings et al. |
| 6,517,571 B1 | 2/2003 | Brauker et al. |
| 6,517,573 B1 | 2/2003 | Pollock et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,520,986 B2 | 2/2003 | Martin et al. |
| 6,524,334 B1 | 2/2003 | Thompson |
| 6,524,335 B1 | 2/2003 | Hartley et al. |
| 6,524,336 B1 | 2/2003 | Papazolgou et al. |
| 6,530,765 B1 | 3/2003 | Zdrahala et al. |
| 6,530,947 B1 | 3/2003 | Euteneuer et al. |
| 6,530,950 B1 | 3/2003 | Alvarado et al. |
| 6,533,806 B1 | 3/2003 | Sullivan et al. |
| 6,533,807 B2 * | 3/2003 | Wolinsky et al. ............ 623/1.15 |
| 6,533,808 B1 | 3/2003 | Thompson et al. |
| 6,533,811 B1 | 3/2003 | Ryan et al. |
| 6,537,202 B1 | 3/2003 | Frantzen |
| 6,540,778 B1 | 4/2003 | Quiachon et al. |
| 6,540,780 B1 | 4/2003 | Zilla et al. |
| 6,547,813 B2 | 4/2003 | Stiger et al. |
| 6,547,814 B2 | 4/2003 | Edwin et al. |
| 6,547,815 B2 | 4/2003 | Myers |
| 6,547,817 B1 | 4/2003 | Fischell et al. |
| 6,548,013 B2 | 4/2003 | Kadavy et al. |
| 6,551,350 B1 | 4/2003 | Thornton et al. |
| 6,554,857 B1 | 4/2003 | Zilla et al. |
| 6,554,858 B2 | 4/2003 | Dereume et al. |
| 6,558,414 B2 | 5/2003 | Layne |
| 6,558,415 B2 | 5/2003 | Thompson |
| 6,562,063 B1 | 5/2003 | Euteneuer et al. |
| 6,565,597 B1 | 5/2003 | Fearnot |
| 6,569,150 B2 | 5/2003 | Teague |
| 6,569,190 B2 | 5/2003 | Whalen, II et al. |
| 6,569,193 B1 | 5/2003 | Cox et al. |
| 6,572,649 B2 | 6/2003 | Berry et al. |
| 6,575,994 B1 | 6/2003 | Marin |
| 6,576,009 B2 | 6/2003 | Ryan et al. |

(56) References Cited

U.S. PATENT DOCUMENTS

| | | |
|---|---|---|
| 6,579,314 B1 | 6/2003 | Lombardi et al. |
| 6,582,458 B1 | 6/2003 | White et al. |
| 6,589,274 B2 | 7/2003 | Stiger et al. |
| 6,589,275 B1 | 7/2003 | Ivancev et al. |
| 6,592,614 B2 | 7/2003 | Lenker et al. |
| 6,602,269 B2 | 8/2003 | Wallace et al. |
| 6,602,280 B2 | 8/2003 | Chobotov |
| 6,602,283 B2 | 8/2003 | Doran et al. |
| 6,605,110 B2 | 8/2003 | Harrison |
| 6,607,551 B1 | 8/2003 | Sullivan et al. |
| 6,613,082 B2 | 9/2003 | Yang |
| 6,613,083 B2 | 9/2003 | Alt |
| 6,613,084 B2 | 9/2003 | Yang |
| 6,620,190 B1 | 9/2003 | Colone |
| 6,626,938 B1 | 9/2003 | Butaric et al. |
| 6,635,079 B2 | 10/2003 | Unsworth et al. |
| 6,645,240 B2 | 11/2003 | Yee |
| 6,652,554 B1 | 11/2003 | Wholey et al. |
| 6,652,570 B2 | 11/2003 | Smith et al. |
| 6,652,573 B2 | 11/2003 | Oepen |
| 6,652,575 B2 | 11/2003 | Wang |
| 6,652,580 B1 | 11/2003 | Chutter |
| 6,656,215 B1 | 12/2003 | Yanez et al. |
| 6,656,506 B1 | 12/2003 | Wu et al. |
| 6,660,030 B2 | 12/2003 | Shaolian et al. |
| 6,663,662 B2 | 12/2003 | Pacetti et al. |
| 6,663,663 B2 | 12/2003 | Kim et al. |
| 6,663,664 B1 | 12/2003 | Pacitti |
| 6,663,665 B2 | 12/2003 | Shaolian et al. |
| 6,663,667 B2 | 12/2003 | Dehdashtian et al. |
| 6,669,720 B1 | 12/2003 | Pierce |
| 6,669,723 B2 | 12/2003 | Killion et al. |
| 6,669,724 B2 | 12/2003 | Park et al. |
| 6,673,102 B1 | 1/2004 | Vonesh et al. |
| 6,673,103 B1 | 1/2004 | Golds et al. |
| 6,673,106 B2 | 1/2004 | Mitelberg et al. |
| 6,673,107 B1 | 1/2004 | Brandt et al. |
| 6,676,667 B2 | 1/2004 | Mareiro et al. |
| 6,676,695 B2 | 1/2004 | Solem |
| 6,679,911 B2 | 1/2004 | Burgermeister |
| 6,685,736 B1 | 2/2004 | White et al. |
| 6,689,158 B1 | 2/2004 | White et al. |
| 6,689,159 B2 | 2/2004 | Hartigan et al. |
| 6,692,523 B2 | 2/2004 | Holman et al. |
| 6,694,983 B2 | 2/2004 | Hall et al. |
| 6,695,833 B1 | 2/2004 | Frantzen |
| 6,695,875 B2 | 2/2004 | Stelter et al. |
| 6,695,877 B2 | 2/2004 | Brucker et al. |
| 6,696,666 B2 | 2/2004 | Merdan et al. |
| 6,699,274 B2 | 3/2004 | Stinson |
| 6,699,277 B1 | 3/2004 | Freidberg et al. |
| 6,702,847 B2 | 3/2004 | DiCarlo |
| 6,702,849 B1 | 3/2004 | Dutta et al. |
| 6,706,064 B1 | 3/2004 | Anson |
| 6,709,449 B2 | 3/2004 | Camrud et al. |
| 6,709,455 B1 | 3/2004 | Chouinard |
| 6,712,827 B2 | 3/2004 | Ellis et al. |
| 6,716,238 B2 | 4/2004 | Elliott |
| 6,716,239 B2 | 4/2004 | Sowinski |
| 6,719,783 B2 | 4/2004 | Lentz et al. |
| 6,726,712 B1 | 4/2004 | Raeder-Devens |
| 6,730,119 B1 | 5/2004 | Smalling |
| 6,733,521 B2 | 5/2004 | Chobotov et al. |
| 6,736,839 B2 | 5/2004 | Cummings |
| 6,740,111 B1 | 5/2004 | Lauterjung |
| 6,740,114 B2 | 5/2004 | Burgermeister |
| 6,740,115 B2 | 5/2004 | Lombardi |
| 6,743,210 B2 | 6/2004 | Hart et al. |
| 6,743,511 B2 | 6/2004 | Dittrich et al. |
| 6,746,890 B2 | 6/2004 | Gupta |
| 6,752,829 B2 | 6/2004 | Kocur et al. |
| 6,755,855 B2 | 6/2004 | Yurek et al. |
| 6,758,858 B2 | 7/2004 | McCrea et al. |
| 6,761,733 B2 | 7/2004 | Chobotov et al. |
| 6,770,086 B1 | 8/2004 | Girton et al. |
| 6,770,087 B2 | 8/2004 | Layne et al. |
| 6,773,453 B2 | 8/2004 | Ravenscroft |
| 6,773,457 B2 | 8/2004 | Ivancev et al. |
| 6,776,604 B1 | 8/2004 | Chobotov et al. |
| 6,776,793 B2 | 8/2004 | Brown et al. |
| 6,786,920 B2 | 9/2004 | Shannon et al. |
| 6,790,227 B2 | 9/2004 | Burgermeister |
| 6,790,230 B2 | 9/2004 | Beyersdorf et al. |
| 6,793,672 B2 | 9/2004 | Khosravi et al. |
| 6,796,999 B2 | 9/2004 | Pinchasik |
| 6,802,849 B2 | 10/2004 | Blaeser et al. |
| 6,802,856 B2 | 10/2004 | Wilson |
| 6,814,753 B2 | 11/2004 | Schmitt |
| 6,818,013 B2 | 11/2004 | Mitelberg et al. |
| 6,821,292 B2 | 11/2004 | Pazienza et al. |
| 6,824,558 B2 | 11/2004 | Parodi |
| 6,827,726 B2 | 12/2004 | Parodi |
| 6,827,731 B2 | 12/2004 | Annstrong et al. |
| 6,827,735 B2 | 12/2004 | Greenbeg |
| 6,827,737 B2 | 12/2004 | Hill et al. |
| 6,833,004 B2 | 12/2004 | Ishil et al. |
| 6,841,213 B2 | 1/2005 | Parsonage et al. |
| 6,843,802 B1 | 1/2005 | Villalobos et al. |
| 6,849,086 B2 | 2/2005 | Cragg |
| 6,858,035 B2 | 2/2005 | Whayne |
| 6,860,900 B2 | 3/2005 | Clerc et al. |
| 6,863,685 B2 | 3/2005 | Davila et al. |
| 6,869,443 B2 | 3/2005 | Buscemi et al. |
| 6,878,160 B2 | 4/2005 | Gilligan et al. |
| 6,878,161 B2 | 4/2005 | Lenker |
| 6,884,260 B2 | 4/2005 | Kugler et al. |
| 6,899,728 B1 | 5/2005 | Phillips et al. |
| 6,918,925 B2 | 7/2005 | Tehrani |
| 6,918,927 B2 | 7/2005 | Bates et al. |
| 6,923,827 B2 | 8/2005 | Campbell et al. |
| 6,926,732 B2 | 8/2005 | Derus et al. |
| 6,929,659 B2 | 8/2005 | Pinchuk |
| 6,929,709 B2 | 8/2005 | Smith |
| 6,939,370 B2 | 9/2005 | Hartley et al. |
| 6,939,374 B2 | 9/2005 | Banik et al. |
| 6,942,689 B2 | 9/2005 | Majercak |
| 6,945,989 B1 | 9/2005 | Betelia et al. |
| 6,945,992 B2 | 9/2005 | Goodson et al. |
| 6,949,120 B2 | 9/2005 | Kveen et al. |
| 6,962,602 B2 | 11/2005 | Vardi et al. |
| 6,962,603 B1 | 11/2005 | Brown |
| 6,964,677 B2 | 11/2005 | Osypka |
| 6,974,471 B2 | 12/2005 | Van Schie et al. |
| 6,974,472 B2 | 12/2005 | Hong et al. |
| 6,981,982 B2 | 1/2006 | Armstrong et al. |
| 6,989,026 B2 | 1/2006 | Richter et al. |
| 6,994,722 B2 | 2/2006 | DiCarlo |
| 6,997,945 B2 | 2/2006 | Germain |
| 6,998,060 B2 | 2/2006 | Tomonto |
| 7,001,407 B2 | 2/2006 | Hansen et al. |
| 7,001,419 B2 | 2/2006 | DiCaprio et al. |
| 7,001,431 B2 | 2/2006 | Bao et al. |
| 7,011,673 B2 | 3/2006 | Fischell et al. |
| 7,011,674 B2 | 3/2006 | Brenneman |
| 7,022,132 B2 | 4/2006 | Kocur |
| 7,022,135 B2 | 4/2006 | Zilla et al. |
| 7,033,389 B2 | 4/2006 | Sherry |
| 7,056,325 B1 | 6/2006 | Makower |
| 7,056,336 B2 | 6/2006 | Armstrong et al. |
| 7,056,412 B2 | 6/2006 | Henderson |
| 7,066,951 B2 | 6/2006 | Chobotov |
| 7,073,504 B2 | 7/2006 | Callister et al. |
| 7,081,129 B2 | 7/2006 | Chobotov |
| 7,081,132 B2 | 7/2006 | Cook |
| 7,083,642 B2 | 8/2006 | Sirhan et al. |
| 7,090,693 B1 | 8/2006 | Chobotov et al. |
| 7,094,255 B2 | 8/2006 | Penn et al. |
| 7,108,715 B2 | 9/2006 | Brown et al. |
| 7,115,140 B2 | 10/2006 | Stoltze et al. |
| 7,125,464 B2 | 10/2006 | Chobotov et al. |
| 7,128,754 B2 | 10/2006 | Bolduc |
| 7,128,755 B2 | 10/2006 | Su et al. |
| 7,147,455 B2 | 12/2006 | Chobotov et al. |
| 7,147,660 B2 | 12/2006 | Chobotov et al. |

(56) References Cited

U.S. PATENT DOCUMENTS

| | | | |
|---|---|---|---|
| 7,147,661 B2 | 12/2006 | Chobotov et al. | |
| 7,150,758 B2 | 12/2006 | Kari et al. | |
| 7,160,318 B2 | 1/2007 | Greenberg et al. | |
| 7,166,125 B1 | 1/2007 | Baker et al. | |
| 7,175,651 B2 | 2/2007 | Kerr | |
| 7,175,652 B2 | 2/2007 | Cook et al. | |
| 7,189,256 B2 | 3/2007 | Smith | |
| 7,192,441 B2 | 3/2007 | Sherry | |
| 7,223,280 B2 | 5/2007 | Anson et al. | |
| 7,226,474 B2 | 6/2007 | Iancea et al. | |
| 7,229,470 B2 | 6/2007 | Brian et al. | |
| 7,232,459 B2 | 6/2007 | Greenberg | |
| 7,244,242 B2 | 7/2007 | Freyman | |
| 7,273,494 B2 | 9/2007 | Rolando et al. | |
| 7,284,399 B1 | 10/2007 | Sisco | |
| 7,294,147 B2 | 11/2007 | Hartley | |
| 7,314,484 B2 | 1/2008 | Deem et al. | |
| 7,318,835 B2 | 1/2008 | Berra | |
| 7,338,518 B2 | 3/2008 | Chobotov | |
| 7,351,256 B2 | 4/2008 | Hojeibane et al. | |
| 7,425,219 B2 | 9/2008 | Quadri | |
| 7,452,374 B2 | 11/2008 | Hain et al. | |
| 7,465,270 B2 | 12/2008 | Li | |
| 7,485,138 B2 | 2/2009 | Fearnot et al. | |
| 7,491,230 B2 | 2/2009 | Holman et al. | |
| 7,491,234 B2 | 2/2009 | Palasis et al. | |
| 7,500,988 B1 | 3/2009 | Butaric et al. | |
| 7,510,571 B2 | 3/2009 | Spiridigliozzi et al. | |
| 7,520,890 B2 | 4/2009 | Phillips | |
| 7,520,895 B2 | 4/2009 | Douglas et al. | |
| 7,530,988 B2 | 5/2009 | Evans et al. | |
| 7,550,004 B2 | 6/2009 | Bahaler et al. | |
| 7,550,005 B2 | 6/2009 | Bates et al. | |
| 7,556,645 B2 | 7/2009 | Lashinski et al. | |
| 7,591,843 B1 | 9/2009 | Escano | |
| 7,597,710 B2 | 10/2009 | Obermiller | |
| 7,766,954 B2 * | 8/2010 | Chobotov et al. | 623/1.13 |
| 7,976,575 B2 | 7/2011 | Hartley | |
| 8,043,356 B2 | 10/2011 | Kolbel et al. | |
| 8,066,755 B2 | 11/2011 | Zacharias et al. | |
| 8,252,036 B2 | 8/2012 | Cartledge et al. | |
| 2001/0014794 A1 | 8/2001 | Moll | |
| 2001/0029349 A1 | 10/2001 | Leschinsky | |
| 2001/0039445 A1 | 11/2001 | Hall et al. | |
| 2001/0041928 A1 | 11/2001 | Pavcnik et al. | |
| 2001/0044652 A1 | 11/2001 | Moore | |
| 2001/0049534 A1 | 12/2001 | Lachat | |
| 2002/0007193 A1 | 1/2002 | Tanner et al. | |
| 2002/0011684 A1 | 1/2002 | Bahar et al. | |
| 2002/0016626 A1 | 2/2002 | DiMatteo et al. | |
| 2002/0019659 A1 | 2/2002 | Goicoechea et al. | |
| 2002/0029051 A1 | 3/2002 | Callister et al. | |
| 2002/0032408 A1 | 3/2002 | Parker et al. | |
| 2002/0035395 A1 | 3/2002 | Sigimoto | |
| 2002/0040236 A1 | 4/2002 | Lau et al. | |
| 2002/0040237 A1 | 4/2002 | Lentz et al. | |
| 2002/0042644 A1 | 4/2002 | Greenhalgh | |
| 2002/0045931 A1 | 4/2002 | Sogard et al. | |
| 2002/0045933 A1 | 4/2002 | Jang | |
| 2002/0045934 A1 | 4/2002 | Jang | |
| 2002/0045935 A1 | 4/2002 | Jang | |
| 2002/0049487 A1 | 4/2002 | Lootz et al. | |
| 2002/0049490 A1 | 4/2002 | Pollock et al. | |
| 2002/0049493 A1 | 4/2002 | Jang | |
| 2002/0052627 A1 | 5/2002 | Boylan et al. | |
| 2002/0052644 A1 | 5/2002 | Shaolin et al. | |
| 2002/0052649 A1 | 5/2002 | Greenhalgh | |
| 2002/0055768 A1 | 5/2002 | Hess et al. | |
| 2002/0065552 A1 | 5/2002 | Jayaraman et al. | |
| 2002/0072792 A1 | 6/2002 | Burgermeister et al. | |
| 2002/0072793 A1 | 6/2002 | Rolando et al. | |
| 2002/0076542 A1 | 6/2002 | Kramer et al. | |
| 2002/0077692 A1 | 6/2002 | Besselink | |
| 2002/0082680 A1 | 6/2002 | Stanley et al. | |
| 2002/0082682 A1 | 6/2002 | Barclay et al. | |
| 2002/0082685 A1 | 6/2002 | Sirhan et al. |
| 2002/0095208 A1 | 7/2002 | Gregorich et al. |
| 2002/0096252 A1 | 7/2002 | Lukic |
| 2002/0107561 A1 | 8/2002 | Pinheiro |
| 2002/0116050 A1 | 8/2002 | Kocur |
| 2002/0120321 A1 | 8/2002 | Gunderson et al. |
| 2002/0120327 A1 | 8/2002 | Cox et al. |
| 2002/0123790 A1 | 9/2002 | White et al. |
| 2002/0123791 A1 | 9/2002 | Harrison |
| 2002/0123796 A1 | 9/2002 | Majercak et al. |
| 2002/0143387 A1 | 10/2002 | Soetikno et al. |
| 2002/0147492 A1 | 10/2002 | Shokoohi et al. |
| 2002/0151953 A1 | 10/2002 | Chobotov et al. |
| 2002/0151956 A1 | 10/2002 | Chobotov et al. |
| 2002/0156522 A1 | 10/2002 | Ryan et al. |
| 2002/0161376 A1 | 10/2002 | Barry et al. |
| 2002/0165603 A1 | 11/2002 | Thornton et al. |
| 2002/0169497 A1 | 11/2002 | Wholey et al. |
| 2002/0183826 A1 | 12/2002 | Dorn et al. |
| 2002/0183827 A1 | 12/2002 | Derus et al. |
| 2002/0188344 A1 | 12/2002 | Bolea et al. |
| 2002/0188346 A1 | 12/2002 | Healy et al. |
| 2002/0188347 A1 | 12/2002 | Mathis |
| 2002/0193867 A1 | 12/2002 | Gladdish, Jr. et al. |
| 2002/0193872 A1 | 12/2002 | Trout et al. |
| 2002/0193873 A1 | 12/2002 | Brucker et al. |
| 2002/0198585 A1 | 12/2002 | Wisselink |
| 2002/0198587 A1 | 12/2002 | Greenberg et al. |
| 2003/0004560 A1 | 1/2003 | Chobotov et al. |
| 2003/0004565 A1 | 1/2003 | Harnek et al. |
| 2003/0009212 A1 | 1/2003 | Kerr |
| 2003/0014075 A1 | 1/2003 | Rosenbluth et al. |
| 2003/0033001 A1 | 2/2003 | Igaki |
| 2003/0040803 A1 | 2/2003 | Rioux et al. |
| 2003/0050684 A1 | 3/2003 | Abrams et al. |
| 2003/0068296 A1 | 4/2003 | Ricci et al. |
| 2003/0074050 A1 | 4/2003 | Kerr |
| 2003/0083736 A1 | 5/2003 | Brown et al. |
| 2003/0088305 A1 | 5/2003 | Van Schie et al. |
| 2003/0097170 A1 | 5/2003 | Friedrich et al. |
| 2003/0116260 A1 | 6/2003 | Chobotov et al. |
| 2003/0120263 A1 | 6/2003 | Ouriel et al. |
| 2003/0120331 A1 | 6/2003 | Chobotov et al. |
| 2003/0125797 A1 | 7/2003 | Chobotov |
| 2003/0135256 A1 | 7/2003 | Gallagher et al. |
| 2003/0135261 A1 | 7/2003 | Kugler et al. |
| 2003/0176912 A1 | 9/2003 | Chuter et al. |
| 2003/0191518 A1 | 10/2003 | Spiridigliozzi et al. |
| 2003/0204236 A1 | 10/2003 | Letort |
| 2003/0204244 A1 | 10/2003 | Stiger |
| 2003/0212449 A1 | 11/2003 | Cox |
| 2003/0220683 A1 | 11/2003 | Minasian |
| 2003/0225453 A1 | 12/2003 | Murch |
| 2004/0024446 A1 | 2/2004 | Smith |
| 2004/0034407 A1 | 2/2004 | Sherry |
| 2004/0044395 A1 | 3/2004 | Nelson |
| 2004/0049212 A1 | 3/2004 | Whayne |
| 2004/0049264 A1 | 3/2004 | Sowinski et al. |
| 2004/0093055 A1 | 5/2004 | Bartorelli et al. |
| 2004/0093064 A1 | 5/2004 | Bosma |
| 2004/0093068 A1 | 5/2004 | Bergen et al. |
| 2004/0093078 A1 | 5/2004 | Moll et al. |
| 2004/0098096 A1 | 5/2004 | Eton |
| 2004/0106974 A1 | 6/2004 | Greenberg et al. |
| 2004/0116997 A1 | 6/2004 | Taylor et al. |
| 2004/0138734 A1 | 7/2004 | Chobotov et al. |
| 2004/0148008 A1 | 7/2004 | Goodson et al. |
| 2004/0162607 A1 | 8/2004 | Masroor |
| 2004/0167614 A1 | 8/2004 | Anson |
| 2004/0176836 A1 | 9/2004 | Chobotov |
| 2004/0210304 A1 | 10/2004 | Seguin et al. |
| 2004/0215213 A1 | 10/2004 | Dolan |
| 2004/0220655 A1 | 11/2004 | Swanson et al. |
| 2004/0220664 A1 | 11/2004 | Chobotov |
| 2004/0254625 A1 | 12/2004 | Stephens |
| 2005/0033406 A1 | 2/2005 | Barnhart et al. |
| 2005/0049674 A1 | 3/2005 | Berra et al. |
| 2005/0049691 A1 | 3/2005 | Mercile et al. |
| 2005/0075715 A1 | 4/2005 | Borges et al. |

(56) References Cited

U.S. PATENT DOCUMENTS

| | | |
|---|---|---|
| 2005/0090804 A1 | 4/2005 | Chobotov et al. |
| 2005/0090901 A1 | 4/2005 | Studer |
| 2005/0154443 A1 | 7/2005 | Linder et al. |
| 2005/0158272 A1 | 7/2005 | Whirley et al. |
| 2005/0171593 A1 | 8/2005 | Whirley et al. |
| 2005/0177222 A1 | 8/2005 | Mead |
| 2005/0222669 A1 | 10/2005 | Purdy |
| 2005/0228484 A1 | 10/2005 | Stephens et al. |
| 2006/0009833 A1 | 1/2006 | Chobotov et al. |
| 2006/0020319 A1 | 1/2006 | Kim |
| 2006/0030921 A1 | 2/2006 | Berra |
| 2006/0079952 A1 | 4/2006 | Kaplan et al. |
| 2006/0136047 A1 | 6/2006 | Obermiller et al. |
| 2006/0149364 A1 | 7/2006 | Walak et al. |
| 2006/0161244 A1 | 7/2006 | Seguin |
| 2006/0178732 A1 | 8/2006 | Chobotov et al. |
| 2006/0186143 A1 | 8/2006 | Argentine |
| 2006/0212112 A1 | 9/2006 | Evans et al. |
| 2006/0224232 A1 | 10/2006 | Chobotov |
| 2006/0233990 A1 | 10/2006 | Humphrey et al. |
| 2006/0233991 A1 | 10/2006 | Humphrey et al. |
| 2006/0287713 A1 | 12/2006 | Douglas et al. |
| 2006/0292206 A1 | 12/2006 | Kim et al. |
| 2007/0012396 A1 | 1/2007 | Chobotov et al. |
| 2007/0016281 A1 | 1/2007 | Melsheimer |
| 2007/0055347 A1 | 3/2007 | Arbeferize |
| 2007/0100427 A1 | 5/2007 | Perouse |
| 2007/0112413 A1 | 5/2007 | Smith |
| 2007/0162106 A1 | 7/2007 | Evans et al. |
| 2007/0167901 A1 | 7/2007 | Herrig et al. |
| 2007/0203571 A1 | 8/2007 | Kaplan et al. |
| 2007/0219627 A1 | 9/2007 | Chu et al. |
| 2007/0239273 A1 | 10/2007 | Allen |
| 2007/0244539 A1 | 10/2007 | Lentz et al. |
| 2007/0276477 A1 | 11/2007 | Lee et al. |
| 2007/0282369 A1 | 12/2007 | Gilson et al. |
| 2008/0015687 A1 | 1/2008 | Lashinski et al. |
| 2008/0027529 A1 | 1/2008 | Hartley et al. |
| 2008/0051705 A1 | 2/2008 | Von Oepen et al. |
| 2008/0058920 A1 | 3/2008 | Kari |
| 2008/0114441 A1 | 5/2008 | Rust |
| 2008/0114442 A1 | 5/2008 | Mitchell et al. |
| 2008/0114443 A1 | 5/2008 | Mitchell |
| 2008/0132995 A1* | 6/2008 | Burgermeister et al. ..... 623/1.15 |
| 2008/0172119 A1 | 7/2008 | Yamasaki et al. |
| 2008/0228255 A1 | 9/2008 | Rust |
| 2009/0005854 A1* | 1/2009 | Huang et al. ................. 623/1.15 |
| 2009/0036971 A1 | 2/2009 | Humphrey et al. |
| 2009/0042796 A1 | 2/2009 | Wallach et al. |
| 2009/0082841 A1 | 3/2009 | Zacharias et al. |
| 2009/0082842 A1 | 3/2009 | Glynn |
| 2009/0082844 A1 | 3/2009 | Chobotov et al. |
| 2009/0082845 A1 | 3/2009 | Chobotov et al. |
| 2009/0082846 A1 | 3/2009 | Chobotov et al. |
| 2009/0082847 A1* | 3/2009 | Zacharias et al. ............ 623/1.15 |
| 2009/0099649 A1 | 4/2009 | Chobotov et al. |
| 2009/0132020 A1 | 5/2009 | Watson |
| 2009/0132026 A1 | 5/2009 | Martin et al. |
| 2009/0171431 A1 | 7/2009 | Swanson et al. |
| 2009/0182406 A1 | 7/2009 | Blaeser et al. |
| 2009/0198267 A1 | 8/2009 | Evans et al. |
| 2009/0287145 A1 | 11/2009 | Cragg et al. |
| 2009/0287290 A1 | 11/2009 | Macaulay et al. |
| 2010/0114290 A1 | 5/2010 | Rasmussen et al. |
| 2010/0161028 A1* | 6/2010 | Chuter et al. ................. 623/1.13 |
| 2010/0211052 A1 | 8/2010 | Brown et al. |
| 2010/0249908 A1 | 9/2010 | Chau et al. |
| 2010/0305686 A1 | 12/2010 | Cragg |
| 2010/0331958 A1 | 12/2010 | Chobotov et al. |
| 2011/0130819 A1 | 6/2011 | Cragg |
| 2011/0130820 A1 | 6/2011 | Cragg |
| 2011/0130824 A1 | 6/2011 | Cragg |
| 2011/0130825 A1 | 6/2011 | Cragg |
| 2011/0130826 A1 | 6/2011 | Cragg |
| 2011/0218609 A1 | 9/2011 | Chobotov et al. |
| 2011/0238160 A1* | 9/2011 | Molony ....................... 623/1.35 |
| 2012/0016457 A1 | 1/2012 | Chobotov et al. |
| 2012/0041543 A1 | 2/2012 | Huang et al. |
| 2012/0130469 A1 | 5/2012 | Cragg |
| 2012/0191174 A1 | 7/2012 | Vinluan et al. |
| 2012/0197384 A1 | 8/2012 | Lee et al. |
| 2013/0090715 A1 | 4/2013 | Chobotov et al. |
| 2013/0268044 A1 | 10/2013 | Parsons et al. |
| 2013/0268048 A1 | 10/2013 | Watson et al. |

FOREIGN PATENT DOCUMENTS

| | | |
|---|---|---|
| EP | 0646365 | 4/1995 |
| EP | 0714641 | 6/1996 |
| EP | 0775472 | 5/1997 |
| EP | 0792627 | 9/1997 |
| EP | 0808613 | 11/1997 |
| EP | 0819411 | 1/1998 |
| EP | 0878175 | 11/1998 |
| EP | 0943302 | 9/1999 |
| EP | 0997115 | 5/2000 |
| EP | 0480667 | 4/2001 |
| EP | 1093772 | 4/2001 |
| EP | A 1138280 | 10/2001 |
| EP | 0808140 | 12/2001 |
| EP | 1163991 | 12/2001 |
| EP | 1212991 | 6/2002 |
| EP | 1266636 | 12/2002 |
| EP | 1380270 | 1/2004 |
| EP | 1415617 | 4/2004 |
| EP | 1 611 867 | 1/2006 |
| EP | 1611867 | 1/2006 |
| EP | 2 158 880 | 3/2010 |
| EP | 2158880 | 3/2010 |
| JP | 49 042773 | 4/1974 |
| JP | 3109404 | 5/1991 |
| JP | 5161665 | 6/1993 |
| JP | 6100054 | 4/1994 |
| JP | 09117511 | 5/1997 |
| JP | 18-126862 | 6/2006 |
| JP | 18-136382 | 6/2006 |
| RU | 1768154 | 10/1992 |
| RU | 1812980 | 4/1993 |
| RU | 2029527 | 2/1995 |
| SU | 1217402 | 3/1986 |
| SU | 1237201 | 6/1986 |
| SU | 1237202 | 6/1986 |
| SU | 1273077 | 11/1986 |
| SU | 1342511 | 10/1987 |
| SU | 1389778 | 4/1988 |
| SU | 1457921 | 2/1989 |
| SU | 1482714 | 5/1989 |
| SU | 1560134 | 4/1990 |
| SU | 1586718 | 8/1990 |
| SU | 1650127 | 5/1991 |
| SU | 1732964 | 5/1992 |
| WO | WO 91/00792 | 1/1991 |
| WO | WO 92/22604 | 12/1992 |
| WO | WO 93/13824 | 7/1993 |
| WO | WO 93/19804 | 10/1993 |
| WO | WO 94/03127 | 2/1994 |
| WO | WO 95/01761 | 1/1995 |
| WO | WO 95/03754 | 2/1995 |
| WO | WO 95/05132 | 2/1995 |
| WO | WO 95/09586 | 4/1995 |
| WO | WO 96/14095 | 5/1996 |
| WO | WO 96/14808 | 5/1996 |
| WO | WO 97/03624 | 2/1997 |
| WO | WO 97/07751 | 3/1997 |
| WO | WO 97/29716 | 8/1997 |
| WO | WO 97/48350 | 12/1997 |
| WO | WO 98/06355 | 2/1998 |
| WO | WO 98/20811 | 5/1998 |
| WO | WO 98/38947 | 9/1998 |
| WO | WO 98/41167 | 9/1998 |
| WO | WO 98/44870 | 10/1998 |
| WO | WO 98/44873 | 10/1998 |
| WO | WO 99/00073 | 1/1999 |
| WO | WO 99/26559 | 6/1999 |

(56) References Cited

FOREIGN PATENT DOCUMENTS

| | | |
|---|---|---|
| WO | WO 99/38455 | 8/1999 |
| WO | WO 99/43378 | 9/1999 |
| WO | WO 99/43379 | 9/1999 |
| WO | WO 00/10487 | 3/2000 |
| WO | WO 00/13613 | 3/2000 |
| WO | WO 00/42947 | 7/2000 |
| WO | WO 00/42948 | 7/2000 |
| WO | WO 00/44808 | 8/2000 |
| WO | WO 00/51522 | 9/2000 |
| WO | WO 00/67675 | 11/2000 |
| WO | WO 00/71179 | 11/2000 |
| WO | WO 01/05331 | 1/2001 |
| WO | WO 01/08599 | 2/2001 |
| WO | WO 01/15633 | 3/2001 |
| WO | WO 01/21108 | 3/2001 |
| WO | WO 01/30270 | 5/2001 |
| WO | WO 01/41675 | 6/2001 |
| WO | WO 01/56500 | 8/2001 |
| WO | WO 01/56504 | 8/2001 |
| WO | WO 01/58384 | 8/2001 |
| WO | WO 01/58387 | 8/2001 |
| WO | WO 01/66037 | 9/2001 |
| WO | WO 01/67993 | 9/2001 |
| WO | WO 01/74270 | 10/2001 |
| WO | WO 01/82836 | 11/2001 |
| WO | WO 02/36332 | 5/2002 |
| WO | WO 02/41804 | 5/2002 |
| WO | WO 02/078569 | 10/2002 |
| WO | WO 02/083038 | 10/2002 |
| WO | WO 02/100454 | 12/2002 |
| WO | WO 03/022180 | 3/2003 |
| WO | WO 03/053287 | 7/2003 |
| WO | WO 03/053288 | 7/2003 |
| WO | WO 03/094795 | 11/2003 |
| WO | WO 03/094799 | 11/2003 |
| WO | WO 2004/002370 | 1/2004 |
| WO | WO 2004/002371 | 1/2004 |
| WO | WO 2004/017866 | 3/2004 |
| WO | WO 2004/078065 | 9/2004 |
| WO | WO 2005/037076 | 4/2005 |
| WO | WO 2005/086942 | 9/2005 |
| WO | WO 2006/107562 | 10/2006 |
| WO | WO 2008/115678 | 9/2008 |
| WO | WO 2009/042796 | 4/2009 |
| WO | WO 2009/086200 | 7/2009 |
| WO | WO 2011/100367 | 8/2011 |
| WO | WO 2012/068175 | 8/2012 |

OTHER PUBLICATIONS

Blum et al. "Abdominal aortic aneurysms: preliminary technical and clinical results with transfemoral placement of endovascular self-expanding stent-grafts" Radiology 198(1):25-31 (1996). ;198(1):25-31 (1996).

Blum et al. "Endoluminal stent-grafts for infrarenal abdominal aortic aneurysms" N Engl J Med 336(1):13-20 (1997). ;336(1):13-20 (1997).

Campbell et al., "Balloon-Artery Interactions During Stent Placement: A Finite Element Analysis Approach to Pressure, Compliance, and Stent Design as Contributors to Vascular Injury"; 1999; American Heart Association; pp. 378-383.

Canero et al., "Optimal stent implantation: three-dimensional evaluation of the mutual position of stent and vessel via intracoronary echocardiography," Computers in Cardiology, 261-264 (Sep. 1999).

Cooley, Denton A., Surgical Treatment of Aortic Aneurysms (Book), W.B. Saunders Company, West Washington Square, PA (1986).

Donayre, et al., "Fillable endovascular aneurysm repair", Endovascular Today, p. 64-66, Jan. 2009.

Dumoulin C. et al., "Mechanical behavior modeling of balloon expandable stents." Journal of Biomechanics, vol. 33, No. 11, pp. 1461-1470 (available online: Sep. 8, 2000).

Elger et al. "The Influence of Shape on the Stresses in Model Abdominal Aortic Aneurysms," Transactions of the ASME 326:326-32 (1996).

Ernst "Current therapy for infrarenal aortic aneurysms" N Engl J Med 336(1):58-60 (1997).

Haimovitch, L. and Patierson, N., "Robust growth is forecast for endovascular repair of AAAs," The BBI Newsletter, vol. 26, No. 5, pp. 113-144, (May 2003).

How et al. "Mechanical Properties of Arteries and Arterial Grafts," Chapter 1 of Cardiovascular Biomaterials Hasting, G.W. (ed.) London; New York: Springer-Verlag, 1992 pp. 1-35.

Lakshmiraghavan, M. Mechanical Wall Stress in Abdominal Aortic Aneurysm: Towards the Development of a Clinical Tool to Predict Aneurysm Rupture. Submitted to the University of Pittsburgh, vol. 59/09-B of Dissertation Abstracts International p. 4948. 285 pages. (1998).

Mandai, S. et al. (1992). "Direct Thrombosis of Aneurysms with Cellulose Acetate Polymer. Part I: Results of Thrombosis in Experimental Aneurysms," J. Neurosurgery 77:497-500.

Mirich et al., "Percutaneously Placed Endovascular Grafts for Aortic Aneurysms: Feasibility Study", Radiology, 170/3:1033-1037 (1989); 1033-1037 (1989).

Moore et al. "Transfemoral endovascular repair of abdominal aortic aneurysm: results of the North American EVT phase 1 trial" J Vasc Surg 23(4):543-553 (1996). ;23(4):543-553 (1996).

Mower et al. "Stress Distributions in Vascular Aneurysms: Factors Affecting Risk of Aneurysm Rupture," J. Surgical Research 55:151-61 (1993).

Parodi "Endovascular repair of abdominal aortic aneurysms and other arterial lesions" J Vasc Surg 21(4):549-557 (1995).;21(4):549-557 (1995).

Parodi et al., "Transfemoral intraluminal graft implantation for abdominal aortic aneurysms," Ann. Vasc. Surg., 5(6):491-499 (1991).

Perry, M. D. and Chang, R. T., "Finite Element Analysis of NI-TI Alloy Stent Deployment," Proceedings of the Second International Conference on SMST, Asilomar Conference Center, Pacific Grove CA. USA (1997).

Rogers et al., "Balloon-Artery Interactions During Stent Placement: A finite element analysis approach to pressure, compliance and stent design as contributors to vascular injury", 1999 American Heart Association pp. 378-383.

Stern et al., "Interactive Definition of Endoluminal Aortic Stent Size and Morphology Based on Virtual Angioscopic Rendering of 3D Magnetic Resonance Angiography (MRA)," Cars. Computer Assisted Radiology and Surgery, Proceedings of the International Symposium on Computer Assisted Radiology and Surgery:176-180 (Jun. 1999).

The AneuRx® Stent Graft System Treatment for AAA brochure, "An Innovative Modular Approach for the Treatment of Abdominal Aortic Aneurysms (AAA)," Medtronic Ave, Inc. 1999.

The AneuRx® Stent Graft Treatment for TAA brochure, "An Endoluminal Solution for the Treatment of Descending Thoracic Aortic Aneurysms," Medtronic, Inc. 1999.

U.S. Appl. No. 10/168,053, filed Jun. 14, 2002, entitled Inflatable Intraluminal Graft, by C. Murch.

Uflacker, R. and Robinson, J., "Endovascular treatment of abdominal aortic aneurysms: a review," Eur. Radial., 11:739-753 (2001).

Verhagen "Latest AAA Innovations: The Rndurant Stent Graft System", Veith Symposium Nov. 17, 2007.

Verhagen, Hence J.M. "Endurant Medtronic Endograft for EVAR: advantages & early experience", Slides from Veith Symposium Presentation Nov. 22, 2008.

Volodos, N.L. et al. (1987). "New Balloon Catheter for Dilating Arteries and Installing Prosthesis During Distal Endoprosthetics With Self-Fixing Synthetic Prosthesis," Thesis of VIII Symposium (Oct. 8-10, 1987), Abstract Only in English, four pages.

Volodos, N.L. et al. (1986) "Self-Fixing Synthetic Prostheisis for Endoprosthesis of Vessels," Vestnik Khigurgii pp. 123-124, Abstract Only in English.

Volodos, N.L. et al. (1989). "Clinical Experience in Use of Self-Fixing Synthetic Prosthesis for Distal and Intraoperative Endoprosthestics of Aora and Iliac Arteries," Theses of lxth All-Union Symposium (Oct. 2-3, 1989), Abstract only in English, four pages.

(56) References Cited

OTHER PUBLICATIONS

Vos, A.F.W. et al., "Endovascular Grafting of Complex Aortic Aneurysms with a modular Side Branch Stent Graft System in a Porcine Model", Eur J Vasc Endovasc Surg, May 2004 vol. 27 492-497.
Web page, "Drug Eluting Stents—Why Use Drug Eluting Stents?;" Polymer Coatings Division; at URL http://www.lombardmedlcal.co.uk/lombard/pcde.why.html; Lombard Medical; printed Feb. 1, 2005.
Whitcher, "Simulation of in vivo loading conditions of nitinol vascular stent structures", 1997, Elsevier Science Ltd., pp. 1005-1011.
Whitcher, F., "A Finite Element Treatment of the In-Vivo Loading Conditions of NITI Ad Vascular Stent and Graft Structures," Proceedings of the Second International Conference on SMST, Asilomar Conference Center, Pacific Grove. CA, USA (1997).
Wisselink, W. et al. (2001). "Clipping of Inferior Mesenteric and Lumbar Arteries via Retroperitoneal Laparo-Endoscopic Approach as a Treatment of Persistent Endoleak" Chapter 18 In Endoleaks and Endotension, Veith, F.J. et al. eds. Marcel Dekker, Inc. pp. 211-220.
Extended European Search Report dated: Dec. 17, 2012 in European Application No. EP 08835032 filed: Oct. 3, 2008.
Extended European Search Report Mailed Jul. 27, 2010 in European Application No. 10005904.7 filed: Apr. 11, 2002 and published as: EP 2221023 on Aug. 25, 2010.
Extended European Search Report Mailed Dec. 16, 2009 in European Application No. 09175398.8 filed: Oct. 15, 2004 and published as: EP 2145607 on Jan. 20, 2010.
Extended European Search Report dated: Apr. 5, 2013 in European Application No. EP 08849544 filed: Nov. 13, 2008.
International Preliminary Report on Patentability mailed on Apr. 15, 2010 for International Application No. PCT/US2008/078846 filed on Oct. 3, 2008 and published as WO/2009/046372 on Apr. 9, 2009.
International Search Report and Written Opinion mailed on Jul. 30, 2009 for International Application No. PCT/US2008/078846 filed on Oct. 3, 2008 and published as WO/2009/046372 on Apr. 9, 2009.
International Preliminary Report on Patentability mailed on Apr. 8, 2010 for International Application No. PCT/US2008/077714 filed on Sep. 25, 2008 and published as WO/2009/042789 on Apr. 2, 2009.
International Search Report and Written Opinion mailed on: May 1, 2009 for International Application No. PCT/US2008/077714 filed on Sep. 25, 2008 and published as WO/2009/042789 on Apr. 2, 2009.
International Preliminary Report on Patentability mailed on May 27, 2010 for International Application No. PCT/US2008/083451 filed on Nov. 13, 2008 and published as WO/2009/064923 on May 22, 2009.
International Search Report and Written Opinion mailed on Jun. 30, 2009 for International Application No. PCT/US2008/083451 filed on Nov. 13, 2008 and published as WO/2009/064923 on May 22, 2009.
International Preliminary Report on Patentability mailed on Apr. 8, 2010 for International Application No. PCT/US2008/077727 filed on Sep. 25, 2008 and published as WO2009/042796 on Apr. 2, 2009.
International Search Report and Written Opinion mailed on Mar. 26, 2009 for International Application No. PCT/US2008/077727 filed on Sep. 25, 2008 and published as WO/2009/042796 on Apr. 2, 2009.
International Preliminary Report on Patentability mailed on Jul. 1, 2010 for International Application No. PCT/US2008/087831 filed on Dec. 19, 2008 and published as WO/2009/086200 on Jul. 9, 2009.
International Search Report and Written Opinion mailed on May 28, 2009 for International Application No. PCT/US2008/087831 filed on Dec. 19, 2008 and published as WO/2009/086200 on Jul. 9, 2009.
International Search Report and Written Opinion mailed on Oct. 31, 2011 for International Application No. PCT/US2011/024248 filed on Feb. 9, 2011 and published as WO/2011/100367 on Aug. 28, 2011.
International Search Report and Written Opinion mailed on Jul. 18, 2013 for International Application No. PCT/US2013/034654 filed on Mar. 29, 2013.
International Search Report and Written Opinion mailed on Jul. 18, 2013 for International Application No. PCT/US2013/034787 filed on Apr. 1, 2013.
Invitation to Pay Additional Fees and Partial Search Report dated: Apr. 25, 2013 for International Application No. PCT/US2011/060873 filed on Nov. 15, 2011 and published as WO/2012/068175 on Aug. 2, 2012.
International Search Report and Written Opinion mailed on Jun. 12, 2012 for International Application No. PCT/US2011/060873 filed on Nov. 15, 2011 and published as WO/2012/068175 on Aug. 2, 2012.
Office Action Response mailed: Jul. 18, 2011 in U.S. Appl. No. 12/245,620, filed Oct. 3, 2008 and published as: US2009/0099649 on Apr. 16, 2009.
Office Action mailed: Jan. 19, 2011 in U.S. Appl. No. 12/245,620, filed Oct. 3, 2008 and published as: US2009/0099649 on Apr. 16, 2009.
Office Action Response mailed: Nov. 12, 2010 in U.S. Appl. No. 12/245,620, filed Oct. 3, 2008 and published as: US2009/0099649 on Apr. 16, 2009.
Office Action mailed: May 14, 2010 in U.S. Appl. No. 12/245,620, filed Oct. 3, 2008 and published as: US2009/0099649 on Apr. 16, 2009.
Office Action Response mailed Oct. 24, 2012 in U.S. Appl. No. 11/861,739, filed Sep. 26, 2007 and published as: US2009/0082841 on Mar. 26, 2009.
Office Action mailed: Apr. 27, 2012 in U.S. Appl. No. 11/861,739, filed Sep. 26, 2007 and published as: US2009/0082841 on Mar. 26, 2009.
Office Action mailed: Sep. 14, 2011 in U.S. Appl. No. 11/861,739, filed Sep. 26, 2007 and published as: US2009/0082841 on Mar. 26, 2009.
Office Action Response mailed Jul. 15, 2011 in U.S. Appl. No. 11/861,739, filed Sep. 26, 2007 and published as: US2009/0082841 on Mar. 26, 2009.
Office Action mailed: Mar. 15, 2011 in U.S. Appl. No. 11/861,739, filed Sep. 26, 2007 and published as: US2009/0082841 on Mar. 26, 2009.
Office Action Response mailed Jan. 26, 2011 in U.S. Appl. No. 11/861,739, filed Sep. 26, 2007 and published as: US2009/0082841 on Mar. 26, 2009.
Office Action mailed: Aug. 26, 2010 in U.S. Appl. No. 11/861,739, filed Sep. 26, 2007 and published as: US2009/0082841 on Mar. 26, 2009.
Office Action Response mailed Jun. 14, 2010 in U.S. Appl. No. 11/861,739, filed Sep. 26, 2007 and published as: US2009/0082841 on Mar. 26, 2009.
Office Action mailed: Jan. 14, 2010 in U.S. Appl. No. 11/861,739, filed Sep. 26, 2007 and published as: US2009/0082841 on Mar. 26, 2009.
Office Action mailed: Jun. 7, 2012 in U.S. Appl. No. 11/861,756, filed Sep. 26, 2007 and published as: US2009/0082842 on Mar. 26, 2009.
Office Action mailed: Apr. 11, 2012 in U.S. Appl. No. 11/861,756, filed Sep. 26, 2007 and published as: US2009/0082842 on Mar. 26, 2009.
Office Action Response mailed: Mar. 20, 2012 in U.S. Appl. No. 11/861,756, filed Sep. 26, 2007 and published as: US2009/0082842 on Mar. 26, 2009.
Office Action mailed: Dec. 7, 2011 in U.S. Appl. No. 11/861,756, filed Sep. 26, 2007 and published as: US2009/0082842 on Mar. 26, 2009.
Office Action Response mailed: Oct. 21, 2011 in U.S. Appl. No. 11/861,756, filed Sep. 26, 2007 and published as: US2009/0082842 on Mar. 26, 2009.
Office Action mailed: Apr. 26, 2011 in U.S. Appl. No. 11/861,756, filed Sep. 26, 2007 and published as: US2009/0082842 on Mar. 26, 2009.
Office Action Response mailed: Apr. 5, 2011 in U.S. Appl. No. 11/861,756, filed Sep. 26, 2007 and published as: US2009/0082842 on Mar. 26, 2009.
Office Action mailed: Oct. 6, 2010 in U.S. Appl. No. 11/861,756, filed Sep. 26, 2007 and published as: US2009/0082842 on Mar. 26, 2009.
Office Action Response mailed: Sep. 1, 2010 in U.S. Appl. No. 11/861,756, filed Sep. 26, 2007 and published as: US2009/0082842 on Mar. 26, 2009.
Office Action mailed: Apr. 1, 2010 in U.S. Appl. No. 11/861,756, filed Sep. 26, 2007 and published as: US2009/0082842 on Mar. 26, 2009.

(56) References Cited

OTHER PUBLICATIONS

Office Action mailed on Jan. 30, 2013 in U.S. Appl. No. 12/747,499, filed on Sep. 7, 2010 and published as: US2010/0331958 on: Dec. 30, 2010.
Office Action Response mailed on Dec. 11, 2012 in U.S. Appl. No. 12/747,499, filed on Sep. 7, 2010 and published as: US2010/0331958 on: Dec. 30, 2010.
Office Action mailed on Jun. 18, 2012 in U.S. Appl. No. 12/747,499, filed on Sep. 7, 2010 and published as: US2010/0331958 on: Dec. 30, 2010.
Office Action Response mailed on May 17, 2012 in U.S. Appl. No. 12/747,499, filed on Sep. 7, 2010 and published as: US2010/0331958 on: Dec. 30, 2010.
Office Action mailed on Nov. 28, 2011 in U.S. Appl. No. 12/747,499, filed on Sep. 7, 2010 and published as: US2010/0331958 on: Dec. 30, 2010.
Office Action mailed: Mar. 13, 2012 in U.S. Appl. No. 11/861,731, filed Sep. 26, 2007 and published as: US2009/0082847 on Mar. 26, 2009.
Office Action Response mailed: Dec. 15, 2011 in U.S. Appl. No. 11/861,731, filed Sep. 26, 2007 and published as: US2009/0082847 on Mar. 26, 2009.
Office Action mailed: Jun. 21, 2011 in U.S. Appl. No. 11/861,731, filed Sep. 26, 2007 and published as: US2009/0082847 on Mar. 26, 2009.
Office Action Response mailed: May 23, 2011 in U.S. Appl. No. 11/861,731, filed Sep. 26, 2007 and published as: US2009/0082847 on Mar. 26, 2009.
Office Action mailed: Nov. 23, 2010 in U.S. Appl. No. 11/861,731, filed Sep. 26, 2007 and published as: US2009/0082847 on Mar. 26, 2009.
Office Action Response mailed on Oct. 12, 2010 in U.S. Appl. No. 11/861,731, filed Sep. 26, 2007 and published as: US2009/0082847 on Mar. 26, 2009.
Office Action mailed: Apr. 14, 2010 in U.S. Appl. No. 11/861,731, filed Sep. 26, 2007 and published as: US2009/0082847 on Mar. 26, 2009.
Office Action Response mailed: Jan. 4, 2010 in U.S. Appl. No. 11/861,731, filed Sep. 26, 2007 and published as: US2009/0082847 on Mar. 26, 2009.
Office Action mailed: Oct. 1, 2009 in U.S. Appl. No. 11/861,731, filed Sep. 26, 2007 and published as: US2009/0082847 on Mar. 26, 2009.
International Search Report and Written Opinion mailed on Jul. 18, 2013 for International Application No. PCT/US2013/034654, filed on Mar. 29, 2013 and published as WO 2013/151896 on Oct. 10, 2013.
International Search Report and Written Opinion mailed on Jul. 18, 2013 for International Application No. PCT/US2013/034787, filed on Apr. 1, 2013 and published as WO 2013/151924 on Oct. 10, 2013.
Office Action mailed on Sep. 18, 2013 in U.S. Appl. No. 11/861,828, filed on Sep. 26, 2007 and published as 2009-0082846 on Mar. 26, 2009.
Office Action Response dated: Jun. 30, 2014 in U.S. Appl. No. 13/297,219, filed Nov. 15, 2011 and published as: US2012/0191174 on: Jul. 26, 2012.
Office Action mailed: Jun. 19, 2014 in U.S. Appl. No. 12/245,620, filed Oct. 3, 2008 and published as: US2009/0099649 on Apr. 16, 2009.
Office Action mailed May 22, 2014 in U.S. Appl. No. 11/861,739, filed Sep. 26, 2007 and published as: US2009/0082841 on Mar. 26, 2009.
Office Action dated: Oct. 1, 2014 in U.S. Appl. No. 13/297,219, filed Nov. 15, 2011 and published as: US2012/0191174 on: Jul. 26, 2012.
Office Action dated: Mar. 28, 2014 in U.S. Appl. No. 13/297,219, filed Nov. 15, 2011 and published as: US2012/0191174 on: Jul. 26, 2012.

* cited by examiner

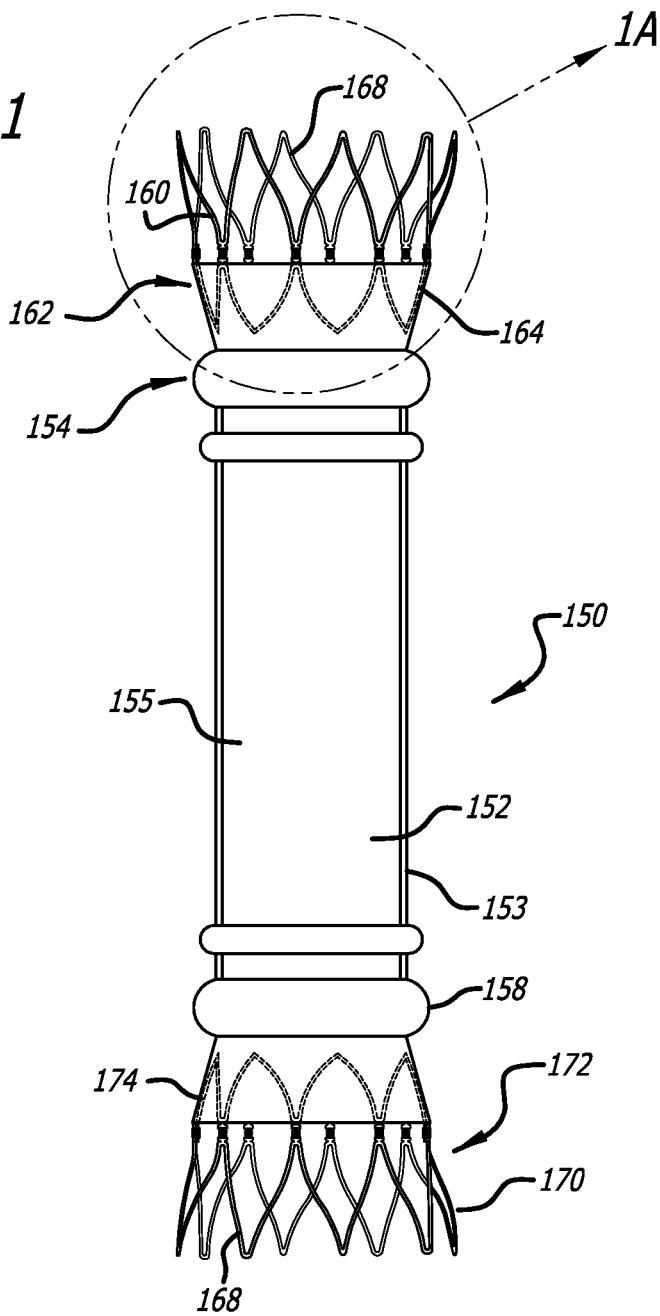

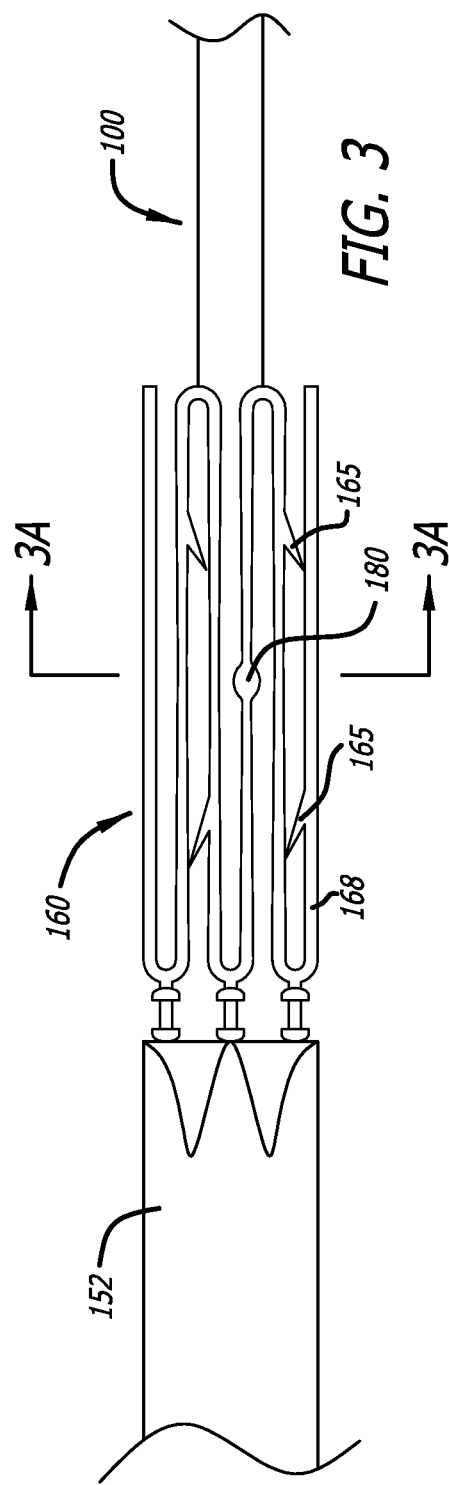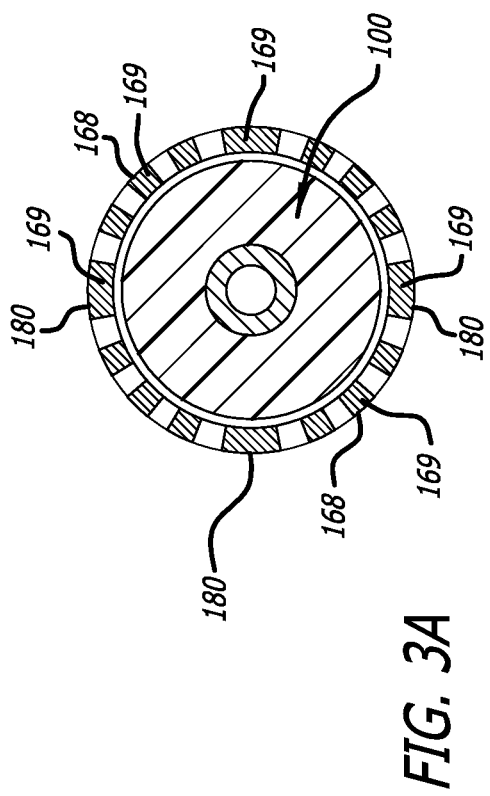

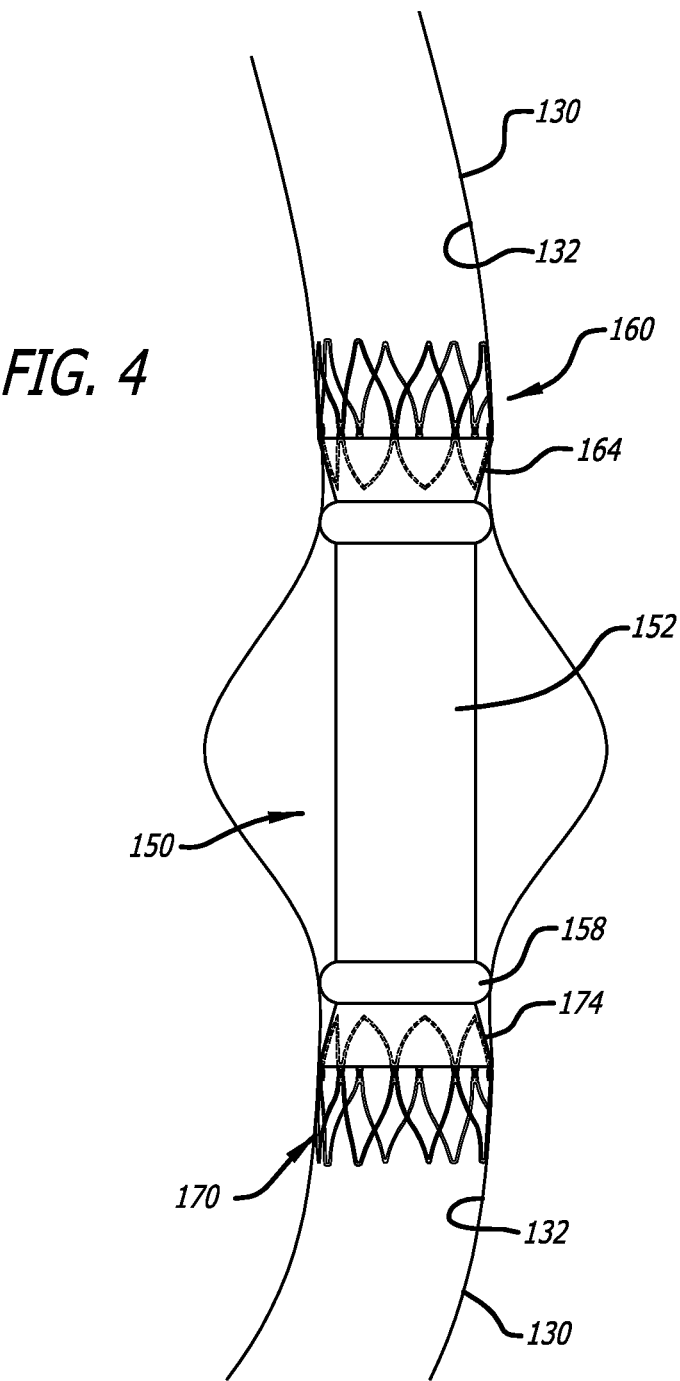

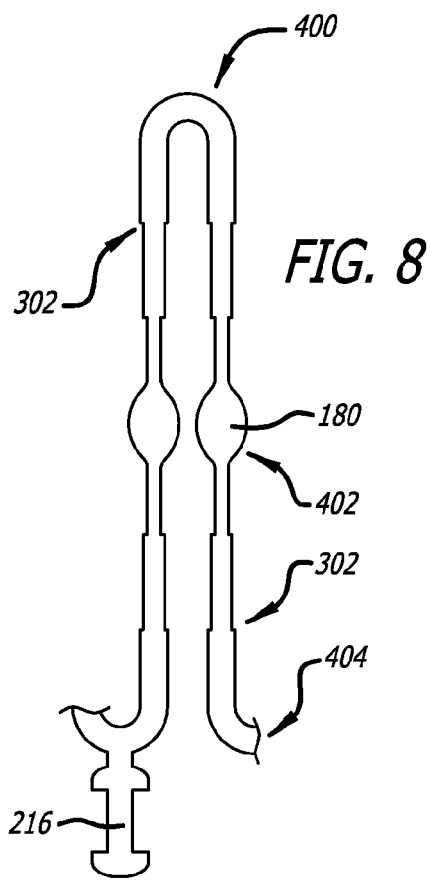
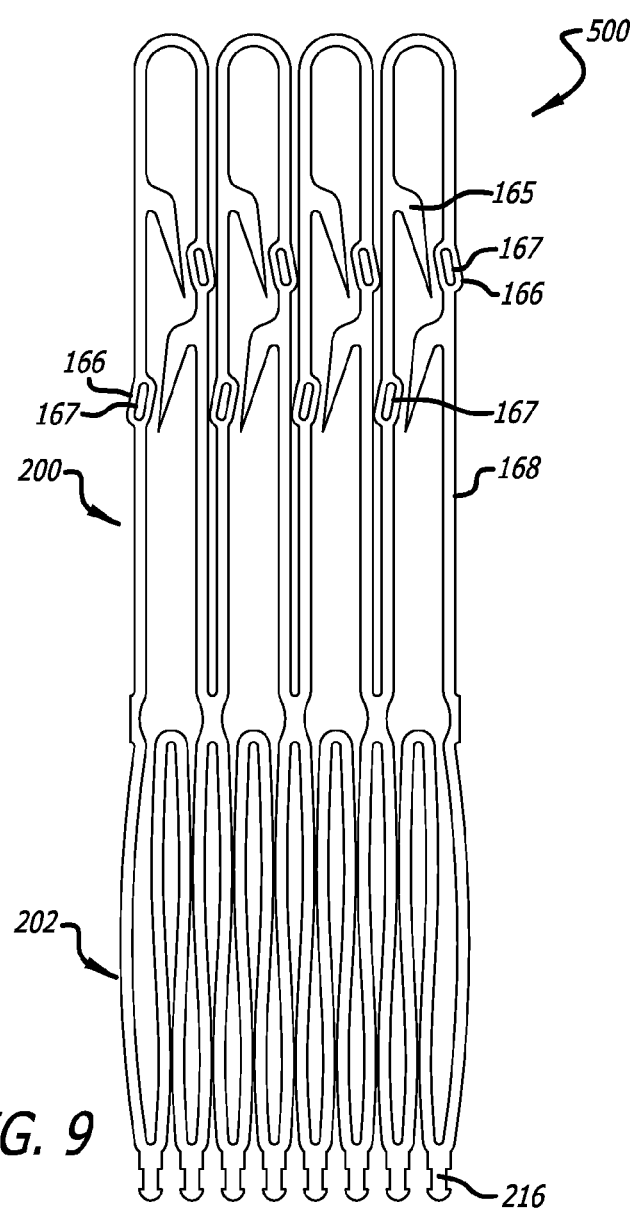
FIG. 8
FIG. 9

DURABLE STENT GRAFT WITH TAPERED STRUTS AND STABLE DELIVERY METHODS AND DEVICES

RELATED APPLICATIONS

This application claims priority under 35 U.S.C. 119(e) from U.S. Provisional Patent Application No. 61/620,362, filed Apr. 4, 2012, by D. Parsons et al., titled Durable Stent Graft with Tapered Struts and Stable Delivery Methods and Devices, which is incorporated by reference herein in its entirety.

FIELD OF THE INVENTION

Some embodiments relate in part to endovascular prostheses and methods of deploying same. Embodiments may be directed more specifically to stent grafts and methods of making and deploying same within the body of a patient.

BACKGROUND

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of a AAA is described in a book titled Surgical Treatment of Aortic Aneurysms by Denton A. Cooley, M.D., published in 1986 by W. B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the AneuRx® stent graft manufactured by Medtronic, Inc. of Minneapolis, Minn., the Zenith® stent graft system sold by Cook, Inc. of Bloomington, Ind., the PowerLink® stent-graft system manufactured by Endologix, Inc. of Irvine, Calif., and the Excluder® stent graft system manufactured by W.L. Gore & Associates, Inc. of Newark, Del. A commercially available stent graft for the treatment of TAAs is the TAG™ system manufactured by W.L. Gore & Associates, Inc.

When deploying devices by catheter or other suitable instrument, it is advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process. In addition, the sizing of stent grafts may be important to achieve a favorable clinical result. In order to properly size a stent graft, the treating facility typically must maintain a large and expensive inventory of stent grafts in order to accommodate the varied sizes of patient vessels due to varied patient sizes and vessel morphologies. Alternatively, intervention may be delayed while awaiting custom size stent grafts to be manufactured and sent to the treating facility. As such, minimally invasive endovascular treatment of aneurysms is not available for many patients that would benefit from such a procedure and can be more difficult to carry out for those patients for whom the procedure is indicated.

What have been needed are stent graft systems and methods that are adaptable to a wide range of patient anatomies and that can be safely and reliably deployed using a flexible low profile system.

SUMMARY

Some embodiments are directed to a self-expanding cylindrical stent which has a constrained state and a relaxed expanded state. The stent may also include a longitudinal axis, a proximal end, a distal end, and a plurality of resilient struts configured to exert an outward radial force in the constrained state. At least one of the resilient struts may include a longitudinal section which is enlarged in a circumferential orientation relative to a longitudinal axis of the stent and configured to stabilize the at least one strut relative to the position of adjacent struts while the stent is in a constrained state. At least some of the enlarged longitudinal sections may be in axial alignment with each other. In some cases, the enlarged longitudinal sections of the struts may be enlarged in one transverse dimension of the struts. In some cases, the enlarged longitudinal sections may be enlarged along a circumferential direction about the longitudinal axis of the stent and the struts may have a substantially constant thickness in a radial direction relative to the longitudinal axis of the stent. The enlarged longitudinal section may have an enlarged transverse dimension that is about 1.5 times to about 3 times the nominal transverse dimension of the strut in a direction of the enlargement for some embodiments.

Certain embodiments are directed to an endovascular stent graft, having a main body portion including at least one tubular portion made from at least one layer of flexible material and a self-expanding cylindrical stent which has a constrained state and a relaxed expanded state. The stent may also include a longitudinal axis, a proximal end, a distal end, a plurality of resilient struts configured to exert an outward radial force in the constrained state. At least one of the resilient struts may include a longitudinal section which is enlarged in a circumferential orientation relative to a longitudinal axis of the stent and configured to stabilize the at least one strut relative to the position of adjacent struts while the stent is in a constrained state. All resilient struts may include a longitudinal section which is enlarged in a circumferential orientation relative to a longitudinal axis of the stent and configured to stabilize at least one strut relative to the position of adjacent struts while the stent is in a constrained state in some embodiments. In some cases, at least some of the enlarged longitudinal sections may be in axial alignment with each other. In some instances, the enlarged longitudinal sections of the struts may be enlarged in one transverse dimension of the struts. In some instances, the enlarged longitudinal sections may be enlarged along a circumferential direction about the longitudinal axis of the stent and the struts may have a substantially constant thickness in a radial direction relative to the longitudinal axis of the stent. The enlarged longitudinal section may have an enlarged transverse dimension that is about 1.5 times to about 3 times the nominal transverse dimension of the strut in a direction of the enlargement in some embodiments.

Some embodiments are directed to a method of loading a delivery catheter system with an endovascular stent graft. The endovascular stent graft may have a main body portion including at least one tubular portion made from at least one layer of flexible material, and a self-expanding cylindrical stent which has a constrained state and a relaxed expanded state. The self-expanding cylindrical stent may include a longitudinal axis, a proximal end, a distal end, a plurality of resilient struts configured to exert an outward radial force in the constrained state. At least one of the resilient struts may include a longitudinal section which is enlarged in a circumferential orientation relative to a longitudinal axis of the stent and configured to separate and stabilize the at least one strut relative to the position of adjacent struts while the stent is in a constrained state. In some cases, the self-expanding cylindrical stent of the stent graft may be constrained about a bushing of the delivery system such that the enlarged longitudinal section of the at least one resilient strut stabilizes the position of the at least one strut relative to the position of adjacent struts in the constrained state. In some instances, the stent may be releasably secured in the constrained stabilized state.

Some embodiments of an endovascular stent graft may include a main body portion having at least one tubular portion made from at least one layer of flexible material and a self-expanding anchor member. The self-expanding anchor member may include a constrained state, a relaxed expanded state, a proximal stent portion, and a distal stent portion. In some cases, the endovascular stent graft may be configured such that a proximal end of the distal stent portion is secured to a distal end of the proximal stent portion and a distal end of the distal stent portion is secured to a proximal end of the main body portion. The endovascular stent graft may also be configured such that the axial length of the self-expanding anchor member as a whole divided by the axial length of the proximal stent portion is a ratio of about 1.75 to about 2.0.

Some embodiments of a self-expanding anchor member include a constrained state, a relaxed expanded state, a proximal stent portion, and a distal stent portion. In some cases, the anchor member may be configured such that a proximal end of the distal stent portion is secured to a distal end of the proximal stent portion and the axial length of the self-expanding anchor member as a whole divided by the axial length of the proximal stent portion is a ratio of about 1.75 to about 2.0.

Some embodiments of an endovascular stent graft may include a main body portion including at least one tubular portion made from at least one layer of flexible material and a self-expanding cylindrical stent which has a constrained state and a relaxed expanded state. The self-expanding cylindrical stent may include a longitudinal axis, a proximal end, a distal end, and a plurality of resilient struts configured to exert an outward radial force in the constrained state. At least one of the resilient struts may have a longitudinal section which is enlarged in a circumferential orientation relative to a longitudinal axis of the stent and be configured to stabilize the at least one strut relative to the position of adjacent struts while the stent is in a constrained state. For such an embodiment, all of the resilient struts of the stent may include a longitudinal section which is enlarged in a circumferential orientation relative to a longitudinal axis of the stent and be configured to stabilize the at least one strut relative to the position of adjacent struts while the stent is in a constrained state. In some cases at least some of the enlarged longitudinal sections may be in axial alignment with each other. In some instances, the enlarged longitudinal sections of the struts may be enlarged in one transverse dimension of the struts or the enlarged longitudinal sections may be enlarged along a circumferential direction about the longitudinal axis of the stent and the struts may have a substantially constant thickness in a radial direction relative to the longitudinal axis of the stent. For some embodiments, the enlarged longitudinal section may have an enlarged transverse dimension that is about 1.5 times to about 3 times the nominal transverse dimension of the strut in a direction of the enlargement. In some cases, the enlarged longitudinal section includes an undulating configuration of the nominal strut or an oval enlargement of the nominal strut. In some instances, each strut of the stent may include an enlarged longitudinal section with only one enlarged longitudinal section or an enlarged longitudinal section with a plurality of enlarged longitudinal sections. For some embodiments, the struts having enlarged longitudinal sections may be disposed in a substantially longitudinal orientation between the proximal end and distal end of the stent when the stent is in the constrained state. In some cases, the struts may be disposed in an undulating pattern. In some instances, the self-expanding cylindrical stent of the stent graft may include a superelastic alloy such as NiTi alloy.

Certain embodiments are described further in the following description, examples, claims and drawings.

BRIEF DESCRIPTION OF THE DRAWINGS

FIG. 1 illustrates an elevation view of an embodiment of an endoluminal prosthesis in the form of a stent graft for treatment of a patient's vessel.

FIG. 3 shows an enlarged view of the encircled portion 3 of the stent graft of FIG. 2 including the proximal self-expanding stent member in a constrained configuration but without the constraining releasable belts for clarity of illustration.

FIG. 3A is a transverse cross sectional view of the proximal self-expanding stent member and delivery catheter system of FIG. 3 taken along lines 3A-3A of FIG. 3.

FIG. 4 illustrates the stent graft of FIG. 2 in a deployed unconstrained state.

FIG. 8 illustrates a portion of an embodiment of a stent including struts having a stepped taper configuration.

FIG. 9 illustrates a portion of an embodiment of a stent including struts having a continuous taper, barbs, and tuck pads with tuck slots.

Figure 1A:
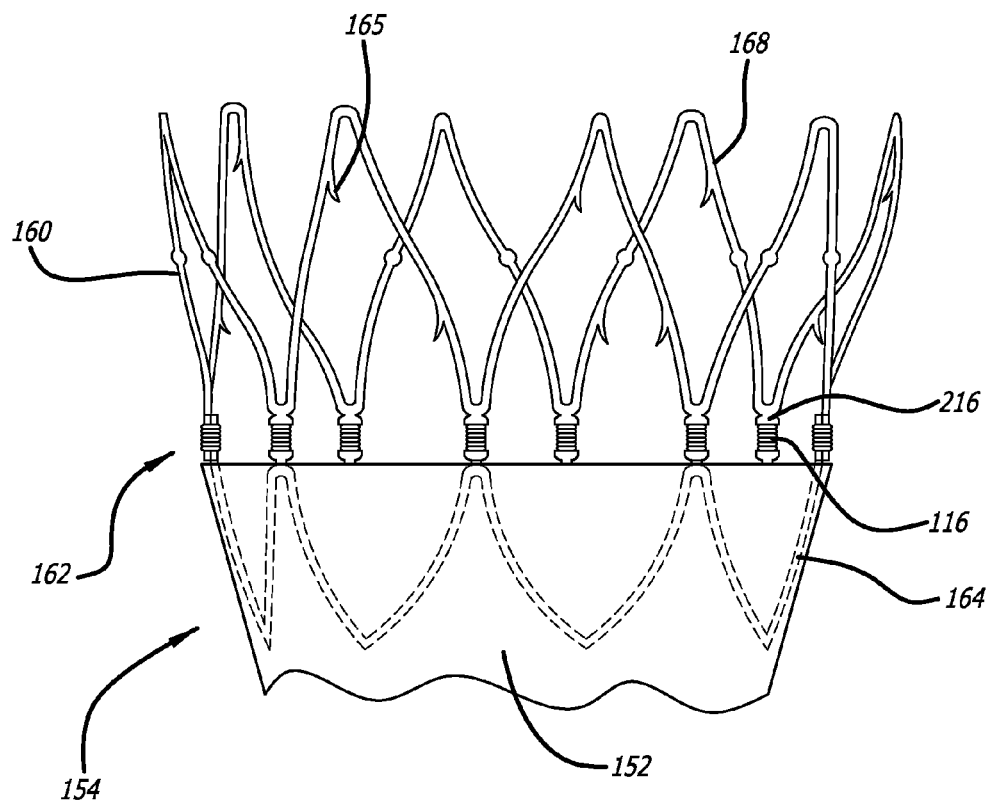
FIG. 1A is an enlarged view of the encircled portion 1A of FIG. 1 including a proximal self-expanding stent member and proximal connector ring of the stent graft embodiment of FIG. 1.

The drawings illustrate embodiments of the invention and are not limiting. For clarity and ease of illustration, the drawings are not made to scale and, in some instances, various aspects may be shown exaggerated or enlarged to facilitate an understanding of particular embodiments.

DETAILED DESCRIPTION

Embodiments of the invention are directed generally to methods and devices for treatment of fluid flow vessels with the body of a patient. Treatment of blood vessels may be specifically indicated for some embodiments, and, more specifically, treatment of aneurysms, such as abdominal aortic aneurysms. Devices for such treatment modalities may include stents, grafts and stent graft assemblies that include at least one stent secured to a graft member.

For some embodiments, the modular graft assembly may be bifurcated for treatment of an abdominal aortic aneurysm. Such a graft assembly embodiment may include a bifurcated main body member, an ipsilateral graft extension and contralateral graft extension. The main body may have a wall portion that binds a main fluid flow lumen disposed therein. An ipsilateral leg of the main body may have an ipsilateral port and an ipsilateral fluid flow lumen that is in fluid communication with the main fluid flow lumen and the ipsilateral port. A contralateral leg of the main body may have a contralateral port and a contralateral fluid flow lumen that is in fluid communication with the main fluid flow lumen and the contralateral port. The main body, ipsilateral leg, and contralateral leg may form a bifurcated "Y" shaped configuration.

For some bifurcated embodiments, the main fluid flow lumen of the main body generally may have a larger transverse dimension and area than a transverse dimension and area of either of the fluid flow lumens of the ipsilateral leg or contralateral leg. A proximal anchor member may be disposed at a proximal end of the main body. The proximal anchor member may include a proximal self-expanding stent that is formed from an elongate element having a generally serpentine shape with four crowns or apices at either end. Each proximal apex or crown of the proximal stent may be coupled to alternating distal crowns or apices of an eight crown distal self-expanding stent. The distal self-expanding stent may be formed from an elongate element having a generally serpentine shape. A distal end of the distal stent may be mechanically coupled to a connector ring which may be embedded in graft material of the proximal end of the main body, or directly coupled to perforations in the proximal edge region of the main body. Embodiments of the connector ring may be generally circular in shape having regular undulations about the circumference that may be substantially sinusoidal in shape. The proximal stent may include outwardly extending barbs, that may be integrally formed with the struts of the stent for some embodiments, having sharp tissue penetrating tips that are configured to penetrate into tissue of an inside surface of a lumen within which the proximal stent is deployed in an expanded state. Although the proximal anchor member may include self-expanding stents, similar stents may be used that are configured to be inelastically expanded with outward radial pressure as might be generated by the expansion of an expandable balloon from within either or both stents. The connector ring coupled to the proximal stent may also be inelastically expandable.

With regard to graft embodiments discussed herein, such as graft assembly, and components thereof, as well as graft extensions and, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

FIGS. 1-4 illustrate an embodiment of a stent graft assembly 150 which may include a main graft member or main body portion 152 which is not bifurcated. The main body 152 may be tubular in shape and have a wall portion 153 that bounds a main fluid flow lumen 155 disposed therein. The main body 152 may include a proximal end 154, a distal end 156 and an inflatable portion 158. The main body 152 of the stent graft assembly 150 may include at least one flexible layer of material such as PTFE, polymer meshes, composites of same or the like. A proximal anchor member or stent may be disposed at the proximal end 154 of the main body 152. The proximal anchor member embodiment shown in FIG. 1 includes a single proximal self-expanding stent member 160 disposed about a proximal end 154 of the main body 152. In some embodiments, the proximal self-expanding stent member 160 may be formed from an elongate element having a generally serpentine shape with eight crowns or apices at either end. A distal end 162 of the proximal self-expanding stent member 160 may be mechanically coupled to a proximal connector ring 164 which may be embedded in graft material generally about the proximal end 154 of the main body 152, or directly coupled to perforations in the proximal end 154 region of the main body 152.

A distal self-expanding stent member 170 may be disposed at the distal end 156 of the main body 152 and may be configured to engage an interior luminal surface 132 within the patient's vasculature 130. The distal self-expanding stent member 170 shown in FIG. 1 includes a single self-expanding stent member disposed along the distal end 156 of the main body 152 of the stent graft assembly 152. The distal self-expanding stent member 170 may be formed from a resilient elongate element having a generally serpentine shape with eight crowns or apices at either end. A proximal end 172 of the distal self-expanding stent member 170 may be mechanically coupled to a distal connector ring 174 which may be embedded in graft material generally about the distal end 156 of the main body 152, or directly coupled to perforations in the distal end 156 region of the main body 152.

Embodiments of either the proximal connector ring 164 or distal connector ring 174 may be generally circular or cylindrical in shape with regular undulations about the circumference that may be substantially sinusoidal or zig-zag in shape. Some embodiments of either the proximal or distal self-expanding stent members 160, 170 may include outwardly extending barbs 165 (see FIG. 1A). Such barbs 165 may be integrally formed with the struts 168 of either the proximal self-expanding stent member 160 or distal self-expanding member 170. Furthermore, the barbs 165 may have sharp tissue penetrating tips that may be configured to penetrate into tissue of an inside surface of a lumen within which either the proximal self-expanding stent member 160 or distal self-expanding member 170 may be deployed into an expanded state.

Although the proximal and distal self-expanding stent members 160 and 170 of the stent graft 150 has generally been described as including self-expanding stents, the proximal and distal self-expanding stent members 160 and 170 may also include similar stents that are configured to be inelastically expanded with outward radial pressure as might be generated by the expansion of an expandable balloon from within either the proximal self-expanding stent member 160 or distal self-expanding stent member 170. Additionally, at least one of the proximal self-expanding stent member 160 and distal self-expanding stent member 170 may be made from or include a superelastic alloy, such as NiTi alloy.

The stent graft 150 may further include an optional inflation conduit (not shown) which may serve as a fill manifold for inflation of the inflatable portion 158 of the stent graft 150. The inflation conduit may include a distal end with an inflation port in fluid communication with an exterior portion of the main body 152 and extending from the distal end 156 into an interior volume of the inflatable portion 158 of the stent graft 150.

Some embodiments of the stent graft 150 may include radiopaque markers 116 that may be used to facilitate alignment of the stent graft 150. A radiopaque marker 116 configuration and imaging system may be used for alignment during positioning of the stent graft 150 in a patient. FIG. 1A illustrates an enlarged view of a portion of the stent graft 150 with portions of the stent graft 150 not shown for clarity of illustration. The stent graft 150 embodiment shown in FIG. 1A illustrates the proximal end 154 of the main body 152, the proximal self-expanding stent member 160, and a plurality of radiopaque markers 116 disposed about a circumference of a distal end 162 of the proximal self-expanding stent member 160. Furthermore, the plurality of radiopaque markers 116 may include helically wound wire members which may be disposed about connector members 216, as shown in FIG. 1A. In general, the connector members 216 may be configured to mechanically couple the proximal self-expanding stent member 160 to the proximal connector ring 164 disposed within the proximal end 154 of the main body 152 of the stent graft 150. Some embodiments of the stent graft 150 may additionally or alternatively include a plurality of radiopaque markers 116 circumferentially disposed about a tubular portion of the endovascular stent graft 150. For example, the radiopaque markers 116 may lie in a plane that is substantially orthogonal or parallel to a longitudinal axis 186 of the tubular main body 152 of the stent graft 150. Additionally, the distal self-expanding member 170 may include one or more radiopaque markers 116.

Furthermore, any number of features may be incorporated into the stent graft 150 which may enable detection of all or part of the stent graft 150 under fluoroscopy or other suitable forms of imaging. For example, in general, the radiopaque markers 116, or other detection features, may be used to facilitate orthogonal orientation of the imaging axis or view. Once a substantially orthogonal view angle is achieved, an accurate axial position of the partially deployed stent graft 150 relative to the patient's vasculature may be achieved, avoiding parallax, ensuring precise placement of the stent graft 150 relative to significant branch vessels or other anatomic reference points. Parallax in some circumstances may cause error in axial placement of the stent graft 150 relative to the intended target site. Accurate positioning may be achieved with axial movement and adjustment of the stent graft 150 by manual manipulation of a proximal portion of the delivery catheter 100.

Figure 2:
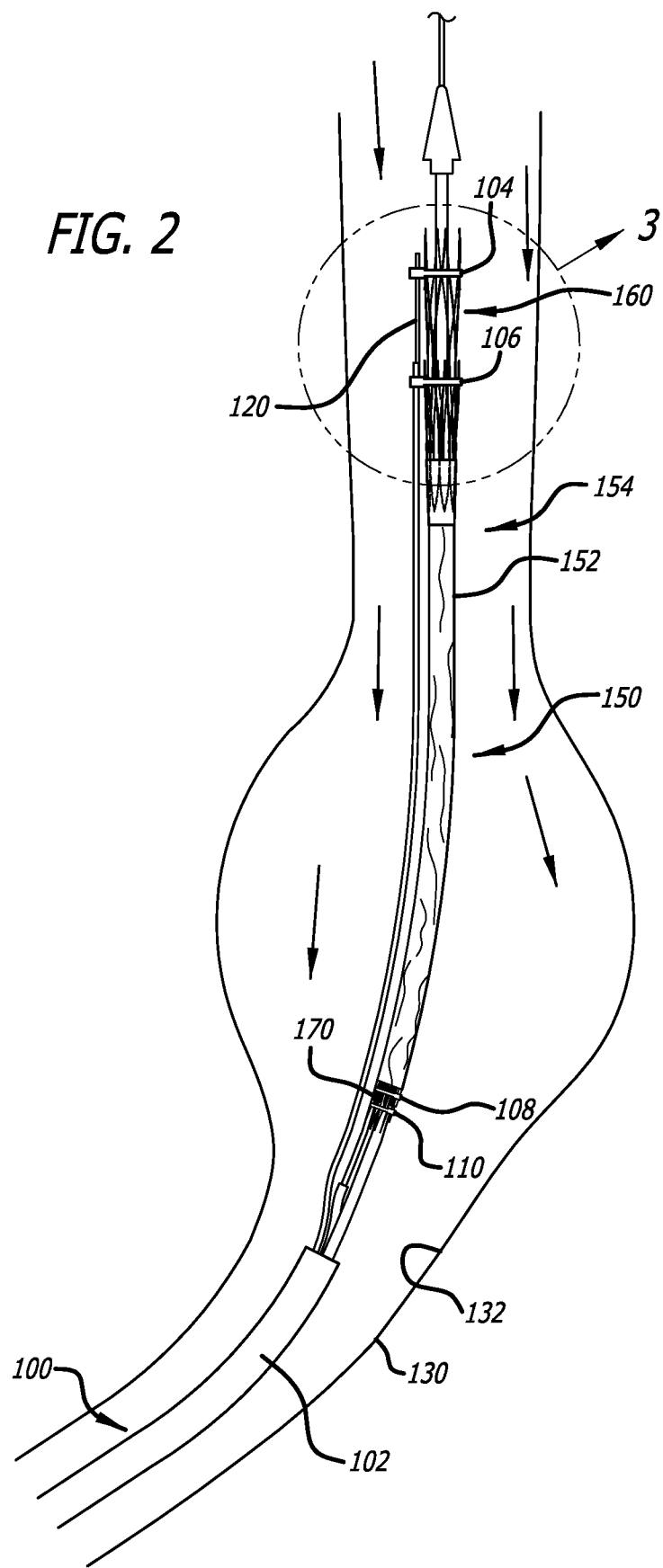
FIG. 2 illustrates the stent graft embodiment of FIG. 1 in a constrained configuration disposed on a distal section of a delivery catheter within a lumen of a patient's vessel.

As shown in FIG. 2, the stent graft 150 may be positioned such that the proximal end 154 of the main body 152 of the stent graft 150 is aligned distal of the ostium of the renal arteries. Once the delivery catheter 100 system has been positioned at the treatment site an outer sheath 102 of the delivery catheter 100 may be proximally retracted. Though the outer sheath 102 may have been proximally retracted, thus exposing the stent graft 150, the stent graft 150 may remain in a partially constrained state with the proximal self-expanding stent member 160 restrained by a pair of proximal releasable belts 104 and 106 releasably disposed about the proximal self-expanding stent member 160. The distal self-expanding stent member 170 may be constrained by another set of distal releasable belts 108 and 110 which may be releasably disposed about the distal self-expanding stent member 170.

Each of the releasable belts 104, 106, 108 and 110 may be configured to be independently released by retraction of one or more respective release wires 120. Release wires 120 may be disposed within an end loop or loops of the releasable belts 104, 106, 108 and 110 with the one or more release wires 120 holding the loops in fixed relation to each other. For this arrangement, retraction of one or more release wires 120 from the end loops releases the loops to allow them to move relative to each other which in turn removes the constraint of the belt members 104, 106, 108 and 110 about the respective proximal and distal self-expanding stent members 160 and 170. After at least partial deployment of the proximal stent member 160, finalizing the axial position of the stent graft 150 relative to the anatomy of the patient's vasculature 130 and treatment site may then be made. The axial positioning may be accomplished in some embodiments with the use of one or more radiopaque marker devices 116, as described above. Once the partially radially constrained stent graft 150 is axially aligned, the proximal self-expanding stent member 160 may then be fully deployed in order to engage and become secured to the luminal wall or interior luminal surface 132 of the patient's vasculature 130, as shown by way of example in FIG. 4. Once the proximal anchor member 160 is fully deployed, the inflatable portion 158 of the stent graft 150, including the network of inflatable channels, may be inflated with a fill material. For some embodiments, the network of inflatable channels may be filled from a desired site within the inflatable portion 158. More specifically, the inflatable portion 158 may be inflated with fill material from a proximal end 154 of the main body 152.

Figure 5:
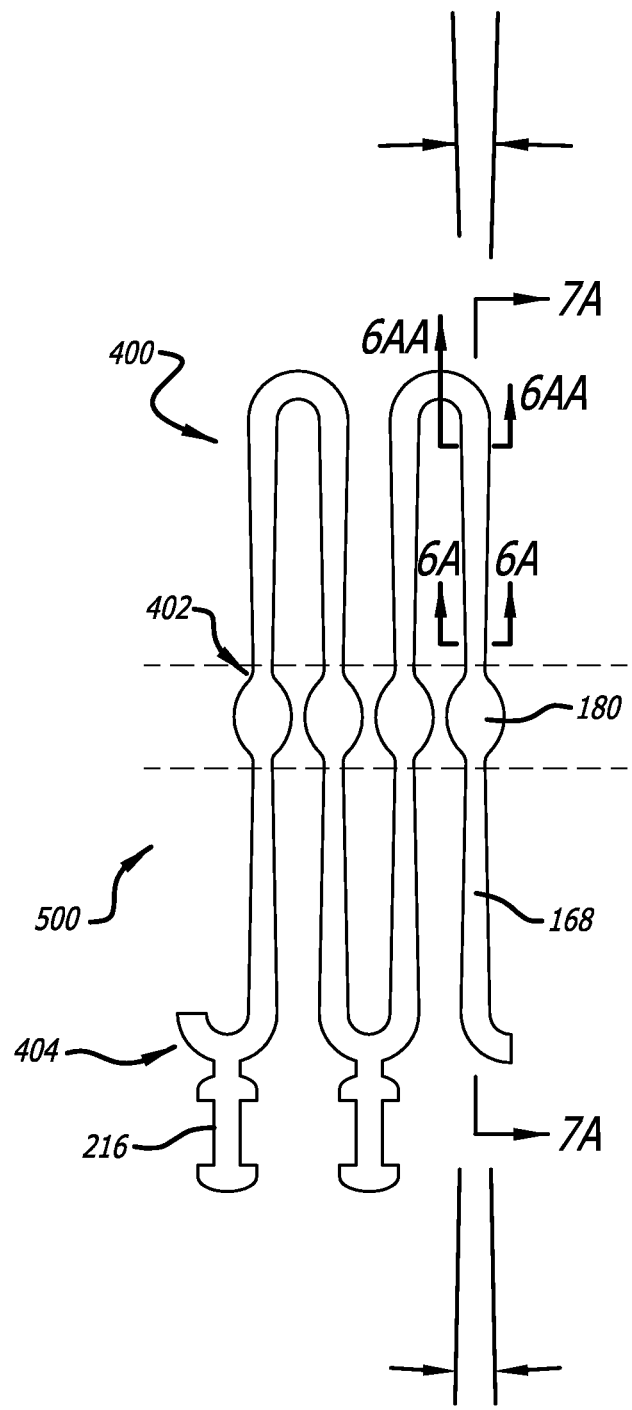
FIG. 5 is a schematic view of an embodiment of a section of a stent that illustrates features of struts of the stent.
Figure 11:
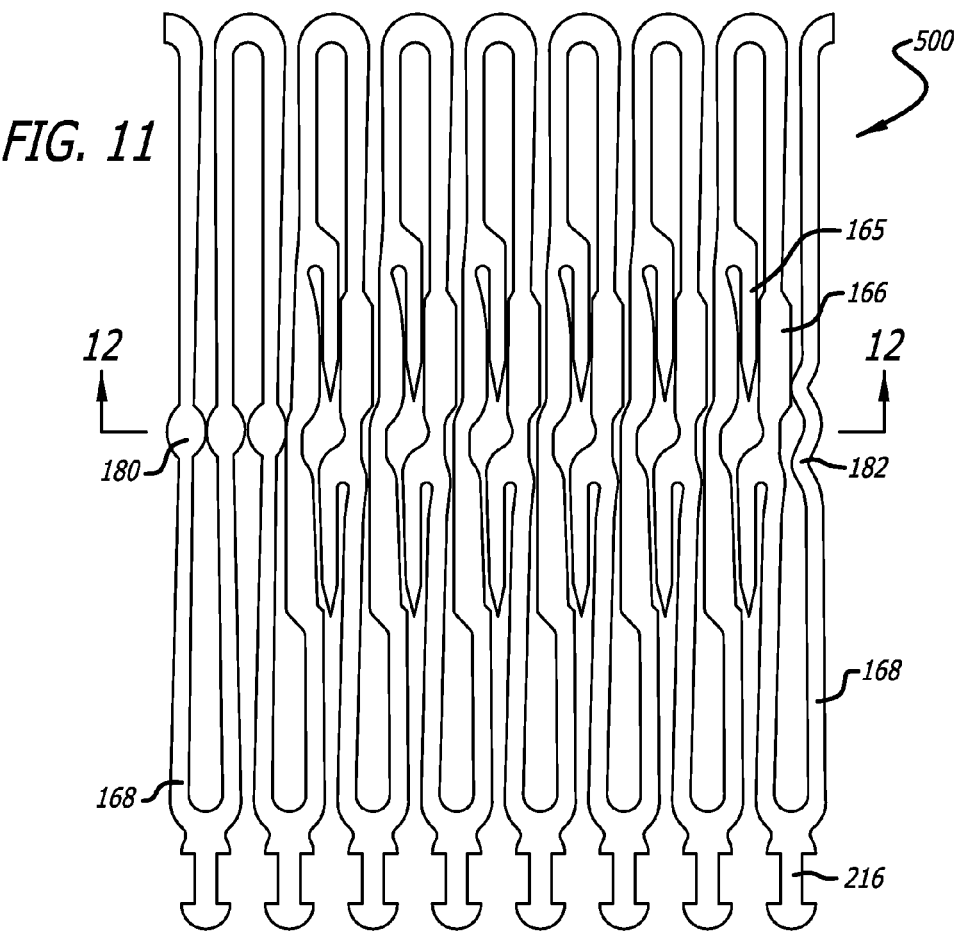
FIG. 11 illustrates a portion of a cylindrical stent embodiment in a constrained configuration shown flattened including struts having coaxial enlarged portion embodiments and undulating deflected portions.

The proximal self-expanding stent member 160 may be disposed at and secured to a proximal end 154 of the main body 152. For example, the proximal self-expanding stent member 160 may have a first self-expanding stent member 200 secured to a second self-expanding stent member 202. Both the first and second self-expanding stent members 200 and 202 may have a somewhat tubular shape and may be secured together by one or more struts 168. Some embodiments of the struts 168 may have one or more cross sectional areas 169 that vary along the length of the strut 168. Such a configuration may be useful in avoiding points of concentrated stress in, for example, the proximal self-expanding stent member 160 or struts 168. The proximal self-expanding stent member 160 may include at least one barb 165 and/or enlarged portion 180 on each strut 168, every other strut 168 or combinations thereof. One proximal self-expanding stent member 160 embodiment may have a repeated strut 168 pattern having a more proximally placed barb 165 on one strut 168, an adjacent neighbor strut 168 with a more distally placed barb 165, and a following adjacent strut 168 with a centrally placed enlarged portion 180, as shown in FIG. 3. Another enlarged portion embodiment 180 may have enlarged portions 180 on every strut 168, as shown in FIG. 5. Additionally, a proximal self-expanding stent member 160 embodiment may have a first self-expanding stent member 200 secured to a second self-expanding stent member 202 where the first self-expanding stent member 200 (or more proximal stent) may have alternating more distally placed barbs 165 along the struts 168 with more proximally placed barbs 165 along the struts 168, as shown in FIG. 9. Another proximal self-expanding stent member 160 embodiment may include one or more struts 168 having enlarged portions 180 generally centrally placed along the length of the struts 168, followed by alternating more distally placed barbs 165 with more proximally placed barbs 165 along the struts 168, as shown in FIG. 11.

For some embodiments, the first self-expanding member 200 of the proximal self-expanding stent member 160 may further include a plurality of barbs 165 having sharp tissue engaging tips that are configured to extend radially outward and distally in a deployed expanded state. This configuration may be useful in order to engage tissue of an inner luminal surface 132 of a patient's vasculature 130 and mechanically anchor the stent graft 150 to the vasculature 130, in addition to the anchoring function provided by the outward radial force of the proximal self-expanding stent member 160 against the inner luminal surface 132 of the patient's vasculature 130 when the stent graft 150 is in a deployed state. The second self-expanding member 202 of the proximal self-expanding stent member 160 may be secured to the proximal end 154 of the main body 152 of the stent graft 150 with one or more struts 168 and/or connector members 216 mechanically coupled to a proximal connector ring 164.

When loaded on the delivery catheter 100, the first and second self-expanding members 200, 202 of the proximal self-expanding stent member 160 may be radially constrained by releasable belts 104 and 106 which may be releasably held in a constraining configuration by a release member, such as a release wire 120. FIG. 2 shows an embodiment of the proximal self-expanding stent member 160 where the first self-expanding member 200 is being radially constrained by a first releasable belt 104 and the second self-expanding member 202 is being radially constrained by a second releasable belt 106. The first releasable belt 104 may be released by a first release wire 120 and the second releasable belt 106 may be deployed by the second release wire 120. The first and second self-expanding members 200 and 202 of the proximal anchor member may only be released after the outer sheath 102 has been retracted, as shown in FIG. 2, in order to expose the stent graft 150.

The strut 168 structure of the proximal self-expanding stent member 160 and/or distal self-expanding stent member 170 may be formed from a cylindrical metal tube structure which is carved or bore by laser or other cutting device. Thereafter, the cut tube may be heat set into two separate forms or states such as an expanded state and non-expanded/contracted state. FIG. 3 shows an example of a non-expanded state. The proximal self-expanding stent member 160 and/or distal self-expanding stent member 170 may include one or more barbs 165. A barb 165 may be any outwardly directed protuberance, typically terminating in a sharp point that is capable of at least partially penetrating a body passageway in which the stent graft 150 is deployed (typically the initial and medial layers of a blood vessel such as the abdominal aorta). The number of barbs 165, the length of each barb 165, each barb 165 angle, and the barb 165 orientation may vary from barb 165 to barb 165 within a single anchor member or between multiple anchor members (i.e., proximal self-expanding stent member 160 and/or distal self-expanding stent member 170) within a single stent graft 150. Although the various barbs 165 (and tuck pads 166, as will be discussed below) may be attached to or fixed on the struts 168, it may be preferred that they are integrally formed as part of the struts 168. When either the proximal self-expanding stent member 160 and/or distal self-expanding stent member 170 is deployed in the abdominal aorta, for example, typically in a location proximal to the aneurysm and any diseased tissue, barbs 165 may be designed to work in conjunction with the distally-oriented blood flow field. In this location, the barbs 165 may penetrate the tissue and prevent axial migration of the stent graft 150. As such, the barbs 165 may be oriented proximally with respect to the main body 152 section. However, the number, dimensions, configuration and orientation of barbs 165 may vary significantly, yet be within the scope of the present invention.

The staged deployment of the proximal self-expanding stent member 160 may also facilitate self-alignment of the stent graft 150. For instance, upon deployment of the proximal self-expanding stent member 160, the graft may be free to expand and enable distal fluid flow to flow through the stent graft 150 and create a "windsock" effect. That is, the distal fluid flow may apply a slight distal force generally upon the main body 152. This distal force may help to align at least the main body 152 and proximal self-expanding stent member 160 within the patient's vasculature 130, which may be particularly advantageous during deployment of the stent graft 150 within the angulated vasculature 130, for example.

In some embodiments of the stent graft 150, one or more struts 168 may include tuck pads 166. Additionally, the one or more struts 168 may have tuck pads 166 positioned such that the tuck pads 166 are generally aligned with a barb 165 extending from an adjacent strut 168, as shown in FIG. 11. As such, during preparation of the stent graft 150 into its reduced diameter delivery configuration (or non-expanded/contracted state), each barb 165 may be placed, for example, behind an adjacent strut 168 and/or tuck pad 166 in order to prevent the barbs 165 from radially extending and contacting the inside of a outer sheath 102 or delivery catheter 100 during delivery of the stent graft 150, as well as to prevent undesired contact of the barbs 165 with the inside luminal surface 132 of a patient's vasculature 130.

As illustrated in FIG. 3A, the struts 168 may have various circumferential dimensions and/or cross sectional areas 169. Enlarged portions 180 of a strut 168 may also include varying radial lengths generally along a longitudinal axis of the strut 168. Enlarged portions 180 may be aligned with barbs 165 and/or located at a generally unstable portion of a strut 168. In some stent graft 150 embodiments, when the stent (i.e., proximal self-expanding member 169) is in a compressed state, enlarged portions 180 may abut each other and may have one or more flat sides which prevent slippage by each other. Adjacent enlarged portions 180 that abut each other and circumferentially interfere with each other may be axially coextensive. In a radially compressed state, for example, the one or more enlarged portions 180 may be compressed to a radial diameter that is no greater than the remaining part of the stent 168.

In some embodiments, one or more struts 168 may have a tapered section 300. For example, one or more struts 168 may have a tapered section 300 in order to evenly distribute strain induced at least when the stent is in a constrained state. The strut 168 may taper from a first end portion of the strut 168 to a smaller transverse cross section towards a middle portion of the strut 168. As shown in FIG. 7B, a strut 168 embodiment may taper from a proximal end 400 portion towards a respective middle portion 402 and taper to a reduced transverse cross section from a distal end portion 404 towards a respective middle portion 402. The strut 168 may taper over half or approximately half of the length of the strut 168. In addition, the strut 168 may taper generally over the entire length of the strut 168, such as from the apex or crown of the anchor member or stent to the middle of the strut or to the first discontinuity feature (i.e., an enlarged portion 180, barb 165, tuck pad 166 and the like). The struts 168 may taper in at least one transverse dimension of the strut 168. Additionally, the struts 168 may taper along a circumferential direction about the longitudinal axis of the struts 168 may have a substantially constant thickness in a radial direction relative to the longitudinal axis of the stent, such as the proximal self-expanding stent member 160. The struts 168 may taper along a radial direction relative to the longitudinal axis of the anchor member or stent and the struts 168 may have a substantially constant thickness in a circumferential direction about the longitudinal axis of the anchor member or stent. The taper angle of a tapered section 300 of a strut 168 may be about 1 degree to about 3 degrees inclusive, about 1.5 degree to about 2.5 degrees inclusive, or about 1.75 degree to about 2.25 degrees inclusive. The strut 168 embodiments may taper continuously from each end portion to the respective middle portions, such as is shown by way of example in FIG. 9. The struts may include a stepped taper embodiment 302 which tapers in discrete steps rather than a smooth continuous taper from the distal and proximal end portions 404 and 400 of the respective middle portions 402 in either radial direction about the longitudinal axis. Such and embodiment is shown by way of example in FIG. 7C. The struts may also taper in a circumferential direction about the longitudinal axis, as shown in FIG. 8. The tapered sections 300 of the struts 168 may extend from proximal and distal end portions 400 and 404 of the struts 168 to respective strut structures (i.e., enlarged portions 180) disposed in, for example, the middle portion 402 of the respective strut 168, as shown by way of example in FIG. 8.

FIG. 5 illustrates a portion of a stent 500 embodiment which may function as a proximal self-expanding stent member 160. The stent 500 may include a plurality of struts 168 extending axially between the proximal end 402 and distal end 404 thereof. The stent 500 may be oriented in either direction, depending on the application. Both the proximal and distal ends 400 and 404 may have a plurality of crowns adjoining adjacent struts 168. The distal end 404 may have a plurality of connecting members 216 configured to connect the stent 500 to the main body 152 or other structure. The stent 500 embodiment may have various features (i.e., tuck pads 166, etc.) and structures and is not limited to the strut 168 features and structures illustrated herein. For example, the stent 500 may have a body defined by a lattice structure or a helical structure.

Optional taper (or tapers) may be incorporated into one or more of the struts 168 of the various stent 500 embodiments, as well as the various connector members 216. In general, incorporating one or more tapers into one or more of the struts 168 in one or more stents 500 may provide greater space in the tapered section 300 to accommodate alternative features such as barbs 165 and tuck pads 166. In addition, it may allow for a smaller deployment profile when the components are in a radially collapsed delivery configuration. When configuring the various stents 500 into this reduced diameter delivery profile (non-expanded/constrained state), the stents 500 may experience a large degree of bending strain that may be poorly distributed. Tapering certain stent 500 struts 168 in particular locations may help to distribute this strain more evenly throughout the stent 500 and/or strut 168 which may assist in preventing strain damage to the stent 500.

Figure 6A:
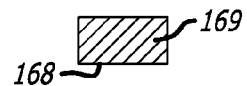
FIGS. 6A and 6AA illustrate paired transverse cross section views of a strut embodiment of FIG. 5 taken along the lines 6A-6A and 6AA-6AA of FIG. 5.
Figure 6A:
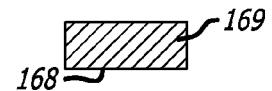

FIG. 5 illustrates a section of a stent 500, such as a proximal self-expanding stent member 160, in which the struts 168 taper from a proximal end 400 width to a minimum width about the middle portion 402 of the strut 168. An example transverse cross-section of the strut 168 taken along line 6AA-6AA, which is generally located in the proximal end 400 region of a strut 168, of FIG. 5 is shown in FIG. 6AA (which may or may not equal a width of strut 168 in the apex region or distal end 404). Another example transverse cross-section of the strut 168 taken along line 6A-6A, which is generally located in the minimum width, or near the middle portion 402 region of the strut 168, of FIG. 5 is shown in FIG. 6A. The optional taper, which may be expressed as the taper ratio, is the ratio of the maximum width (as shown, for example, in FIG. 6AA) to the minimum width (as shown in FIG. 6A) of a cross sectional area 169. The taper ratio may vary widely depending on, for example, the particular region of the strut 168 or connector member 216, the material used, and other factors. Taper ratios ranging from about 1 to about 10 or greater may be within the scope of the present invention. It may also be within the scope of the present invention for the struts 168 to have no taper (as shown by way of example in FIG. 7A).

Figure 6B:
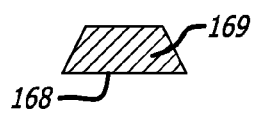
FIGS. 6B and 6BB illustrate paired transverse cross section views of another strut embodiment of FIG. 5.
Figure 6B:
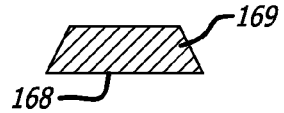
Figure 6C:
FIGS. 6C and 6CC illustrate paired transverse cross section views of another strut embodiment of FIG. 5.
Figure 6C:
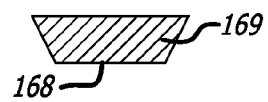
Figure 6D:
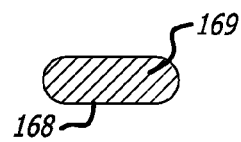
FIGS. 6D and 6DD illustrate paired transverse cross section views of another strut embodiment of FIG. 5.
Figure 6D:
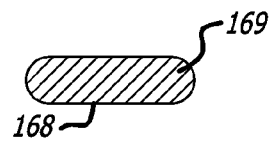
Figure 6E:
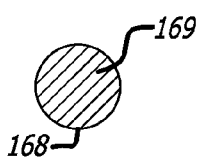
FIGS. 6E and 6EE illustrate paired transverse cross section views of another strut embodiment of FIG. 5.
Figure 6E:
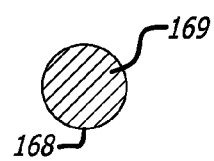

FIGS. 6A-6EE, illustrate a variety of examples of varying transverse cross-sectional views taken at two different locations along a single strut 168. These figures illustrate examples of the different shapes and sizes a single cross sectional area 169 of a strut 168 may have. For instance, as described above, FIGS. 6A and 6AA show a pair of transverse cross section views of the strut 168 embodiment of FIG. 5 taken along the lines 6A-6A and 6AA-6AA which illustrates the rectangular shape of the cross sectional area 169 and the change in size of the cross sectional area 169 at two different locations along the strut 168. FIGS. 6B and 6BB illustrate another example embodiment of paired transverse cross section views of another strut 168 embodiment which illustrates the trapezoidal shape of the cross sectional area 169 and the change in size of the cross sectional area 169 at two different locations along the strut 168. FIGS. 6C and 6CC illustrate another example embodiment of paired transverse cross section views of another strut 168 embodiment which illustrates the inverse trapezoidal shape of the cross sectional area 169 and the change in size of the cross sectional area 169 at two different locations along the strut 168. FIGS. 6D and 6DD illustrate another example embodiment of paired transverse cross section views of another strut 168 embodiment which illustrates the elliptical shape of the cross sectional area 169 and the change in size of the cross sectional area 169 at two different locations along the strut 168. FIGS. 6E and 6EE illustrate another example embodiment of paired transverse cross section views of another strut 168 embodiment which illustrates the circular shape of the cross sectional area 169 and the change in size of the cross sectional area 169 at two different locations along the strut 168. The transverse cross sectional area 169 of one or more locations along a strut 168 are not limited to the sizes and shapes disclosed herein, and may be any number of sizes and shapes that may be incorporated in a strut 168 and/or stent 500 configuration.

A proximal self-expanding stent member 160 may have, for example, one or more struts 168 having a proximal end 400 portion and/or distal end 404 portion which may be made from NiTi and an effective maximum strut 168 width ranging from about 0.016 to about 0.032 inch; particularly from about 0.022 inch and about 0.028 inch, and a minimum strut 168 width between about 0.010 inch and about 0.026 inch; particularly from about 0.012 inch and about 0.022 inch. Additional tapered strut 168 embodiments are described and shown herein in the figures which may be used in other anchor members (such as the proximal and distal self-expanding stent members 160 and 170), stent 500 embodiments or connector members 216 described herein, and may be incorporated in any number of components and made from any number of materials. For example, tapering of the struts 168 in any configuration described herein may improve the strain distribution at least between the proximal end 400 portions and distal end 404 portions of the struts 168.

Various types of taper features or configurations may be implemented in any number of struts 168 for achieving a variety of strut 168 characteristics. For example, one or more struts 168 may include a taper having an offset radii and/or combinations of elliptical and/or circular apex radii in order to further cause the desired behavior during assembly into a reduced-diameter delivery configuration as well as effective delivery and performance in vivo. For example, the proximal end 400 portion, or apex, width may be the minimum width of the strut 168 which untapers towards the middle portion 402 of the strut 168, which may have the maximum width of the strut 168. The tapering from the proximal end 400 portion to the middle portion 402 of the strut 168 may be continuous, stepped in discrete steps 410 with straight untapered portions between each discrete step (as shown by way of example in FIGS. 7C and 8) or a combination thereof. Furthermore, untapering of the strut 168 may be in the radial and/or circumferential direction along the longitudinal length of the strut 168.

The strut 168 may include an enlarged portion 180 located in about the middle portion 402 of one or more of the struts 168, as shown by way of example in FIG. 5. By way of further example, one or more enlarged portions 180 may be located along every other strut 168 of the stent 500. The one or more enlarged portion 180 may be located along a strut 168 in various locations, such as near or at the proximal end 400 portion, middle portion 402, and/or distal end 404 portion of the strut 168. Additionally, the one or more enlarged portions 180 may be located at offset locations relative to enlarged portions 180 (or other features) along neighboring struts 168.

In some cases, the one or more enlarged longitudinal sections or enlarged portions 180 may have an enlarged transverse dimension that is about 1.5 times to about 3 times the nominal transverse dimension of the strut 168 in a direction of the enlargement. Additionally, the enlarged portions 180 may have an undulating configuration of the nominal strut 168. Furthermore, the enlarged portion 180 may have an oval enlargement of the nominal strut. Each strut 168 of the stent 500 having an enlarged portion 168 along the length of the strut 168 may have only one enlarged portion 180. Alternatively, each strut 168 of the stent 500 having an enlarged portion 180 along the length of the strut 168 may have more than one enlarged portion 180. The enlarged portions 180 are not limited to what are described and shown herein, and may be sized, featured, shaped, and proportioned in any number of ways that may assist in assembly or use of the stent 500. Additionally, any number of materials may be used and may vary between struts 168, anchor members (such as the proximal and distal self-expanding strut members 160 and 170), and/or stents 500.

Figure 10A:
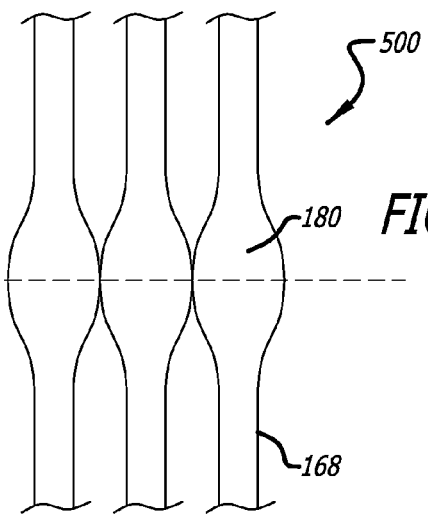
FIG. 10A illustrates a portion of a cylindrical stent embodiment in a constrained configuration including struts having coaxial enlarged portion embodiments.
Figure 10B:
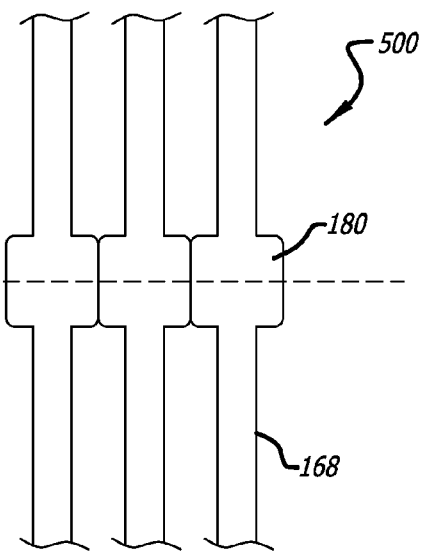
FIG. 10B illustrates a portion of a cylindrical stent embodiment in a constrained configuration including struts having coaxial enlarged portion embodiments.
Figure 10C:
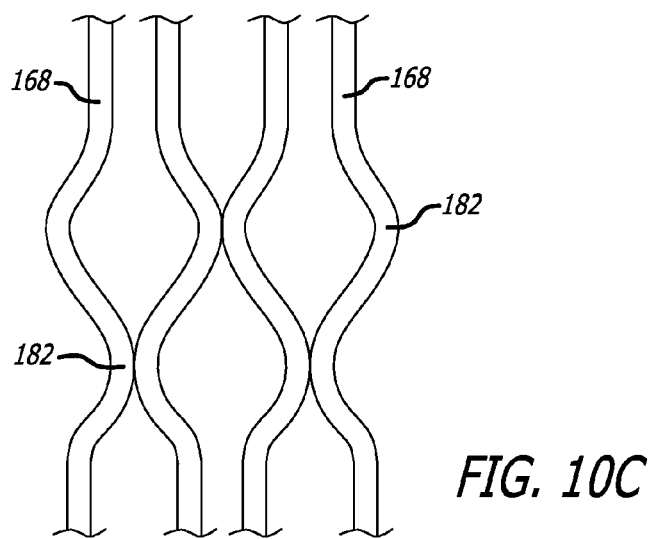
FIG. 10C illustrates a portion of a cylindrical stent embodiment in a constrained configuration including struts having undulating deflected portions configured to physically separate adjacent struts in a circumferential direction.

FIG. 10A shows an example portion of a cylindrical stent embodiment 500 in a constrained configuration including struts 168 having generally coaxially aligned enlarged portion 180 embodiments having circular or oval features. FIG. 10B shows an example portion of a cylindrical stent embodiment 500 in a constrained configuration having struts 168 with generally coaxially aligned enlarged portion 180 embodiments having square or rectangular features. FIG. 10C shows a portion of a cylindrical stent embodiment 500 in a constrained configuration including struts 168 having undulating deflected portions 182 which may be configured to physically separate adjacent struts 168 in a circumferential direction.

One or more struts 168 of a stent embodiment 500 may have a stepped taper 302 feature generally along the length of the strut 168. For example, one or more struts 168 may have a stepped taper 302 from the proximal end 400 to the respective middle portion 402 of the strut 168 and/or a stepped taper 302 from the distal end 404 to the middle portion 402 of the strut 168, wherein the stepped taper 302 may be in either radial direction about the longitudinal axis of the strut 168, as shown by way of example in FIG. 7C, or the circumferential direction about the longitudinal axis, as shown by way of example in FIG. 8. The taper characteristics of a strut 168 may be continuous, stepped or any other shape configured to evenly distribute strain induced by the constraint of the constrained non-expanded stent 500.

Figure 7A:
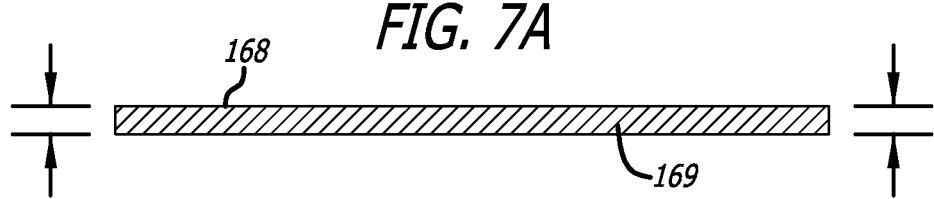
FIG. 7A illustrates a strut embodiment in longitudinal section taken along lines 7A-7A of the stent embodiment in FIG. 5.
Figure 7B:
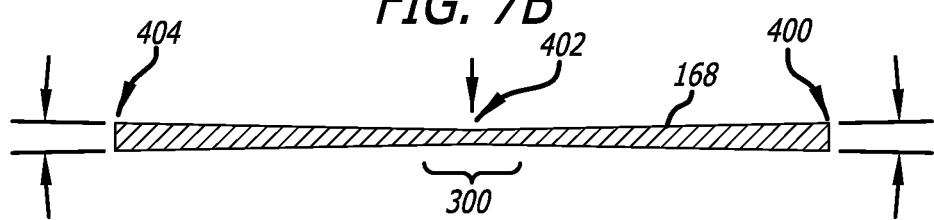
FIG. 7B illustrates another strut embodiment in longitudinal section.
Figure 7C:
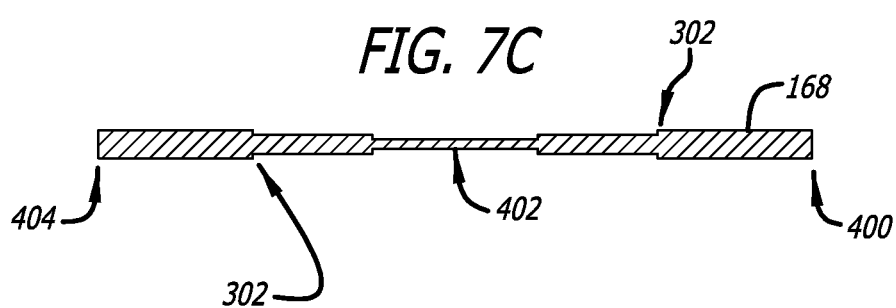
FIG. 7C illustrates another strut embodiment in longitudinal section.

FIG. 7A illustrates an example longitudinal section view taken along line 7A-7A of the strut 168 in FIG. 5 which shows a generally rectangular cross sectional area 169 having no radial tapering about the longitudinal axis. FIG. 7B illustrates another example of a longitudinal section view of a strut 168 which shows a generally tapered cross sectional area 169 due to radial tapering about the longitudinal axis of the strut 168. In FIG. 7B, the strut 168 tapers continuously from each end portion (the proximal and distal ends 400 and 404) to the middle portion 402 such that the middle portion 402 generally has the minimum strut 168 width in the radial direction. FIG. 7C shows another example strut 168 embodiment in longitudinal section including a radial stepped tapering 302 about the longitudinal axis of the strut 168. In FIG. 7C, the strut 168 generally tapers in steps continuously from each end portion (the proximal and distal ends 400 and 404) to the middle portion 402 such that the middle portion 402 generally has the minimum strut 168 width in the radial direction.

FIG. 8 shows a portion of an embodiment of a stent 500 including struts 168 having a circumferential stepped taper 302 configuration about the longitudinal axis of the strut 168. The middle portion 402 of each strut 168 may also include an enlarged portion 180 extending, for example, in a circumferential direction. Portions of the stepped taper 302 of a strut 168 that may be directly adjacent an enlarged portion 180 may have the minimum strut 168 width in the circumferential direction. However, any number of combinations of tapering in any direction may be used.

FIG. 9 shows a stent embodiment 500 where the proximal self-expanding stent member 160 has a first self-expanding member 200 secured to a second self-expanding member 202 where the first self-expanding member 200 has alternating more proximally placed barbs 165 along the struts 168 with more distally placed barbs 165 along the struts 168. In addition, the stent embodiment 500 may have a continuous taper in the second self-expanding member 202, which is the portion of the proximal self-expanding stent member 160 adjacent the main body 152. Each strut 168 on the first self-expanding member 168 may have a barb 165 in a different location relative to a neighboring strut 168. The barbs 165 may be formed integrally with the struts 168, but may otherwise be manufactured, for example, as a separate component attached to the struts 168. In general, the struts 168 and the barbs 165 of the stent embodiments 500 and anchor members may be self-expanding, that is, upon release of a constraining force, the struts 168 may move radially apart and the barbs 165 may extend radially outward. Other configurations, such as balloon expansion, are also contemplated within the present invention.

In addition, stent embodiments 500 may include struts 168 including tuck pads 166, which may be positioned along a strut 168 such that the tuck pads 166 are axially aligned with a barb 165 positioned on a neighboring strut 168. Similar to the barbs 165 and enlarged portions 180, the number, dimensions, configurations and orientations of the tuck pads 166 may vary between struts 168, stent embodiments 500 and anchor members (such as the proximal and distal self-expanding stent members 160 and 170 described herein).

During preparation of a stent graft embodiment 150 (and therefore one or more proximal self-expanding stent members 160) into a reduced diameter delivery configuration, one or more barbs 165 may be placed behind a corresponding strut 168 and/or tuck pad 166, if present, in order to prevent the barbs 165 from contacting the inside of a outer sheath 102 or delivery catheter 100 during delivery of the stent graft 150 and from undesired contact with the interior luminal surface 132 of the patient's vasculature 130. As described in U.S. patent application Ser. No. 09/917,371 to Chobotov et al., now U.S. Pat. No. 6,761,733, and which is incorporated by reference herein in its entirety, a release belt may be disposed in one or more grooves (not shown) disposed on one or more struts 168 which may assist in retaining the proximal self-expanding stent member 160 in the reduced diameter delivery configuration.

For example, upon deployment of stent graft 150, and more particularly the proximal self-expanding stent member 160, (typically accomplished, at least in part, by release of one or more belts, such as the proximal releasable belts 104 and 106), the radial expansion of the proximal self-expanding stent member 160 results in a displacement of struts 168 so that the distance between them increases. Eventually, the displacement between the struts 168 become large enough to enable the barbs 165 to be released from behind the adjacent strut 168 and/or tuck pad 166 and engage the interior luminal surface 132 of the patient's vasculature 130. In general, the barbs 165 may release into a position suitable for engaging the interior luminal surface 132 of a patient's vasculature with a time constant that is generally an order of magnitude lower than the time constant associated with the radial expansion of the stent 500 embodiment or anchor member (such as the proximal self-expanding stent member 160). In other words, during the stent 500 or anchor member deployment process, the one or more barbs 165 may complete their deployment before the stent 500 or anchor member is fully expanded so that the barbs 165 may engage the interior luminal surface 132 of the vasculature 130 with maximum effectiveness.

Referring again to FIG. 9, the proximal self-expanding stent member 160 may include struts 168, any one of which may further comprise one or more barbs 165. In addition, optional tuck pads 166 may be positioned along a strut 168 such that the tuck pad 166 is coaxially aligned with a barb 165 on a neighboring strut 168 in order to shield the neighboring barb 165 at least when the stent graft 150 is in its reduced diameter delivery configuration. Struts 168 and/or tuck pads 166 may also include a tuck slot 167 which may assist in retaining a barb 165 while the stent graft 150 (and consequently the proximal self-expanding stent member 160) is in its reduced diameter delivery configuration. Upon deployment of a stent graft 150 embodiment, the one or more barbs 165 may be released from respective tuck slots 167 and thereafter placed in an operational or deployed configuration for engaging a patient's vasculature 130.

Figure 12:
FIG. 12 is a transverse cross section view of the stent portion of FIG. 11 taken along lines 12-12 of FIG. 11.

FIG. 11 shows a portion of a cylindrical stent embodiment 500 in a generally constrained and flattened configuration having struts 168 with a coaxial enlarged portion 180 embodiments and undulating deflected portions 182. The undulating deflected portions 182 may have barbs 165 positioned at offset proximal and distal locations along neighboring struts 168 which may aid in efficiently compacting the struts 168 and barbs 165 in a constrained configuration for delivery into a patient's body. By alternating axial location of the barbs 165 and/or enlarged portions 180 along neighboring struts 168, the stent 500 may be optimally compressed. The undulating deflected portions 182 of a strut 168 may enable multiple lateral contact points within the stent 500. Such multiple contact points may aid in restraining or compacting the stent 500 in a constrained/non-expanded state. In some embodiments, one or more struts 168 may have enlarged longitudinal sections or enlarged portions 180 that may be disposed in a substantially longitudinal orientation between the proximal end and distal end of the stent 500 when the stent 500 is in the constrained state. Additionally, the one or more struts 168 may be disposed in an undulating pattern. FIG. 12 shows a transverse cross section view of the stent 500 portion of FIG. 11 taken along lines 12-12 of FIG. 11. FIG. 12 illustrates an example of the varying circumferential cross sectional areas 169 of the struts 168 taken along a transverse cross section of the strut 500.

Figure 13:
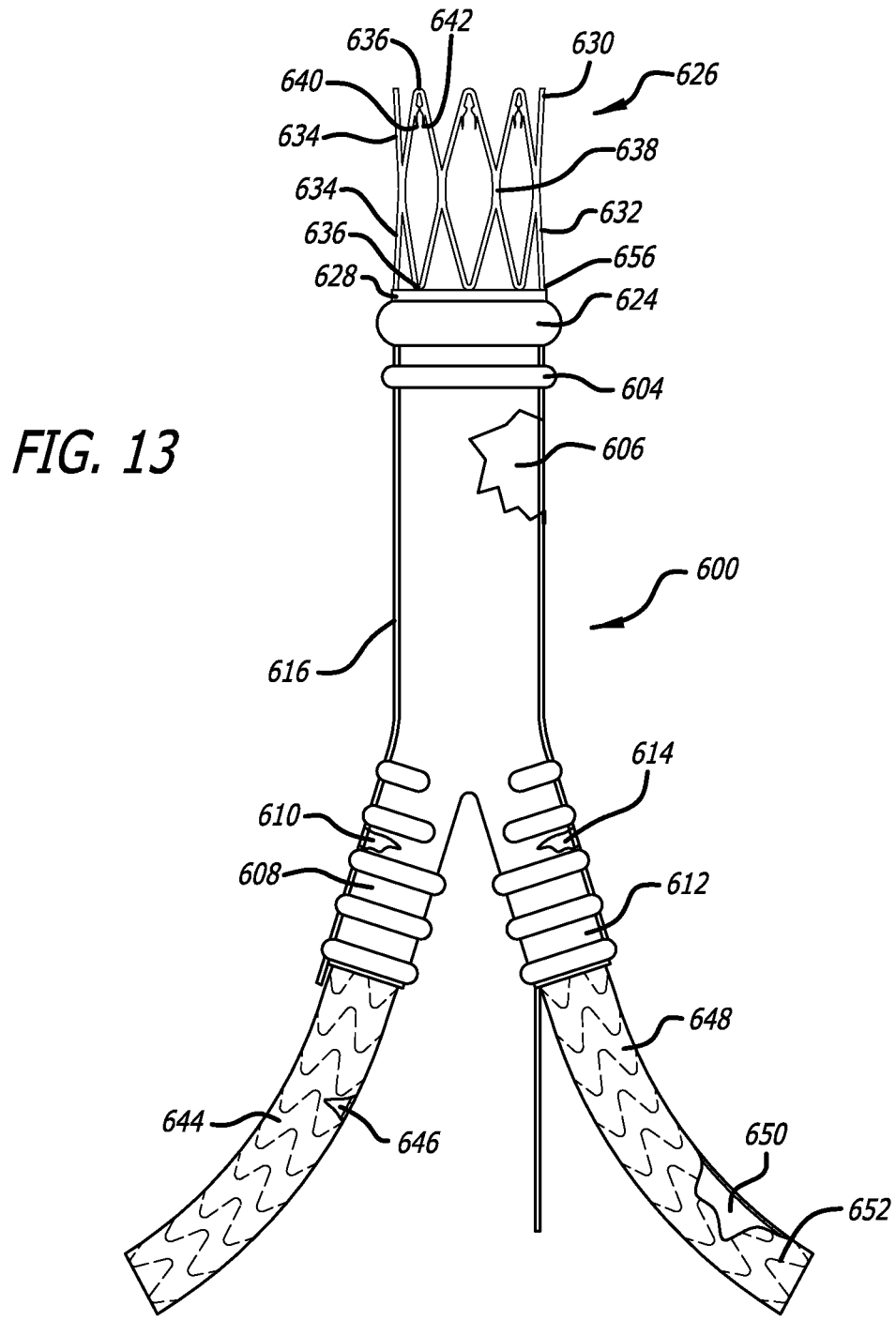
FIG. 13 is an elevation view of a bifurcated stent graft embodiment.

As discussed above, some embodiments of a modular endovascular stent graft assembly may include a bifurcated graft member 600 with a proximal stent or anchor member 602 secured thereto. In some cases, the main body member 604 may be formed from a supple graft material, such as ePTFE, having a main fluid flow lumen 606 therein. FIG. 13 illustrates such an embodiment. Referring to this figure, the main graft portion 604 may include an ipsilateral leg 608 with an ipsilateral fluid flow lumen 610 in communication with the main fluid flow lumen 606, a contralateral leg 612 with a contralateral fluid flow lumen 614 in communication with the main fluid flow lumen 606 and a network of inflatable channels 616 disposed on the main graft member 604. For some embodiments, the main graft or main body member 604 may have an axial length of about 5 cm to about 10 cm, more specifically, about 6 cm to about 8 cm in order to span an aneurysm 622 of a patient's aorta 618 without engaging the patient's iliac arteries 620 directly with the legs 608 and 612 of the main graft member 604 (see FIG. 14).

The inflatable channels of the network of inflatable channels 616 may be disposed on any portion of the main graft or main body member 604 including the ipsilateral and contralateral legs 608 and 612. The network of inflatable channels 616 may be configured to accept a hardenable fill material to provide structural rigidity to the main body 604 member when the network of inflatable channels 616 are in an inflated state and the inflation material has been cured or hardened. Radiopaque inflation material may be used to facilitate monitoring of the fill process and subsequent engagement of graft extensions. The network of inflatable channels 616 may also include at least one inflatable cuff 624 disposed on a proximal portion of the main body member which may be configured to seal against an inside surface of a patient's vessel, such as the aorta.

The proximal anchor member 626, which may have a substantially tubular or cylindrical configuration, may be disposed at a proximal end 628 of the main body member 604 and secured to the main body member 604 in any suitable manner including stitching, adhesive bonding, welding, and the like. The proximal anchor member 626 may also be secured to the main body 604 with a resilient connector ring (not shown) which may be embedded in a proximal end or portion 628 the main body 604. The proximal anchor member 626 may have a self-expanding proximal stent portion 630 secured to a self-expanding distal stent portion 632. Each of these stent portions 630 and 632 may include an undulating elongate stent element that may be disposed in a somewhat serpentine or sinusoidal configuration, as shown above with regard to stent members 160 and 170. Each of the stent portions 630 and 632 of the proximal anchor member 626 of the stent graft 600 in FIG. 13 may share any or all of the features, dimensions or materials of stent members 160 and 170 discussed above. For example, the proximal and distal stent portions 630 and 632 of the proximal anchor member 626 may include tapered struts 634 that extend between crown portions 636 of each respective stent portion 630 or 632. Such tapered struts 634 may have any or all of the features, dimensions, and materials of the struts discussed above and include a tapered strut configuration that allows for the strain imposed on the strut structure to be evenly distributed through the structure of the stent portion or portions 630 and 632.

In some cases, the proximal stent portion 630 may be secured to the distal stent portion 632 with one or more struts or strut segments 638 disposed between the respective proximal and distal stent sections 630 and 632. Some embodiments of such interconnecting struts 638 may have a cross sectional area that is substantially the same as or greater than a cross sectional area of proximal stent portions 630 or distal stent portions 632 adjacent the strut 638. Such configurations may be useful in avoiding points of concentrated stress in the proximal anchor member 602 or struts 638 which couple components thereof. For some embodiments, the proximal stent portion 630 of the proximal anchor member 602 may further include a plurality of barbs 640 having sharp tissue engaging tips 642 that are configured to extend in a radial outward direction in a deployed expanded state (see FIG. 15). For some embodiments, each stent portion 630 and 632 of the proximal anchor member 602 may include about 5 crowns 636 to about 8 crowns 636 at either end of the respective section 630 or 632 and may be made from a superelastic alloy such as superelastic NiTi alloy.

At least one tubular ipsilateral graft extension 644 having a fluid flow lumen 646 disposed therein may be deployed with the fluid flow lumen 646 of the graft extension 644 sealed to and in fluid communication with the fluid flow lumen 610 of the ipsilateral leg 608 of the main body member 604. In addition, at least one tubular contralateral graft extension 648 having a fluid flow lumen 650 disposed therein may be deployed with the fluid flow lumen 650 of the graft extension 648 sealed to and in fluid communication with the fluid flow lumen 614 of the contralateral leg 612 of the main body member 604. For some embodiments, the graft extensions 644 and 648 may include an interposed self-expanding stent 652 disposed between at least one outer layer and at least one inner layer of supple layers of graft material. The interposed stent disposed between the outer layer and inner layer of graft material may be formed from an elongate resilient element helically wound with a plurality of longitudinally spaced turns into an open tubular configuration. For some embodiments, the interposed stent 652 may include a superelastic alloy such as superelastic NiTi alloy. In addition, the graft material of each graft extension 644 and 648 may further include at least one axial zone of low permeability for some embodiments.

For some embodiments, an outside surface of the graft extension 648 may be sealed to an inside surface of the contralateral leg 612 of the main body 604 when the graft extension 648 is in a deployed state. For some embodiments, the axial length of the ipsilateral and contralateral legs 608 and 612 may be sufficient to provide adequate surface area contact with outer surfaces of graft extensions 644 and 648 to provide sufficient friction to hold the graft extensions 644 and 648 in place. For some embodiments, the ipsilateral and contralateral legs 608 and 612 may have an axial length of at least about 2 cm. For some embodiments, the ipsilateral and contralateral legs 608 and 612 may have an axial length of about 2 cm to about 6 cm, more specifically, about 3 cm to about 5 cm.

Figure 14:
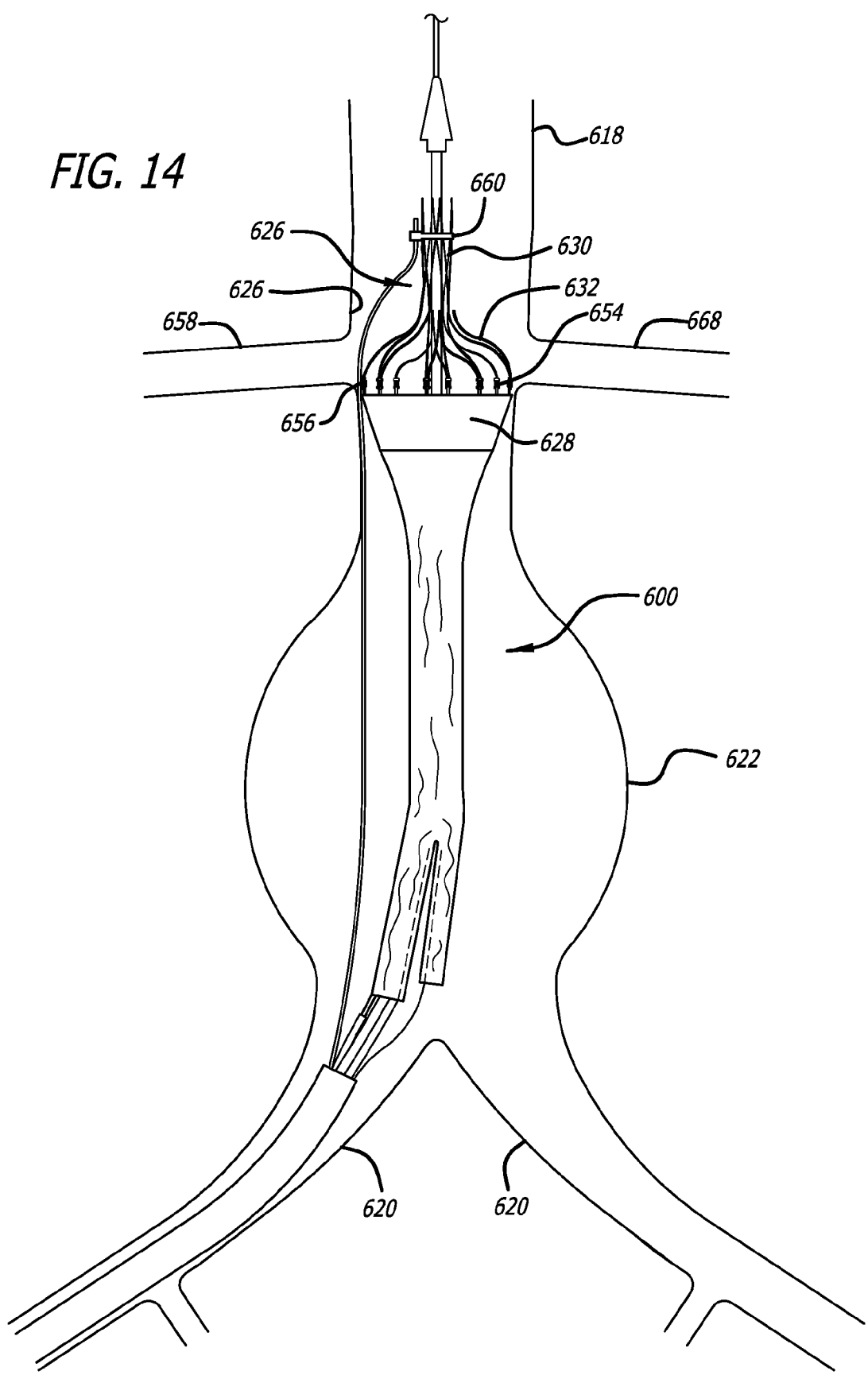
FIG. 14 illustrates and embodiment of the stent graft of FIG. 13 partially deployed within a patient's aorta.

For the bifurcated stent graft embodiment 600 discussed above or any other suitable stent graft embodiment discussed herein that includes a proximal self-expanding anchor member 602, it may be desirable in some cases to constrain each of the proximal and distal stent portions 630 and 632 separately so that each of the proximal and distal stent portions 630 and 632 of the proximal anchor member 602 can be deployed from a radially constrained state independent of each other. FIG. 14 shows the stent graft 600 having an 8 crown distal stent portion 632 with marker elements 654 disposed at a distal end 656 of the distal stent portion 632. Other than this variation in the proximal anchor configuration, the stent graft of FIG. 14 may have the same features, dimensions and materials as those of the stent graft 600 shown in FIG. 13.

The stent graft 600 of FIG. 14 is shown in a partially deployed state within an abdominal aorta 618 of a patient with the proximal end 628 of the main body 604 disposed just below and in a non-interfering relationship with the renal arteries 658 which extend from and are in communication with the patient's aorta. The main body 604 of the stent graft 600 also extends substantially across the aneurysm 622 of the aorta 618, however, this relationship may vary depending on the size of the graft 600 used and the morphology of the aneurysm 632. The proximal stent portion 630 of the proximal anchor member 602 is still constrained by a releasable member or belt 660 such that it has an outer dimension or profile suitable for delivery within a catheter assembly within the patient's vasculature. The distal stent portion 632, however, has been released from a constrained state and has expanded radially such that the distal end 656 of the distal stent portion 632 has expanded outwardly in approximation to the inner surface 662 of the patient's aorta 618.

In such cases, a proximal anchor member 602 configured to allow the distal end 656 of the distal stent portion 632 to so expand may be desirable. For example, the markers 654 disposed at the distal end 656 of the distal stent portion 632 are substantially open and are close to or in contact with the inner wall 662 of the patient's aorta 68 providing good visualization of the position of the partially deployed stent graft 600 under fluoroscopy. This configuration may allow the physician deploying the stent graft 600 to visualize the position of the stent graft 600 and accurately predict what the final position of the stent graft 600 will be after complete deployment. However, such a configuration may also allow the physician to adjust the position of the stent graft 600 prior to full deployment of the proximal anchor member 602. In other words, the stent graft 600 and markers 654 at the distal end 656 of the distal stent portion 632 are sufficiently expanded so that the physician can easily see how the stent graft 600 will be positioned when fully deployed before the physician has deployed the proximal stent portion 630 in which case the barbs 640 or other tissue engaging members of the proximal stent portion 630 engage the tissue of the inner wall 662 of the patient's aorta 618.

We have found that in some instances, in order to configure an anchor member 602 such that the distal end 656 of the distal stent portion 632 opens or radially expands sufficiently upon release from a constrained state, that certain design parameters or criteria may be desirable. In particular, such a stent portion 632 may benefit from a configuration that produces a good distal opening force or maximum opening force in an outward radial direction. In order to produce a generous opening force in an outward radial direction, the section of the struts 634 and crowns 636 of the proximal and distal stent portions 630 and 632 may be increased, however, it may also be desirable to adjust the tapering profile of the struts 634 in order to maintain a substantially even distribution of strain throughout the structure of the stent portions 630 and 632. For some embodiments, a useful outward opening force may include about 0.5 to about 0.75 lbf of force for a stent embodiment that is about 14 mm to about 16 mm in outer diameter in a relaxed unconstrained state.

In cases such as the stent graft embodiment 600 of FIG. 13 wherein the proximal anchor member 602 includes both a proximal stent portion 630 and a distal stent portion 632, it may be useful to vary the axial lengths of the respective proximal and distal portions 630 and 632 of the anchor member 602. Such an unsymmetric arrangement may be beneficial in cases such as the partial deployment sequence step shown in FIG. 14 wherein the constraint on the distal stent portion 632 has been released so as to allow radial expansion of the distal portion 632 but the proximal stent portion 630 remains constrained.

Figure 15:
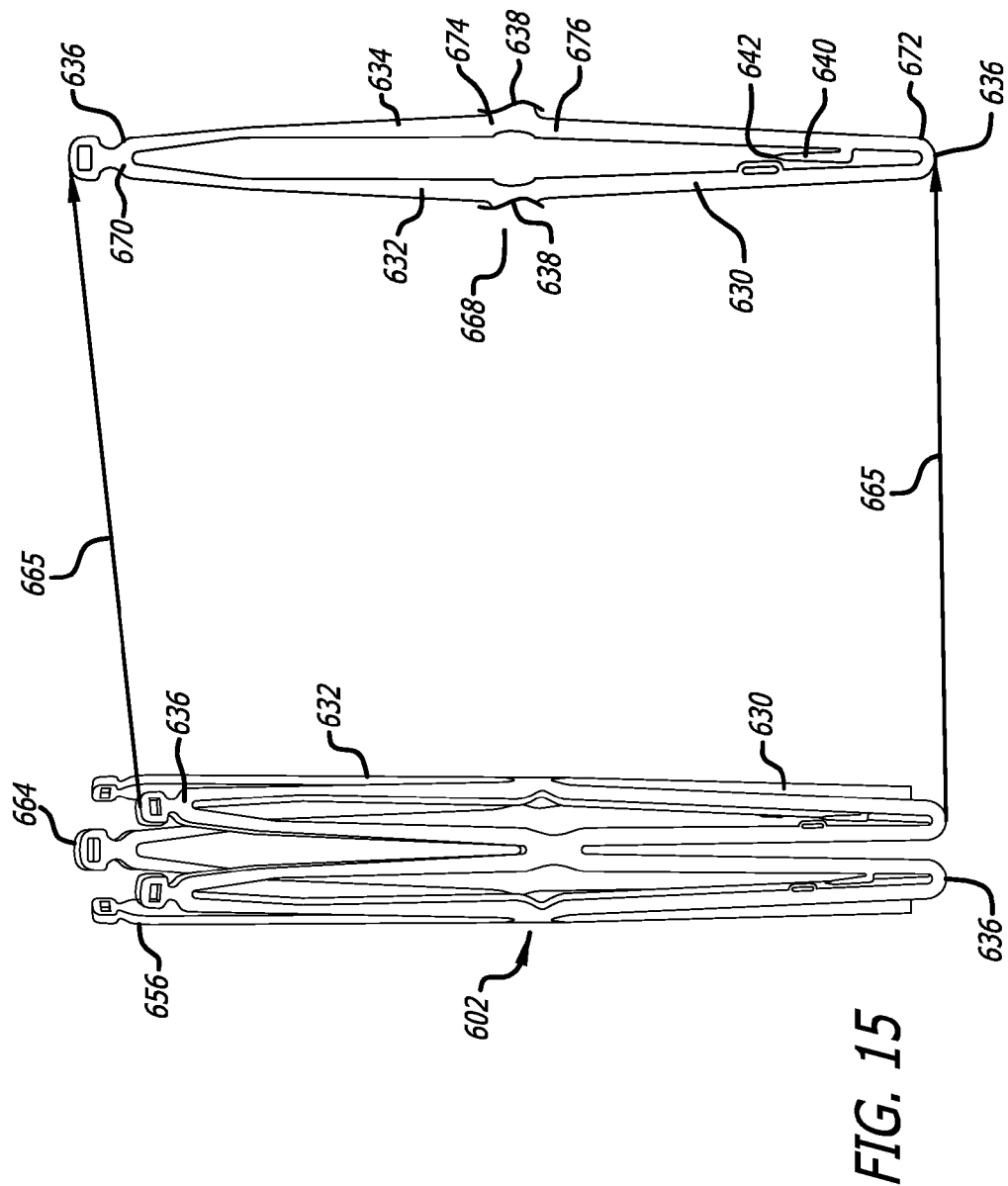
FIG. 15 is a perspective view of a proximal anchor member embodiment.

FIG. 15 illustrates an embodiment of the proximal anchor member 602 having a 5 crown proximal stent portion 630 and a five crown distal stent portion 632. An attachment ring 664 is secured to each crown 636 of the distal end 656 of the distal stent portion 632. Such attachment rings 664 may be secured to the proximal end 628 of main body 604 by stitching the ring 664 to the flexible material of the main body portion 604 with suture or any other suitable material. Such attachment rings 664 may also be secured to the main body 604 by any other suitable method including any of the attachment methods and devices discussed above. A cutaway portion 668 of the proximal anchor member 602 is shown at the ends of arrows 665 to illustrate an element of the proximal anchor member 602 for further discussion. The cutaway portion 668 includes a distal crown 670 and respective stent struts 634 attached thereto from the distal stent portion 632 and a proximal crown 672 and respective stent struts 634 attached thereto from the proximal stent portion 630. The proximal end of the distal stent portion 632 is secured to the distal end 676 of the proximal stent portion 630 by strut segments 638.

Figure 16:
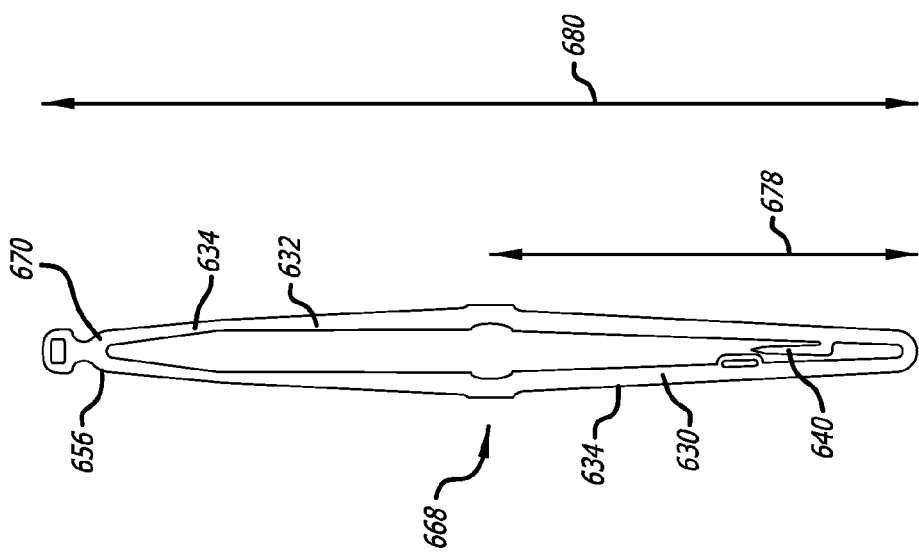
FIG. 16 is an elevation view of a cut away portion of the proximal anchor member embodiment of FIG. 15.

FIG. 16 illustrates the cutaway portion 668 of the proximal anchor member 602 of FIG. 15 with an adjacent arrow 678 that indicates the axial length of the proximal stent portion 630 and an arrow 680 that indicates the axial length of the proximal stent portion 630 together with the distal stent portion 632 or, in other words, the axial length of the proximal anchor member 602 as a whole. For some embodiments, it has been determined that one or more of the design parameters discussed above may be optimized by use of a proximal anchor member 602 having a proximal stent portion 630 and a distal stent portion 632 wherein the axial length of the proximal anchor member 602 as a whole ($L_{stent}$) divided by the axial length of the proximal stent portion 630 ($L_{proximal}$) is a ratio of about 1.75 to about 2.5, more specifically, about 1.75 to about 2.1, and even more specifically, about 1.75 to about 1.9. Such a configuration may be useful for a multi-element stent or proximal anchor member 602 in order to maximize opening force and minimize peak strain within the proximal anchor member 602.

Figure 17:
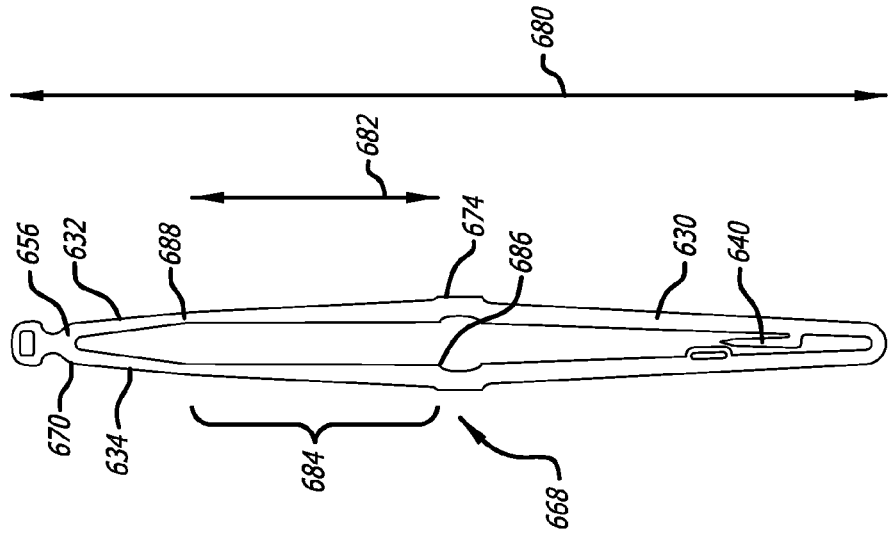
FIG. 17 is an elevation view of a cut away portion of the proximal anchor member embodiment of FIG. 16.

It has also been discovered that for such proximal anchor member embodiments 600 as shown in FIG. 16 including unsymmetric axial lengths of the proximal stent portion 630 and distal stent portion 632, that it may also be useful to include unsymmetric taper lengths. FIG. 17 illustrates the cutaway portion 668 of the proximal anchor member 602 of FIG. 15 with an arrow 682 that indicates the axial length of the tapered portion 684 of the strut 634 that tapers from the proximal end 674 of the distal stent portion 632 towards the distal end 656 of the distal stent portion 632. Such a tapered portion 684 extends from the crown 686 of the distal stent portion 632 at a proximal end thereof to an axial position of minimum strut cross section 688 between the proximal crown 686 and distal crown 670 of the distal stent portion 632. Distal of the position of minimum section 688 on the strut 634, the strut 634 may begin to flare and increase in section towards the distal crown 670. Thus, the point of minimum section 688 on the strut 634 represents the endpoint of the tapered portions 684 of the strut 634 which begin at each respective crown 670 and 686 of the distal stent portion 632. For some stent embodiments 602, a strut taper configuration wherein the axial length of the proximal anchor member as a whole 602 or $L_{stent}$ divided by the axial length of the tapered strut 634 from the crown 686 of the distal stent portion 632 at a proximal end 674 thereof to an axial position of minimum strut cross section 688 between the proximal crown 686 and distal crown 670 of the distal stent portion 632 ($L_{taper}$) is about 3.0 to about 4.5, may be particularly useful in order to maximize opening force and reduce or minimize peak strains within the structure of the proximal anchor member 602. It should also be noted that such unsymmetric taper lengths may also be used for multi-element stents or proximal anchor members 602 having stent portions 630 and 632 of equal axial length.

Figure 18:
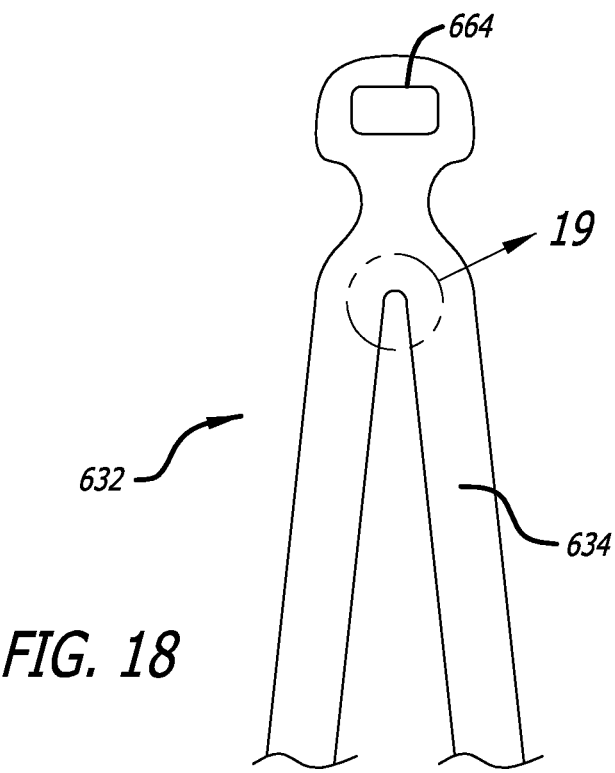
FIG. 18 shows a distal portion of the cut away portion of the proximal anchor member of FIG. 16.
Figure 19:
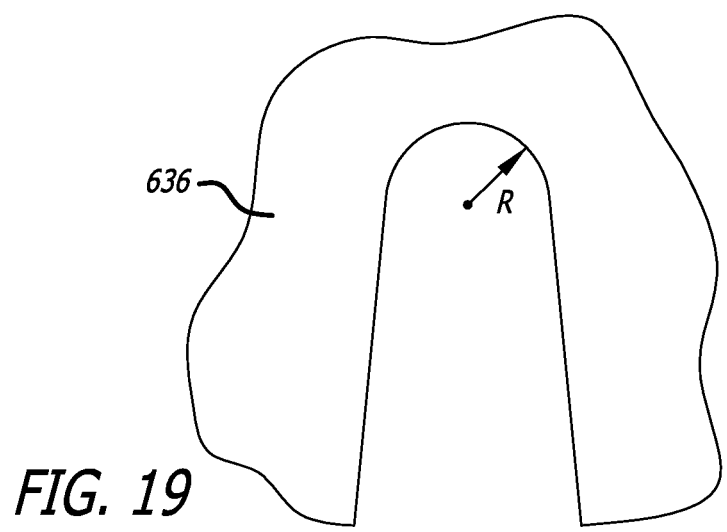
FIG. 19 is an enlarged view of the encircled portion 19-19 in FIG. 18.

Another design parameter that may be useful when maximizing opening force and minimizing peak strain within a proximal anchor member 602 is selection of the inner crown radius of the crowns 636 at each end of the respective proximal and distal stent portions 630 and 632. FIGS. 18 and 19 illustrate an inner crown radius R of a distal crown 670 of the distal stent portion 632 of the proximal anchor member 602. For some embodiments, it may be useful to have an inner crown radius R of about 0.001 inches to about 0.005 inches, more specifically, about 0.001 inches to about 0.004 inches. It should be noted that such inner crown radii dimensions R may also be used for single element stents or proximal anchor members 160 and 170, particularly in embodiments where it is desirable to maximize opening force and minimize peak strains within the proximal anchor member.

For some particular stent graft embodiments 600 having a bifurcated main body 604 and a multi-element proximal anchor member 602, the proximal anchor member 602 may be configured to open to a maximum diameter of about 29 mm to about 31 mm, more specifically, about 30 mm, the proximal anchor member may have an overall axial length $L_{stent}$ of about 35 mm to about 37 mm, more specifically, about 36 mm, an opening force of about 0.5 lbf to about 0.7 lbf, more specifically, about 0.6 lbf, and a ratio of the axial length 680 of the anchor member 602 $L_{stent}$ divided by the axial length 678 of the proximal stent portion 630 $L_{proximal}$ of about 2.0 to about 2.2, more specifically, about 2.1. Such an embodiment 600 may also have a distal stent portion 632 with a strut taper configuration wherein the length 680 of the proximal anchor member 602 as a whole $L_{stent}$ divided by the length 682 of the tapered strut 639 from the crown 686 of the distal stent portion 632 at a proximal end thereof to an axial position of minimum strut cross section 688 between the proximal crown 686 and distal crown 670 of the distal stent portion 632 ($L_{taper}$) is about 3.0 to about 3.2, more specifically, about 3.1. Many other embodiments following the design parameters discussed above may also be used in order to maximize opening force and minimize peak strain within the proximal anchor member 602. As discussed above, these design parameters may also be used singly or in any combination in order to achieve the desired results in either single element stents 160 and 170 or multi-element stents 600 having a proximal stent portion 630, distal stent portion 632 or any other number of stent portions.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The number of barbs, enlarged portions or tapers per strut, the length of each barb, enlarged portions or tapers, each of the barb angles or tapered angle described above, and the barb, enlarged portion or tapered orientation may vary from barb to barb, enlarged portion to enlarged portion, strut to strut within a single stent or between multiple stents within a single graft.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although embodiments of the invention have been described in substantial detail with reference to one or more specific embodiments, those of ordinary skill in the art will recognize that changes may be made to the embodiments specifically disclosed in this application, yet these modifications and improvements are within the scope and spirit of the invention.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this invention.

Certain embodiments of the invention are set forth in the claim(s) that follow(s).

What is claimed is:

1. An endovascular stent graft, comprising:
   a main body portion including at least one tubular portion made from at least one layer of flexible material; and
   a self-expanding proximal anchor member which includes:
      a constrained state,
      a relaxed expanded state,
      a proximal stent portion,
      a distal stent portion with a proximal end of the distal stent portion secured to a distal end of the proximal stent portion and a distal end of the distal stent portion secured to a proximal end of the main body portion, and wherein the axial length of the self-expanding anchor member as a whole divided by the axial length of the proximal stent portion is about 1.75 to about 2.5, and wherein an axial length of the self-expanding proximal anchor member as a whole divided by an axial length of a tapered strut from a proximal crown of the distal stent portion at a proximal end thereof to an axial position of minimum strut cross section between the proximal crown and a distal crown of the distal stent portion is a ratio of about 3.0 to about 4.5.

2. A self-expanding anchor member, comprising:
   a constrained state,
   a relaxed expanded state,
   a proximal stent portion,
   a distal stent portion with a proximal end of the distal stent portion secured to a distal end of the proximal stent portion, and wherein an axial length of the self-expanding anchor member as a whole divided by the axial length of the proximal stent portion is about 1.75 to about 2.5 and wherein an axial length of the self-expanding anchor member as a whole divided by an axial length of a tapered strut from a proximal crown of the distal stent portion at a proximal end thereof to an axial position of minimum strut cross section between the proximal crown and a distal crown of the distal stent portion is a ratio of about 3.0 to about 4.5.

* * * * *